United States Patent
Libbus et al.

(10) Patent No.: US 7,596,413 B2
(45) Date of Patent: Sep. 29, 2009

(54) COORDINATED THERAPY FOR DISORDERED BREATHING INCLUDING BAROREFLEX MODULATION

(75) Inventors: Imad Libbus, St. Paul, MN (US); Quan Ni, Shoreview, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 577 days.

(21) Appl. No.: 10/863,827

(22) Filed: Jun. 8, 2004

(65) Prior Publication Data

US 2005/0288729 A1   Dec. 29, 2005

(51) Int. Cl.
*A61N 1/08* (2006.01)
*F16K 31/02* (2006.01)

(52) U.S. Cl. .................. 607/42; 607/18; 128/204.23
(58) Field of Classification Search .......... 607/1–5, 607/9, 15, 26, 42, 44–46, 48; 128/200.24, 128/204.18, 204.21, 204.23
See application file for complete search history.

(56) References Cited

U.S. PATENT DOCUMENTS

| | | |
|---|---|---|
| 3,309,924 A | 3/1967 | Kolin et al. |
| 3,522,811 A | 8/1970 | Schwartz et al. |
| 3,650,277 A | 3/1972 | Sjostrand et al. |
| 3,835,864 A | 9/1974 | Rasor et al. |
| 3,870,051 A | 3/1975 | Brindley |
| 3,943,936 A | 3/1976 | Rasor et al. |
| 4,323,073 A | 4/1982 | Ferris |
| 4,562,841 A | 1/1986 | Brockway et al. |
| 4,573,481 A | 3/1986 | Bullara |
| 4,590,946 A | 5/1986 | Loeb et al. |
| 4,719,921 A | 1/1988 | Chirife |
| 4,791,931 A | 12/1988 | Slate |
| 4,819,662 A | 4/1989 | Heil et al. |
| 4,940,065 A | 7/1990 | Tanagho et al. |
| 4,960,129 A | 10/1990 | dePaola et al. |
| 4,967,159 A | 10/1990 | Manes |
| 4,972,848 A | 11/1990 | Di Domenico |
| 5,036,849 A | 8/1991 | Hauck et al. |
| 5,040,533 A | 8/1991 | Feamot |
| 5,144,960 A | 9/1992 | Mehra et al. |
| 5,199,428 A * | 4/1993 | Obel et al. .............. 607/44 |

(Continued)

FOREIGN PATENT DOCUMENTS

WO    WO9301862    2/1993

(Continued)

OTHER PUBLICATIONS

Andersen, Long-term follow-up of patients from a randomized trial of atrial versus vetricular pacing for sick-sinus syndrome, Lancet, 350(9086), Oct. 25, 1997, 1210-6.

(Continued)

*Primary Examiner*—Carl H Layno
*Assistant Examiner*—Jessica Reidel
(74) *Attorney, Agent, or Firm*—Hollingsworth & Funk

(57) ABSTRACT

An approach to providing disordered breathing therapy involves the use of a plurality of therapy devices to deliver a coordinated disordered breathing therapy regimen to the patient. The plurality of disordered breathing devices includes at least a therapy device that delivers an electrical stimulation therapy modulating a patient's baroreflex response. Other therapy devices may include a cardiac electrical stimulation device, an external respiratory therapy device, and/or other therapy devices used in the treatment of disordered breathing. A therapy controller coordinates the therapies delivered by the plurality of therapy devices.

36 Claims, 39 Drawing Sheets

U.S. PATENT DOCUMENTS

| | | | |
|---|---|---|---|
| 5,203,326 A * | 4/1993 | Collins | 607/4 |
| 5,203,348 A | 4/1993 | Dahl et al. | |
| 5,215,089 A | 6/1993 | Baker, Jr. | |
| 5,230,337 A | 7/1993 | Dahl et al. | |
| 5,282,468 A | 2/1994 | Klepinski | |
| 5,284,136 A | 2/1994 | Hauck et al. | |
| 5,330,507 A | 7/1994 | Schwartz | |
| 5,330,515 A | 7/1994 | Rutecki et al. | |
| 5,335,657 A * | 8/1994 | Terry et al. | 607/45 |
| 5,351,394 A | 10/1994 | Weinberg | |
| 5,360,442 A | 11/1994 | Dahl et al. | |
| 5,366,496 A | 11/1994 | Dahl et al. | |
| 5,376,476 A | 12/1994 | Eylon | |
| 5,391,200 A | 2/1995 | KenKnight et al. | |
| 5,397,342 A | 3/1995 | Heil, Jr. et al. | |
| 5,411,540 A | 5/1995 | Edell et al. | |
| 5,437,285 A | 8/1995 | Verrier et al. | |
| 5,540,727 A | 7/1996 | Tockman et al. | |
| 5,540,734 A * | 7/1996 | Zabara | 607/46 |
| 5,540,735 A | 7/1996 | Wingrove | |
| 5,545,202 A | 8/1996 | Dahl et al. | |
| 5,571,150 A | 11/1996 | Wernucke et al. | |
| 5,603,732 A | 2/1997 | Dahl et al. | |
| 5,643,330 A | 7/1997 | Holsheimer et al. | |
| 5,645,570 A | 7/1997 | Corbucci | |
| 5,683,430 A | 11/1997 | Markowitz et al. | |
| 5,700,282 A | 12/1997 | Zabara | |
| 5,707,400 A | 1/1998 | Terry, Jr. et al. | |
| 5,727,558 A | 3/1998 | Hakki et al. | |
| 5,766,236 A | 6/1998 | Detty et al. | |
| 5,800,464 A | 9/1998 | Kieval | |
| 5,836,987 A | 11/1998 | Baumann et al. | |
| 5,861,015 A | 1/1999 | Benja-Athon | |
| 5,916,243 A | 6/1999 | KenKnight et al. | |
| 5,919,220 A | 7/1999 | Stieglitz et al. | |
| 5,928,272 A | 7/1999 | Adkins et al. | |
| 5,938,596 A | 8/1999 | Woloszko et al. | |
| 5,974,340 A * | 10/1999 | Kadhiresan | 607/18 |
| 5,989,230 A | 11/1999 | Frassica | |
| 6,006,134 A | 12/1999 | Hill et al. | |
| 6,016,449 A | 1/2000 | Fishell et al. | |
| 6,044,298 A | 3/2000 | Salo et al. | |
| 6,050,952 A | 4/2000 | Hakki et al. | |
| 6,055,454 A | 4/2000 | Heemels | |
| 6,073,048 A * | 6/2000 | Kieval et al. | 607/17 |
| 6,110,098 A | 8/2000 | Renirie et al. | |
| 6,161,047 A | 12/2000 | King et al. | |
| 6,178,349 B1 | 1/2001 | Kieval | |
| 6,206,914 B1 | 3/2001 | Soykan et al. | |
| 6,208,894 B1 | 3/2001 | Schulman et al. | |
| 6,221,011 B1 | 4/2001 | Bardy | |
| 6,270,457 B1 | 8/2001 | Bardy | |
| 6,280,380 B1 | 8/2001 | Bardy | |
| 6,292,695 B1 | 9/2001 | Webster et al. | |
| 6,292,703 B1 | 9/2001 | Meier et al. | |
| 6,312,378 B1 | 11/2001 | Bardy | |
| 6,336,903 B1 | 1/2002 | Bardy | |
| 6,356,788 B2 | 3/2002 | Boveja | |
| 6,358,203 B2 | 3/2002 | Bardy | |
| 6,368,284 B1 | 4/2002 | Bardy | |
| 6,397,109 B1 | 5/2002 | Cammilli et al. | |
| 6,398,728 B1 | 6/2002 | Bardy | |
| 6,401,129 B1 | 6/2002 | Lenander | |
| 6,438,428 B1 | 8/2002 | Axelgaard et al. | |
| 6,440,066 B1 | 8/2002 | Bardy | |
| 6,442,435 B2 | 8/2002 | King et al. | |
| 6,473,644 B1 | 10/2002 | Terry, Jr. et al. | |
| 6,522,926 B1 | 2/2003 | Kieval et al. | |
| 6,564,101 B1 | 5/2003 | Zikria | |
| 6,574,507 B1 * | 6/2003 | Bonnet | 607/20 |
| 6,600,956 B2 | 7/2003 | Maschino et al. | |
| 6,622,041 B2 | 9/2003 | Terry et al. | |
| 6,881,192 B1 * | 4/2005 | Park | 600/529 |
| 6,894,204 B2 | 5/2005 | Dunshee | |
| 6,942,686 B1 | 9/2005 | Barbut et al. | |
| 7,010,337 B2 | 3/2006 | Furnary et al. | |
| 7,025,730 B2 * | 4/2006 | Cho et al. | 600/529 |
| 7,130,687 B2 * | 10/2006 | Cho et al. | 607/17 |
| 7,155,278 B2 * | 12/2006 | King et al. | 607/2 |
| 7,155,284 B1 | 12/2006 | Whitehurst et al. | |
| 7,194,313 B2 * | 3/2007 | Libbus | 607/42 |
| 7,218,964 B2 | 5/2007 | Hill et al. | |
| 7,277,757 B2 | 10/2007 | Casavant et al. | |
| 7,277,761 B2 | 10/2007 | Shelchuk | |
| 7,366,572 B2 * | 4/2008 | Heruth et al. | 607/48 |
| 7,468,040 B2 * | 12/2008 | Hartley et al. | 600/529 |
| 7,469,697 B2 * | 12/2008 | Lee et al. | 128/200.24 |
| 7,499,742 B2 | 3/2009 | Bolea | |
| 7,509,166 B2 | 3/2009 | Libbus | |
| 2002/0005982 A1 | 1/2002 | Borlinghaus | |
| 2002/0068897 A1 | 6/2002 | Jenkins et al. | |
| 2002/0103516 A1 | 8/2002 | Patwardhan et al. | |
| 2002/0128700 A1 | 9/2002 | Cross, Jr. | |
| 2002/0151051 A1 | 10/2002 | Li | |
| 2002/0165462 A1 * | 11/2002 | Westbrook et al. | 600/529 |
| 2002/0193697 A1 * | 12/2002 | Cho et al. | 600/529 |
| 2003/0060848 A1 * | 3/2003 | Kieval et al. | 607/2 |
| 2003/0060858 A1 * | 3/2003 | Kieval et al. | 607/44 |
| 2003/0153953 A1 * | 8/2003 | Park et al. | 607/17 |
| 2003/0171791 A1 * | 9/2003 | KenKnight et al. | 607/60 |
| 2003/0195571 A1 * | 10/2003 | Burnes et al. | 607/9 |
| 2003/0199945 A1 * | 10/2003 | Ciulla | 607/48 |
| 2003/0216789 A1 * | 11/2003 | Deem et al. | 607/9 |
| 2003/0229380 A1 * | 12/2003 | Adams et al. | 607/9 |
| 2004/0002742 A1 * | 1/2004 | Florio | 607/19 |
| 2004/0186523 A1 * | 9/2004 | Florio | 607/17 |
| 2004/0193231 A1 | 9/2004 | David et al. | |
| 2004/0249416 A1 * | 12/2004 | Yun et al. | 607/2 |
| 2005/0039745 A1 | 2/2005 | Stahmann et al. | |
| 2005/0043772 A1 * | 2/2005 | Stahmann et al. | 607/42 |
| 2005/0061320 A1 * | 3/2005 | Lee et al. | 128/204.18 |
| 2005/0065567 A1 * | 3/2005 | Lee et al. | 607/42 |
| 2005/0090871 A1 * | 4/2005 | Cho et al. | 607/17 |
| 2005/0096705 A1 | 5/2005 | Pastore et al. | |
| 2005/0143779 A1 | 6/2005 | Libbus | |
| 2005/0149127 A1 | 7/2005 | Libbus | |
| 2005/0149129 A1 | 7/2005 | Libbus et al. | |
| 2005/0149130 A1 * | 7/2005 | Libbus | 607/9 |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus | |
| 2005/0149156 A1 | 7/2005 | Libbus et al. | |
| 2005/0288728 A1 * | 12/2005 | Libbus et al. | 607/42 |
| 2006/0047333 A1 | 3/2006 | Tockman et al. | |
| 2006/0106429 A1 | 5/2006 | Libbus et al. | |
| 2006/0206153 A1 | 9/2006 | Libbus | |
| 2006/0206154 A1 | 9/2006 | Moffitt | |
| 2006/0217772 A1 | 9/2006 | Libbus | |
| 2006/0224188 A1 | 10/2006 | Libbus et al. | |
| 2007/0038278 A1 | 2/2007 | Zarembo | |
| 2007/0093875 A1 | 4/2007 | Chavan et al. | |
| 2007/0142871 A1 | 6/2007 | Libbus | |
| 2007/0185542 A1 | 8/2007 | Bolea et al. | |

FOREIGN PATENT DOCUMENTS

| | | |
|---|---|---|
| WO | WO97018856 | 5/1997 |
| WO | WO9904841 | 4/1999 |

| | | |
|---|---|---|
| WO | WO01000273 | 1/2001 |
| WO | WO0176689 | 10/2001 |

OTHER PUBLICATIONS

Bilgutay et al., A new concept in the treatment of hypertension utilizing an implantable electronic device:"Baropacer", Trans Am Soc Artif Intern Organs., 10, 1964, 387-95.

Coleridge et al., The distribution, connexions and histology of baroreceptors in the pulmonary artery, with some observations on the sensory innervation of the ductus arteriosus, Journal of Physiology, 156, May 1961, 591-602.

Courtice et al., Effect of frequency and impulse pattern on the noncholinergic cardiac response to vagal stimulation in the toad, *Bufo marinus*, Journal of the Autonomic Nervous System, 48(3), Aug. 1994, 267-72. Abstract only.

De Landsheere et al., Effect of spinal cord stimulatin on regional myocardial perfusion assessed by positron emission tomography, American Journal of Cardiology, 69(14), May 1, 1992, 1143-9.

Garrigue et al., Night Atrial Overdrive with DDD Pacing Results in a Significant Reduction of Sleep Apnea Episodes and QQL Improvement in Heart Failure Patients, Hopital Cardiologique du Haut-Leveque, University of Bordeaux, Pessac-Bordeaux, France, 2001, p. 145.

Hilton et al., *Evaluation of Frequency and Time-frequency Spectral Analysis of Heart Rate Variability as a Diagnostic Marker of the Sleep Apnea Syndrome*, 37 Med. Biol. Eng. Comput. 760-769, 1999. Abstract only.

Javaheri et al., *Sleep Apnea in 81 Ambulatory Male Patients with Stable Heart Failure: Types and Their Prevalences, Consequences, and Presentations*, 97 Circulation 2154-2159, 1998.

Kandel et al., Part VII: Arousal, Emotion, and Behavioral Homeostasis, In: Principles of neural science, New York: McGraw-Hill, Heath Professions Division, 2000, 966-969.

Peters et al., Temporal and spatial summation caused by aortic nerve stimulation in rabbits. Effects of stimulation frequencies and amplitudes, Journal of the Autonomic Nervous System, 27(3), Aug. 1989, 193-205.

Satoh et al., "Role of Hypoxic Drive in Regulation of Postapneic Ventilation During Sleep in Patients with Obstructive Sleep Apnea", Am Rev Respir Dis, Mar. 1991 143 (3): 481-485.

Schuder et al., Ventricular Defibrillation in the Dog Using Implanted and Partially Implanted Electrode Systems, Am. J. of Cardiology, vol. 33, pp. 243-247, Feb. 1974.

Weber et al., Effects of CPAP and BIPAP on stroke volume in patients with obstructive sleep apnea syndrome. Pneumolgie Mar. 1995; 49(3):233-5. Translated Abstract only.

Terry Young et al., "The Occurrence of Sleep-disordered Breathing Among Middle-aged Adults", The New England Journal of Medicine, vol. 328, No. 17, pp. 1230-1235, 2002.

Bolea et al., Preliminary Statement for Baroreflex Therapy for Disordered Breathing dated Dec. 28, 2006, pp. 1-3.

Brattstrom, Influence of continuous and intermittent (R-Wave Triggered) electrical stimulation of the carotid sinus nerve on the static characteristic of the the circulatory regulator, Experientia 28:414-416, 1972. Abstract only.

Coleridge et al., Reflex Effects of Stimulating Baroreceptors in the Pulmonary Artery, J. Physiol., 1963, 166, pp. 197-210.

Ebert et al., Fentanyl-Diazepam Anesthesia with or without now Does Not Attenuate Cardiopulmonary Baroreflex-Mediated Vasoconstrictor Responses to Controlled Hypovolemia in Humans, Anesthesia and Analgesia, 1988, 67(6), pp. 548-554. Abstract only.

Liguori et al., Arystole and Severe Bradycardia during Epidural Anesthesia in Orthopedic Patients, Anesthesiology: vol. 86(1), Jan. 1997, pp. 250-257. No copy available.

McMahon et al., Reflex responses from the main pulmonary artery and bifurcation in anaesthetized dogs, Experimental Physiology, 2000, 85, 4, pp. 411-419.

Nishi et al., Afferent Fibres From Pulmonary Arterial Baroreceptors in the Left Cardiac Sympathetic Nerve of the Cat, j. Physiol. 1974, 240, pp. 53-66.

Peters et al., Cardiovascular response to time delays of electrocardiogram-coupled electrical stimulation of carotid sinus nerves in dogs, Journal of the Autonomic Nervous Systems, 25:173-180, 1988. Abstract only.

Peters et al., The principle of lectrical carotid sinus nerve stimulation: a nerve pacemaker system for angina pectoris and hypertension therapy, Annals of Biomedical Engineering, 8:445-458, 1980.

Reich, Implantation of a carotid sinus nerve stimulator, AORN Journal, pp. 53-56, Dec. 1969. No copy available.

Sedin, Responses of the cardiovascular system to carotid sinu nerve stimulation, Upsala J Med Sci, 81:1-17, 1976. Abstract only.

Warzel et al., Effects of carotis sinus nerve stimulation at different times in the respiratory and cardiac cycles on variability of heart rate and blood pressure of normotensive and renal hypertensive dogs, Journal of the Autonomic Nervous System, 26:121- 127, 1989. Abstract only.

Warzel et al., The effect of time of electrical stimulation of the carotid sinus on the amount of reduction in arterial pressure, Pfugers Arch, 337-44, 1972. Abstract only.

* cited by examiner

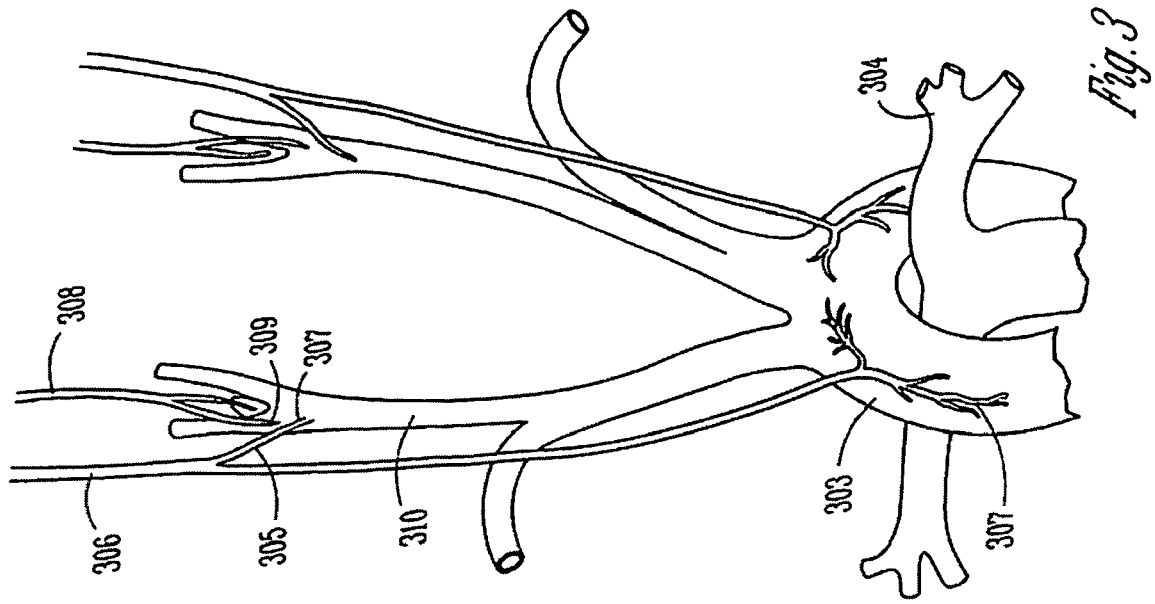
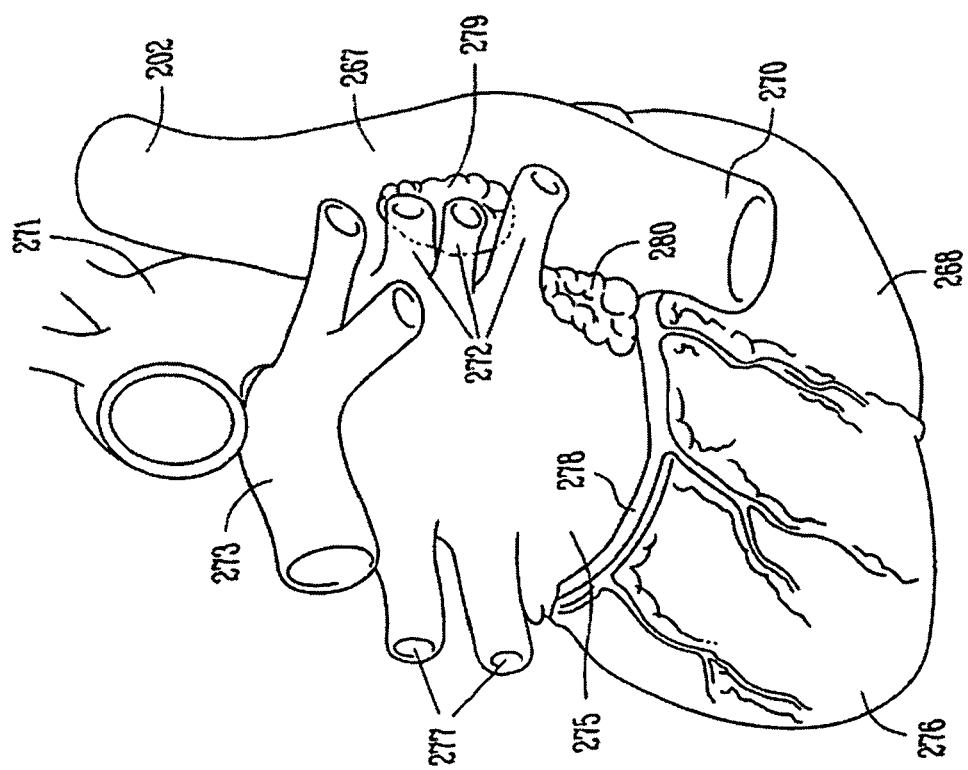

COORDINATED THERAPY FOR DISORDERED BREATHING INCLUDING BAROREFLEX MODULATION

RELATED PATENT DOCUMENTS

The following commonly assigned U.S. patent applications are related, are filed on the same date as the present application, and are all incorporated herein by reference in their respective entireties: U.S. Pat. No. 7,194,313 (Libbus), and U.S. Patent Application Publication No. 2005/0288728.

FIELD OF THE INVENTION

The present invention relates generally to providing therapy for disordered breathing based on modification of the baroreflex response.

BACKGROUND OF THE INVENTION

Disordered breathing refers to a wide spectrum of respiratory conditions that involve disruption of the normal respiratory cycle. Although disordered breathing typically occurs during sleep, the disordered breathing may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Disordered breathing may be classified based on its etiology. One type of disordered breathing, denoted obstructive disordered breathing, occurs when the patient's airway is obstructed by the collapse of soft tissue in the rear of the throat. Central disordered breathing is caused by a derangement of the central nervous system control of respiration. The patient may cease to breathe when control signals from the brain to the respiratory muscles are absent or interrupted. Disordered breathing of mixed origin is a combination of the central and obstructive types.

Apnea is a fairly common form of disordered breathing characterized by periods of interrupted breathing. The cessation of breathing may occur repeatedly during sleep, sometimes hundreds of times a night and sometimes for a minute or longer. In addition to apnea, other types of disordered respiration have been identified, including hypopnea (shallow breathing), tachypnea (rapid breathing), hyperpnea (heavy breathing), dyspnea (labored breathing), and orthopnea (difficulty breathing lying down). Combinations of the disordered respiratory cycles described above may be observed, including, for example, in periodic breathing and Cheyne-Stokes respiration (CSR). Periodic breathing is characterized by cyclic respiratory patterns that may exhibit rhythmic rises and falls in tidal volume. Cheyne-Stokes respiration is a specific form of periodic breathing wherein the tidal volume decreases, resulting in apneic intervals. The breathing interruptions of periodic breathing and CSR may be associated with central apnea, or may be obstructive in nature.

Cheyne-Stokes respiration and other forms of disordered breathing are frequently observed in patients with congestive heart failure (CHF). Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Disordered breathing is associated with an increased risk of accelerated CHF progression.

Effective approaches to treat disordered breathing are needed. The present invention fulfills these and other needs, and addresses other deficiencies of prior art implementations and techniques.

SUMMARY OF THE INVENTION

Various embodiments of present invention involve methods and systems for providing disordered breathing therapy based on modification of the patient's baroreflex response.

In accordance with an embodiment of the invention, a disordered breathing therapy method involves coordinating delivery of a plurality of therapies to treat disordered breathing. At least one of the therapies comprises an electrical stimulation therapy modulating a patient's baroreflex response.

Another embodiment of the invention involves a disordered breathing therapy system including a plurality of therapy devices. Each therapy device is configured to deliver a disordered breathing therapy differing from disordered breathing therapies delivered by the other therapy devices.

At least one of the therapy devices includes one or more electrodes configured to deliver a baroreflex electrical stimulation signal. A baroreflex stimulator is coupled to the baroreflex electrodes and is configured to deliver an electrical stimulation therapy modifying a patient's baroreflex response.

The disordered breathing system also includes a therapy controller coupled to the plurality of therapy devices. The therapy controller coordinates a disordered breathing therapy regimen delivered by the plurality of therapy devices.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 2A-2C are diagrams illustrating a heart;

FIG. 3 illustrates baroreceptors and afferent nerves in the area of the carotid sinuses and aortic arch that may be used in connection with baroreflex therapy for disordered breathing in accordance with embodiments of the invention;

Figure 1B:
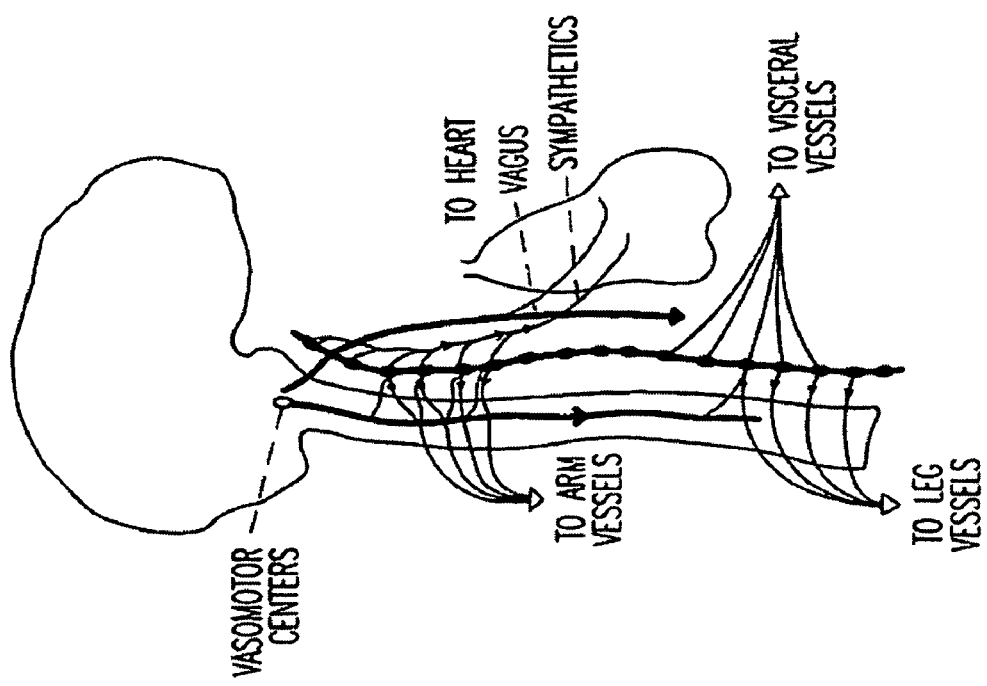
FIGS. 1A and 1B illustrate afferent and efferent nerve systems, respectively, that may be used in connection with baroreflex therapy for disordered breathing in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

A significant percentage of patients between the ages of 30 and 60 years experience some symptoms of disordered breathing. Sleep disordered breathing is associated with excessive daytime sleepiness, systemic hypertension, increased risk of stroke, angina, and myocardial infarction. Disordered breathing is particularly prevalent among congestive heart failure patients, and may contribute to the progression of heart failure.

Breathing is affected by activation of pressoreceptive regions or fields within the body that are capable of sensing changes in pressure. Stimulation of a baroreceptor region modulates a patient's baroreceptor response, causing blood pressure to drop and respiration to become faster and deeper. Respiration and blood pressure appear to return to the pre-stimulated state within a few minutes after the stimulation is removed. Embodiments of the invention are directed to a therapy for disordered breathing based on the relationship between the baroreflex response and respiration. In various examples described below, the baroreflex response may be modified by electrical stimulation of baroreceptor regions, causing changes in respiration that prevent or mitigate episodes of disordered breathing.

Baroreflex is a reflex triggered by stimulation of a baroreceptor. A baroreceptor includes any sensor of pressure changes, such as afferent nerves, sensory nerve endings in the wall of the atria of the heart, vena cava, aortic arch and/or carotid sinus, that is sensitive to stretching. The baroreflex functions as a negative feedback system. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance and causes respiration to become faster and deeper.

Various embodiments of the invention involve an electrical stimulation therapy for modulating the patient's baroreflex response to treat disordered breathing. For example, the baroreflex response may be modulated by stimulation of baroreceptor sites in the pulmonary artery, by stimulation of baroreceptor sites and/or nerve endings in the aorta, chambers of the heart, and/or by stimulation of the vagus, carotid, and/or aortic nerves.

Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

The baroreflex response may be modulated by stimulation of the cardiac fat pads. The cardiac fat pads contain parasympathetic ganglia. These ganglia selectively innervate different regions of cardiac tissue. Electrical stimulation of the cardiac fat pads serves to stimulate the baroreflex response through efferent stimulation. The fat pads may be electrically stimulated using an electrode screwed into the fat pad, for example.

The subject matter of this disclosure involves relationships between the automatic nervous system (ANS) and respiration. The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Blood pressure and respiration rate are affected when the sympathetic nervous system is triggered. Blood pressure increases and respiration rate decreases when the sympathetic nervous system is triggered. Blood pressure decreases and respiration rate increases and when the sympathetic nervous system is inhibited (the parasympathetic nervous system is stimulated).

Figure 1A:
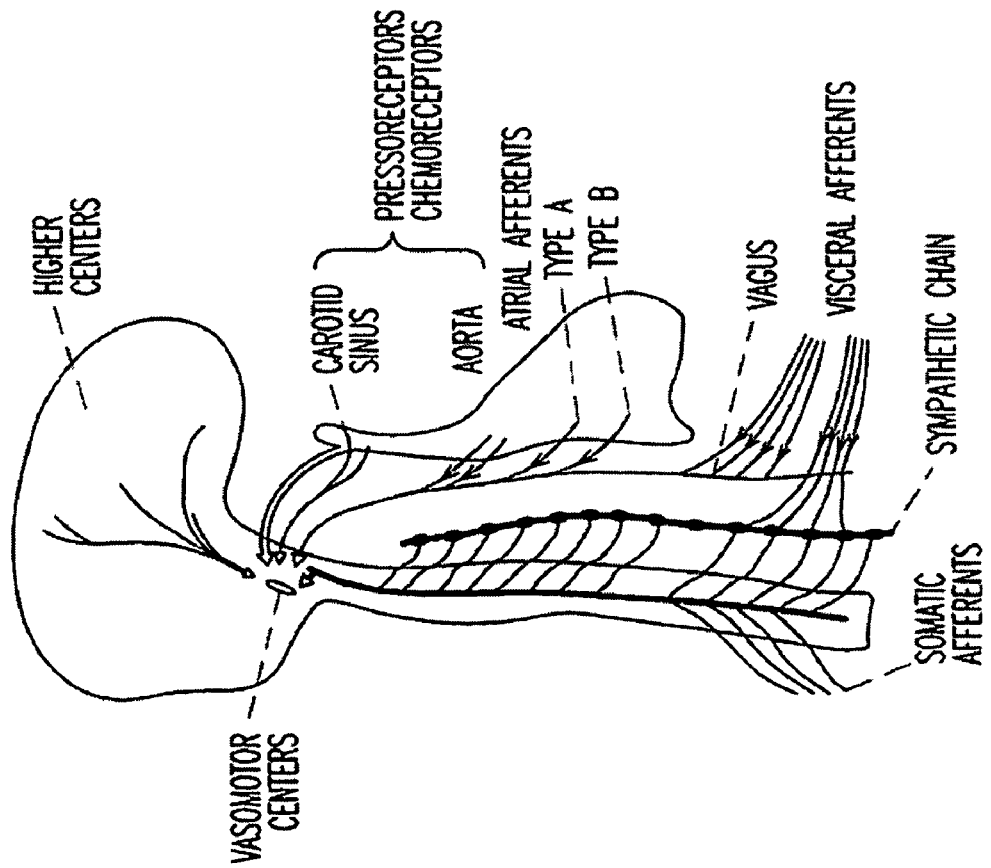

FIGS. 1A and 1B illustrate neural mechanisms that control the respiration phenomena described above. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than modification of respiration rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as modification of respiration, in one physiological system may result in an undesired response in other physiological systems.

Figure 2B:
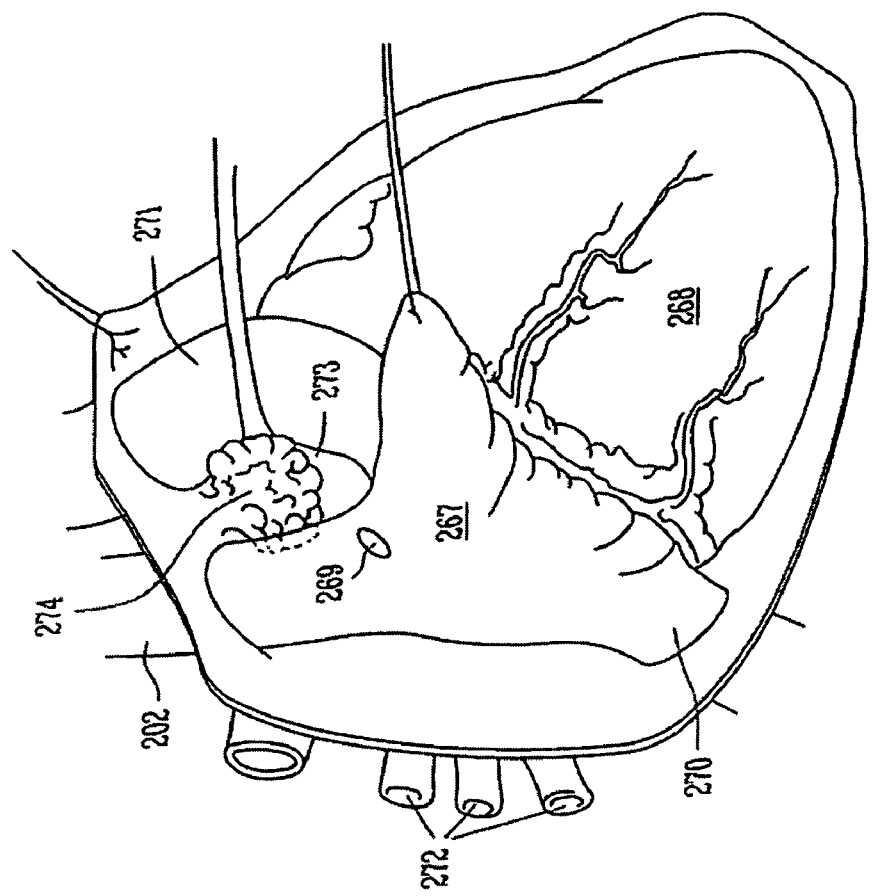
Figure 2A:
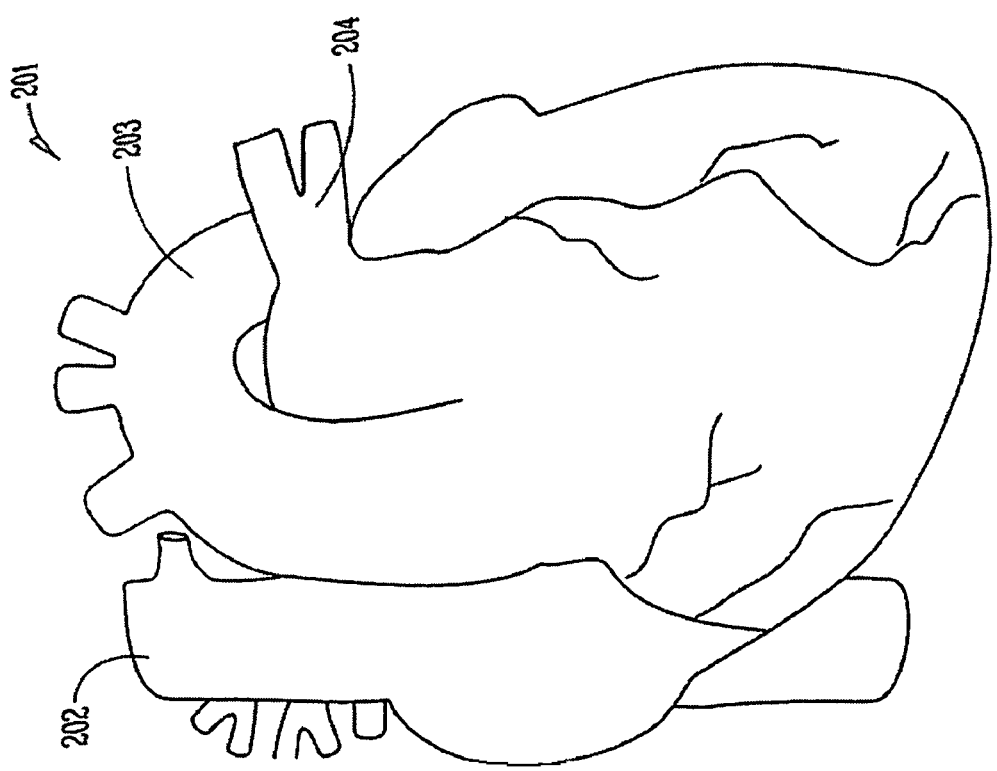

FIGS. 2A-2C illustrate a heart. As illustrated in FIG. 2A, the heart 201 includes a superior vena cava 202, an aortic arch 203, and a pulmonary artery 204. As is discussed in more detail below, the pulmonary artery 204 includes baroreceptor regions. A lead, similar to a cardiac pacemaker lead, can be intravascularly inserted through a peripheral vein and through the tricuspid valve into the right ventricle of the heart (not expressly shown in the figure) continuing from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the invention, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof.

FIGS. 2B-2C illustrate the right side and left side of the heart, respectively, and further illustrate cardiac fat pads which may be utilized in connection with stimulation of the baroreflex response. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Parasympathetic ganglia in the cardiac fat pad 274 are stimulated in some embodiments using an electrode screwed into the fat pad. Stimulation of the parasympathetic ganglia of the fat pad may be used to modulate the baroreflex response. The fat pad may be stimulated using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins 272 and a cardiac fat pad 280 located proximate to the inferior vena cava 270 and left atrium 275.

Parasympathetic ganglia in the fat pad 279 are stimulated in some embodiments using an electrode screwed into the fat pad 279, and are stimulated in some embodiments using an intravenously-fed lead proximately positioned to the fat pad in a vessel such as the right pulmonary artery 273 or right pulmonary vein 272, for example. Parasympathetic ganglia in the cardiac fat pad 280 are stimulated in some embodiments using an electrode screwed into the fat pad, and are stimulated in some embodiments using an intravenously-fed lead proximately positioned to the fat pad in a vessel such as the inferior vena cava 270 or coronary sinus or a lead in the left atrium 275, for example.

FIG. 3 illustrates baroreceptors in the area of the carotid sinuses 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305, and in the common carotid artery 310. The glossopharyngeal nerve 308 provides nerve endings 309 that function as baroreceptors in the carotid sinus 305. Cuffs may be placed around afferent nerve trunks, such as the vagal nerve, leading from baroreceptors to vasomotor centers to facilitate stimulation of the baroreflex. According to various embodiments of the invention, afferent nerve trunks can be stimulated using a cuff or intravascularly-fed lead positioned in a blood vessel proximate to the afferent nerves.

Figure 4:
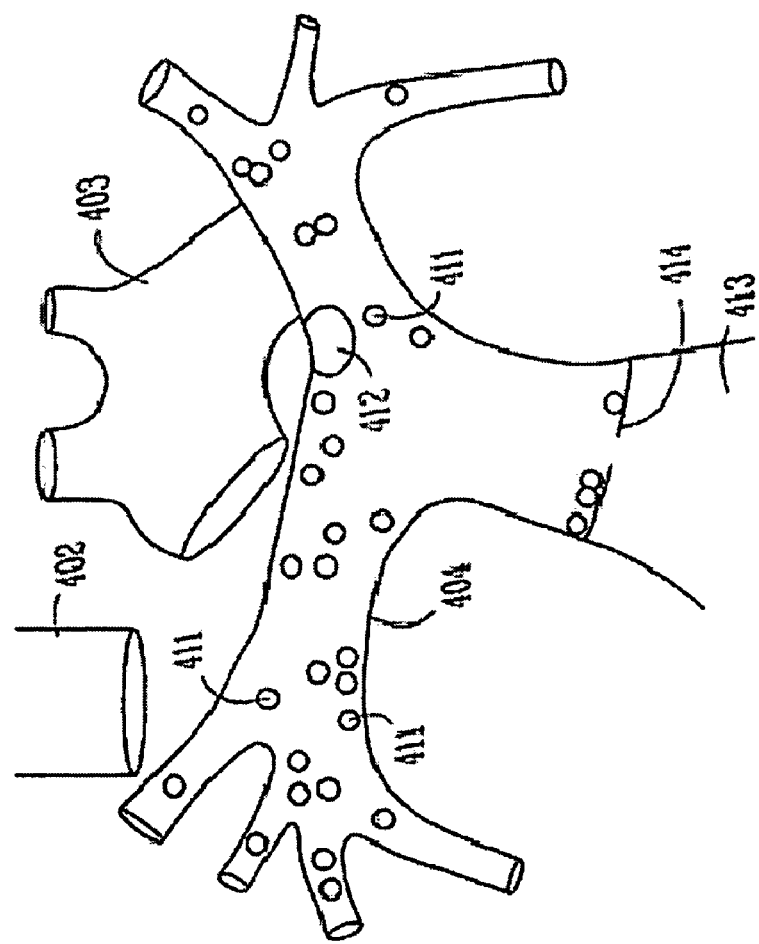
FIG. 4 illustrates baroreceptors in and around the pulmonary artery that may be used in connection with baroreflex therapy for disordered breathing in accordance with embodiments of the invention.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments, a lead may be inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412.

Figure 5:
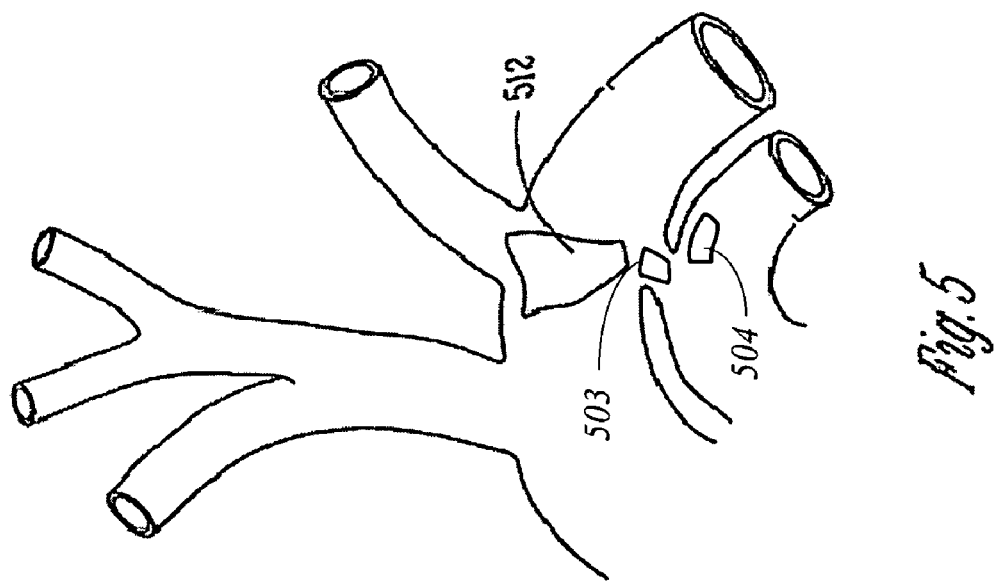
FIG. 5 illustrates baroreceptor fields in the aortic arch, the ligamentum arteriosum, and the trunk of the pulmonary artery that may be used in connection with baroreflex therapy for disordered breathing in accordance with embodiments of the invention.

FIG. 5 illustrates baroreceptor sites in the aortic arch 512, near the ligamentum arteriosum 503, and baroreceptor sites 504 near the trunk of the pulmonary artery. Some embodiments position the lead in the pulmonary artery to stimulate the aorta and/or fat pads, such as are illustrated in FIGS. 2B-2C.

Figure 6:
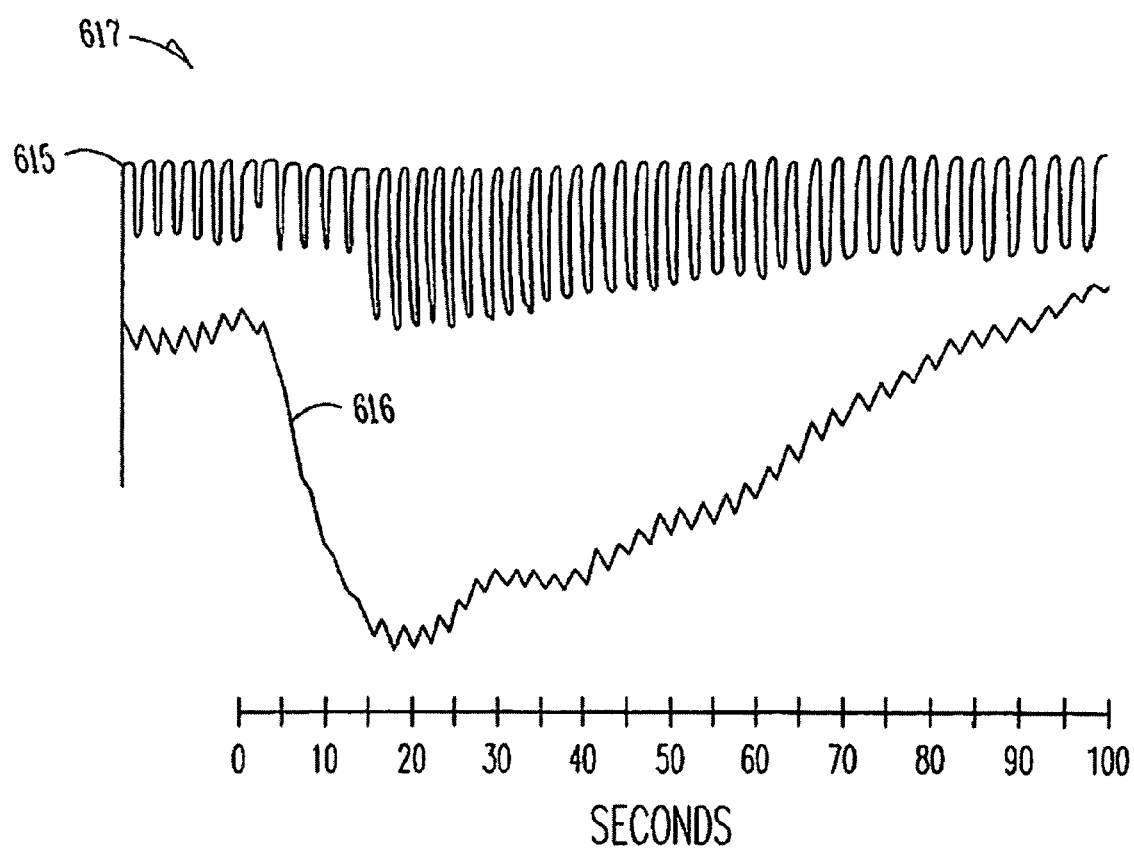
FIG. 6 illustrates a relationship between respiration and blood pressure when the baroreflex is stimulated that may be utilized in connection with disordered breathing therapy in accordance with embodiments of the invention.

FIG. 6 illustrates a relationship 617 between respiration 615 and blood pressure 616 when a baroreflex response is modified by stimulation of a baroreceptor. When the baroreceptor is stimulated, the blood pressure 616 drops, and the respiration 615 becomes faster and deeper, as illustrated by the higher frequency and amplitude of the respiration waveform 615. The respiration and blood pressure appear to return to the pre-stimulated state in approximately one to two minutes after the stimulation is removed. Embodiments of the invention involve methods and systems for modifying a baroreflex response to alter respiration and thereby treat disordered breathing.

Figure 7A:
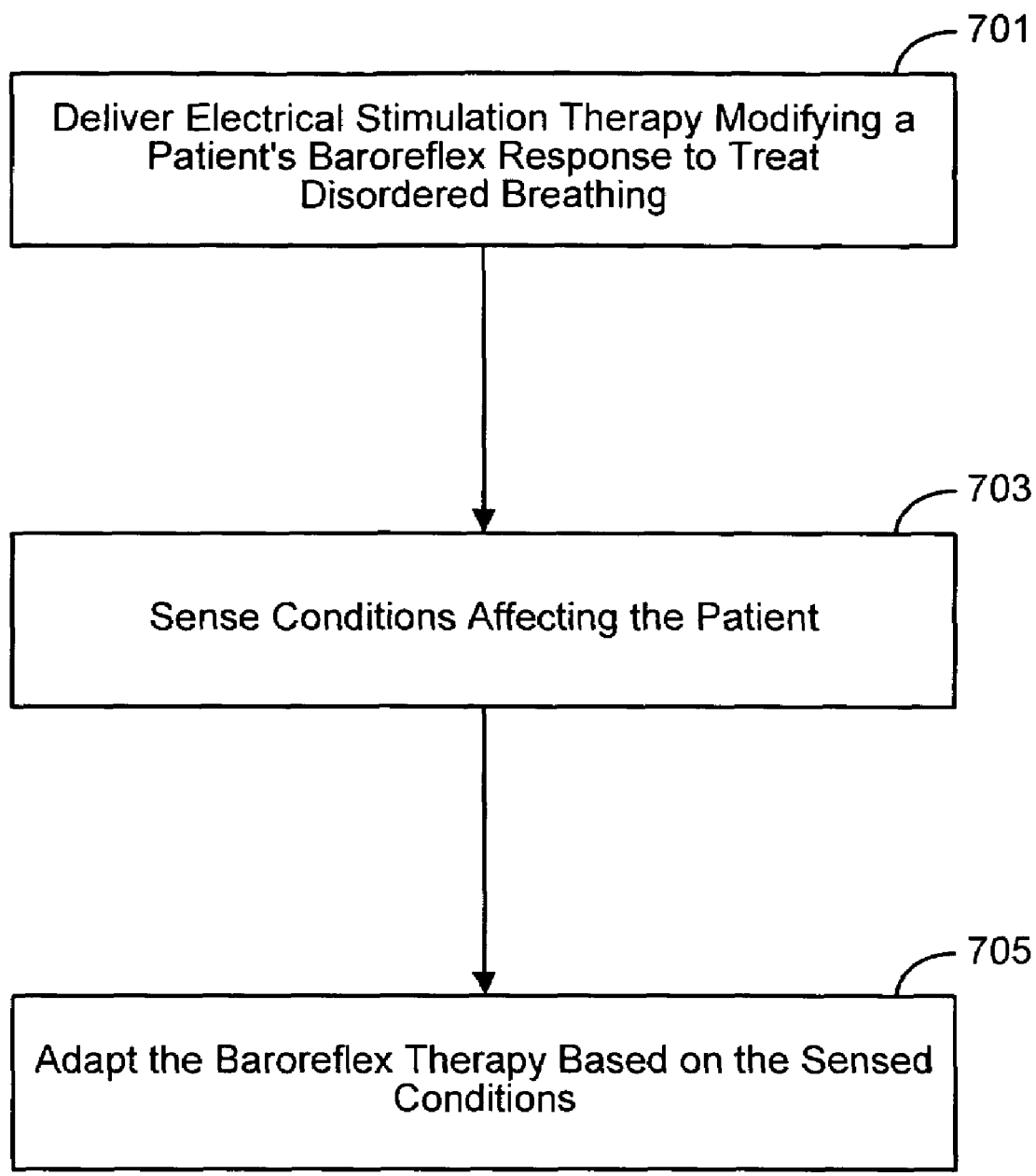
FIGS. 7A and 7B are flowcharts illustrating methods of treating disordered breathing in accordance with embodiments of the invention.

FIG. 7A is a flowchart of a method of delivering disordered breathing therapy in accordance with embodiments of the invention. The method involves delivering 701 electrical stimulation therapy modifying a patient's baroreflex response to treat disordered breathing. One or more conditions affecting the patient are sensed 703. The therapy is adapted 705 based on the sensed conditions.

Sensing the conditions affecting the patient may involve sensing physiological conditions and/or non-physiological conditions. In some embodiments, the sensed conditions may be used to detect disordered breathing and/or to predict occurrences of disordered breathing. The therapy is adapted based on detected and/or predicted occurrences of disordered breathing. Adapting the electrical stimulation therapy modifying the patient's baroreceptor response may involve initiating electrical stimulation to baroreceptor regions, increasing the electrical stimulation, decreasing the electrical stimulation, and/or terminating the electrical stimulation.

In some embodiments, the sensed conditions may be used to determine efficacy of the therapy and/or impact of the therapy on the patient. The therapy may be modified to adjust therapy efficacy and/or patient impact. In one scenario, the electrical stimulation may be modified to enhance therapy efficacy. In another scenario, the electrical stimulation may be modified to reduce an impact of the therapy on the patient. In some implementations, a therapy other than disordered breathing therapy, e.g., anti-hypertensive therapy (AHT), or other therapies, may be delivered to the patient that also involves electrical stimulation of the baroreceptors. In this scenario, therapy for disordered breathing may involve withholding electrical stimulation.

Therapy for disordered breathing may be enhanced by coordinated use of a number of different types of therapy. For example, disordered breathing may be treated as described herein through modification of the patient's baroreflex response through electrical stimulation. Other methodologies for treating disordered breathing may also be implemented. For example, cardiac electrical stimulation, e.g., cardiac pacing or sub-capture threshold electrical stimulation, may be used to treat disordered breathing. In one approach, overdrive pacing of one or more heart chambers may be beneficial in the treatment of disordered breathing.

Nerve and muscle stimulation devices have also been used to provide therapy for disordered breathing. Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal (HG) nerve innervates the protrusor and retractor tongue muscles. An appropriately applied electrical stimulation to the hypoglossal nerve, for example, may prevent backward movement of the tongue, thus preventing the tongue from obstructing the airway.

Central sleep apnea may also be treated by phrenic nerve pacing, also referred to as diaphragmatic pacing. Phrenic nerve pacing uses an electrode implanted in the chest to stimulate the phrenic nerve. The phrenic nerve is generally known as the motor nerve of the diaphragm. It runs through the thorax, along the heart, and then to the diaphragm. Diaphragmatic pacing is the use of electronic stimulation of the phrenic nerve to control the patient's diaphragm and induce a respiratory cycle. Pacing the phrenic nerve may be accomplished by surgically placing a nerve cuff on the phrenic nerve, and then delivering an electric stimulus. The electric stimulus of the phrenic nerve then causes the diaphragm to induce a respiratory cycle.

External respiratory therapies such as positive airway pressure therapy have been used to treat disordered breathing. The positive airway pressure device develops a positive airway pressure that is delivered to the patient's airway through tubing and a mask. The positive airway pressure provided by the device acts as a pneumatic splint keeping the patient's airway open and reducing the severity and/or number of occurrences of disordered breathing due to airway obstruction.

Figure 7B:
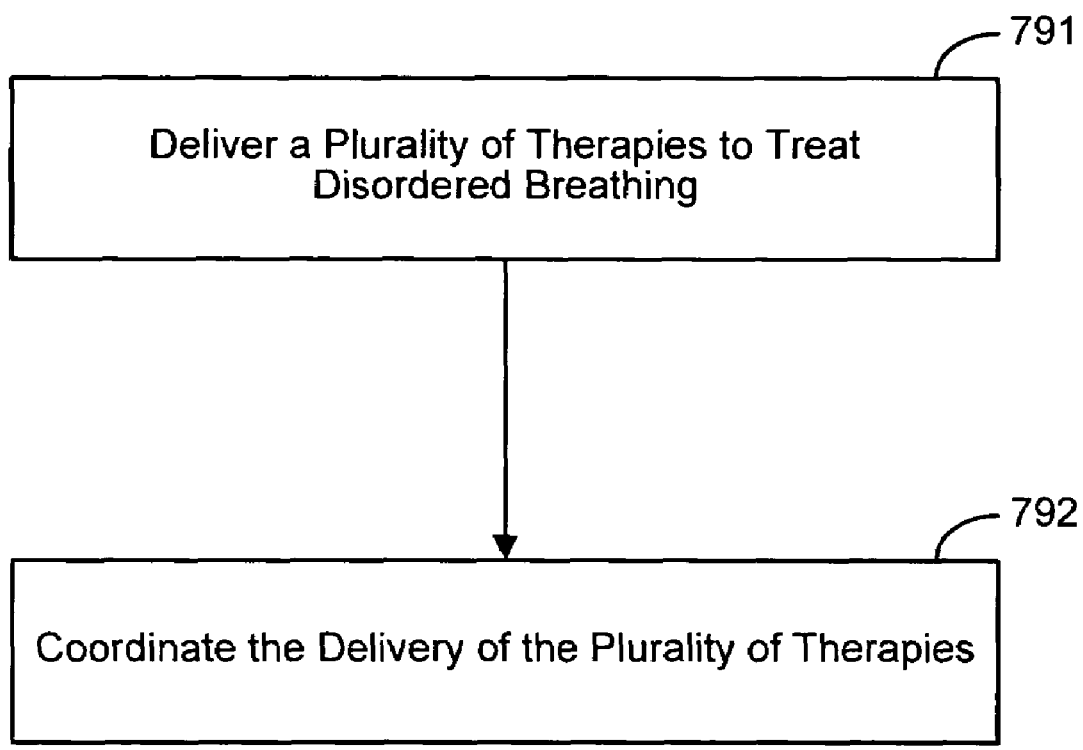

Various therapies, including baroreflex modulation, may be used cooperatively to treat disordered breathing, as illustrated in the flowchart of FIG. 7B. A plurality of therapies is delivered 791 to the patient, including at least an electrical stimulation therapy modulating the patient's baroreflex response. The method includes coordinating 792 the delivery of the plurality of therapies. The plurality of therapies may include one or more of external respiratory therapy, nerve stimulation therapy, muscle stimulation therapy, cardiac electrical stimulation therapy, and/or other types of therapies in addition to the therapy to modulate the patient's baroreflex response.

Delivery of the plurality of therapies may be coordinated to achieve various therapeutic goals, e.g., to enhance overall therapy efficacy, to reduce impact to the patient, to avoid therapy interactions, among others. According to one aspect of the invention, coordination of therapies may include shifting the therapy burden from one type of therapy to another type of therapy in response to events or conditions. According to another aspect, coordination of therapies may involve using one type of therapy to treat one type of disordered breathing, and using another type of therapy to treat another type of disordered breathing.

Figure 7C:
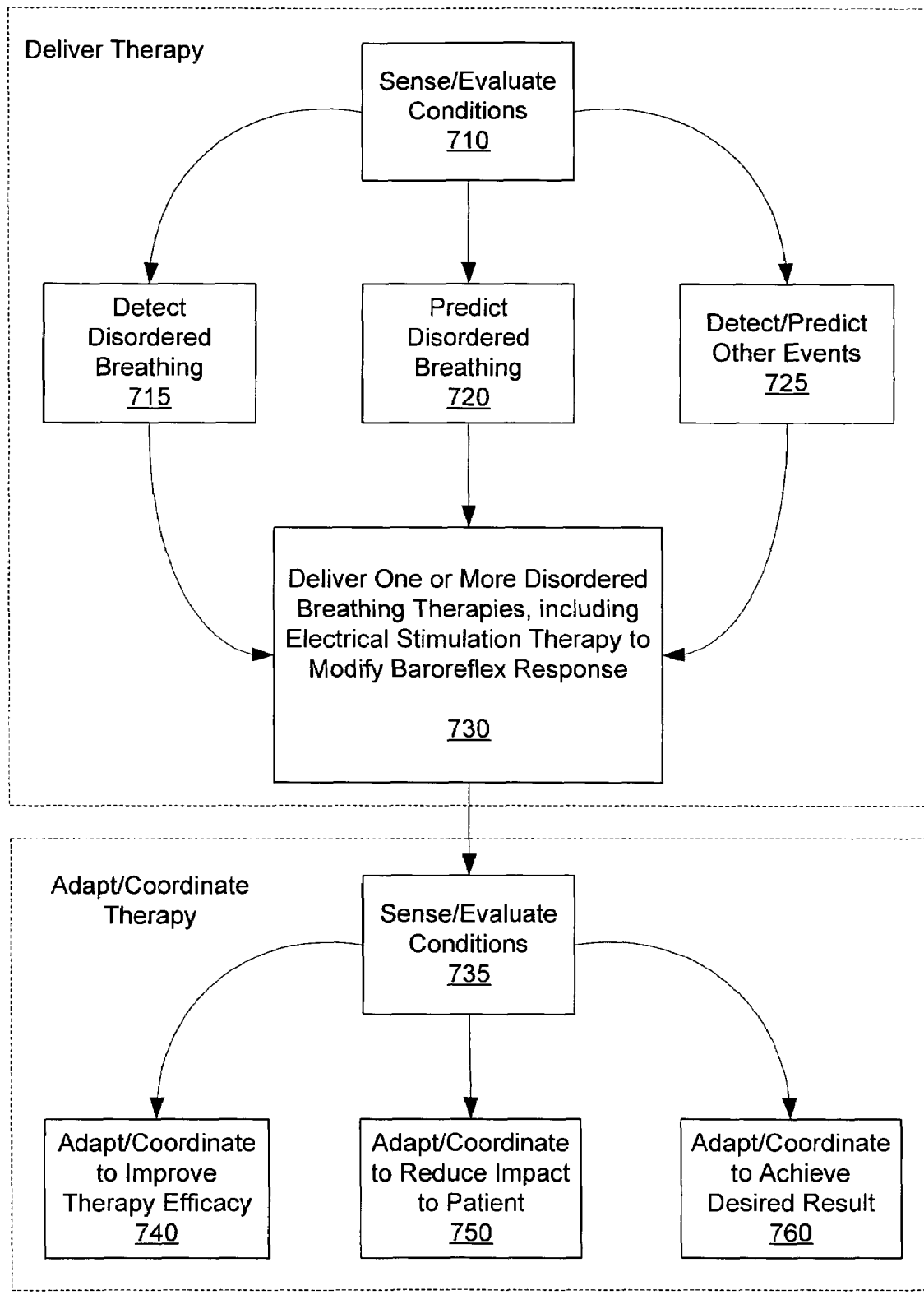
FIG. 7C is a process flow diagram illustrating modification of the baroreflex to treat disordered breathing in accordance with embodiments of the invention.

FIG. 7C is a process flow diagram illustrating various approaches for delivering therapy to treat disordered breathing including modification of the baroreflex response. According to one aspect of the invention, modification of the baroreflex response may be implemented by delivering an electrical stimulation to one or more regions that will stimulate the baroreflex response. The stimulation of the baroreflex response causes respiration to become faster and deeper, thus preventing, reducing, or terminating disordered breathing episodes.

In some embodiments, the therapy to treat disordered breathing may involve only electrical stimulation for baroreflex modulation. In other embodiments, the therapy to treat disordered breathing may involve a plurality of therapies, i.e., a plurality of different therapy types, including at least electrical stimulation for baroreflex modulation.

In some implementations, the therapy may be delivered responsive to various detected or predicted events 715, 720, 725. For example, therapy may be delivered responsive to detection of disordered breathing 715, prediction of disordered breathing 720, detection of sleep 725, or other events. Detection or prediction of the event may be accomplished by sensing and evaluating 710 one or more conditions affecting the patient that are indicative or predictive of the event. In one example, the therapy may be delivered 730 responsive to the detection 715 of a disordered breathing episode. Conditions indicative of disordered breathing include conditions such as blood oxygen level, respiration pattern, tidal volume, and/or other conditions. In another example, the therapy may be delivered 730 responsive to the prediction 720 of disordered breathing. In yet another example, the therapy may be delivered responsive to detection 725 that the patient is asleep, or during the patient's normal sleep time.

The therapy may be adapted and/or coordinated 740, 750, 760 to achieve or approach a desired outcome. For example, the therapy may be modified to improve therapy efficacy 740, to reduce an impact to the patient 750, and/or to achieve or approach another desired result 760, such as reduction or avoidance of therapy interactions. Adaptation and/or coordination of the therapy 740, 750, 760 may be based on one or more sensed conditions 735.

Figure 8:
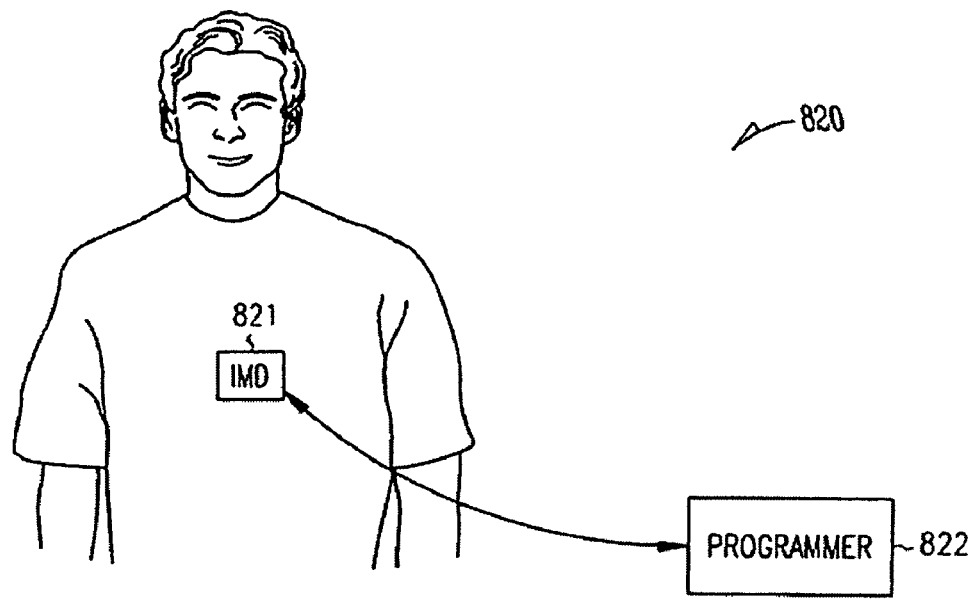
FIG. 8 illustrates a system that includes an implantable medical device for stimulating the baroreflex for disordered breathing therapy in accordance with embodiments of the invention.

A baroreflex stimulation system that may be used in connection with the processes outlined in FIGS. 7A-7C is illustrated in FIG. 8. Such baroreflex stimulation systems are also referred to herein as neural stimulator (NS) devices or components. Baroreflex stimulation systems for treatment of disordered breathing may be used alone or in combination with other therapy devices used to treat disordered breathing or to provide other monitoring, diagnostic, and/or therapeutic functions. Examples illustrated herein involve systems that include a baroreceptor stimulator device and one or both of a cardiac pacing/sensing device and an external respiratory therapy device. The devices may be capable of communicating with each other either through wired or wireless communication links. Coordinating monitoring, diagnosis, and/or therapy functions of the devices allows these functions to operate more intelligently. In some examples, circuitry for implementing two or more types of disordered breathing therapy may be disposed within a single device housing.

FIG. 8 illustrates a system 820 including an implantable medical device (IMD) 821 and a programmer 822. The IMD 821 may include neural stimulator functions only, or may include a combination of neural stimulator functions and cardiac pacing and/or sensing functions. Some embodiments of the NS may provide disordered breathing therapy. Some embodiments of the neural stimulator may have the capability to provide anti-hypertensive therapy (AHT) as well as disordered breathing therapy.

Some embodiments of the cardiac pacing/sensing device may have the capability to provide cardiac stimulation therapy, such as bradycardia pacing, cardiac resynchronization pacing, and/or cardioversion/defibrillation shocks. Some embodiments of the cardiac stimulation/sensing (CSS) device may provide cardiac electrical stimulation therapy for disordered breathing. The CSS device may provide both cardiac electrical stimulation for disordered breathing and one or more of the cardiac rhythm management therapies outlined above. The programmer 822 and the IMD 821 are capable of wirelessly communicating data and instructions. In various embodiments, for example, the programmer 822 and IMD 821 use telemetry coils to wirelessly communicate data and instructions.

Thus, the programmer can be used to adjust the programmed therapy provided by the IMD 821, and the IMD 821 can report device data (such as battery and lead resistance) and therapy data (such as sense and stimulation data) to the programmer using radio telemetry, for example. According to various embodiments, the IMD 821 stimulates baroreceptors to provide disordered breathing therapy. Various embodiments of the IMD 821 stimulate baroreceptors in the pulmonary artery using a lead fed through the right ventricle similar to a cardiac pacemaker lead, and further fed into the pulmonary artery. According to various embodiments, the IMD 821 includes one or more sensors to sense various conditions associated with disordered breathing or disordered breathing therapy. Information acquired from the one or more sensors can be used to perform feedback in a closed loop control system.

Figure 9:
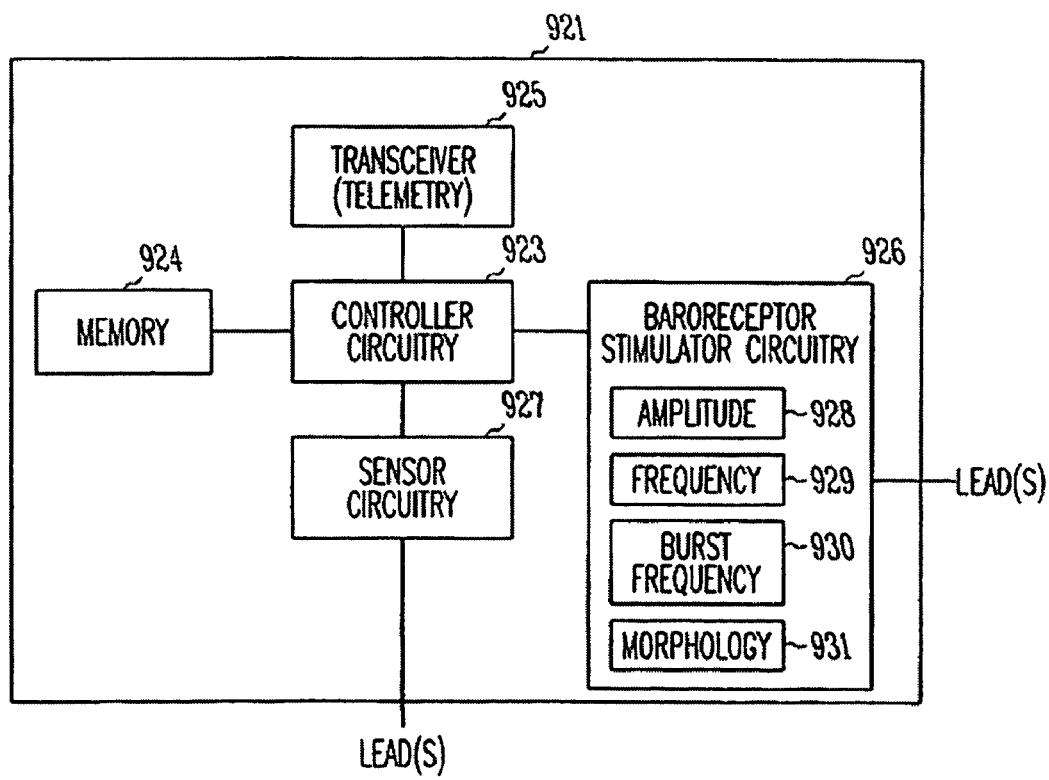
FIG. 9 illustrates a block diagram of a neural stimulation device in accordance with embodiments of the invention.

FIG. 9 illustrates an implantable medical device (IMD) 921 such as the IMD 821 shown in the system 820 of FIG. 8, according to various embodiments of the invention. The illustrated IMD 921 performs NS functions to provide disordered breathing therapy. The illustrated device 921 includes baroreceptor stimulation circuitry 926. Various embodiments of the device 921 also include sensor circuitry 927. The illustrated device 921 includes controller circuitry 923 and a memory 924. The controller circuitry 923 is capable of being implemented using hardware, software, and combinations of hardware and software. According to various embodiments, the controller circuitry 923 includes a processor to perform instructions embedded in the memory 924 to perform functions associated with disordered breathing therapy. For example, the illustrated device 921 further includes a transceiver 925 and associated circuitry for communication with a programmer and/or another patient-external or patient-internal device. Various embodiments have wireless communication capabilities. For example, some transceiver embodiments use a telemetry coil to wirelessly communicate with a programmer or another external or internal device.

One or more leads are able to be connected to the sensor circuitry 927 and baroreceptor stimulation circuitry 926. The baroreceptor stimulation circuitry 926 is used to apply electrical stimulation pulses to desired baroreceptors sites, such as baroreceptor sites in the pulmonary artery, or other locations, through one or more stimulation electrodes. The sensor circuitry 927 is used to detect various conditions, such as conditions related to disordered breathing and/or disordered breathing therapy.

According to various embodiments, the stimulator circuitry 926 includes modules to set any one or any combination of two or more of the following pulse features: the amplitude 928 of the stimulation pulse, the frequency 929 of the stimulation pulse, the burst pattern 930 or duty cycle of the pulse, and the wave morphology 931 of the pulse. Examples of wave morphology include a square wave, triangle wave, sinusoidal wave, and waves with desired harmonic components to mimic white noise such as is indicative of naturally-occurring baroreflex stimulation.

Figure 10A:
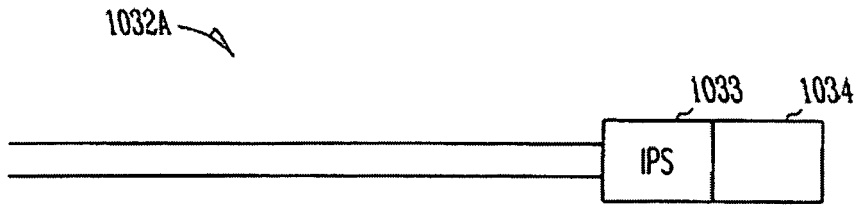
FIGS. 10A-10C illustrate a baroreceptor stimulation lead having an integrated pressure sensor in accordance with embodiments of the invention.
Figure 10B:
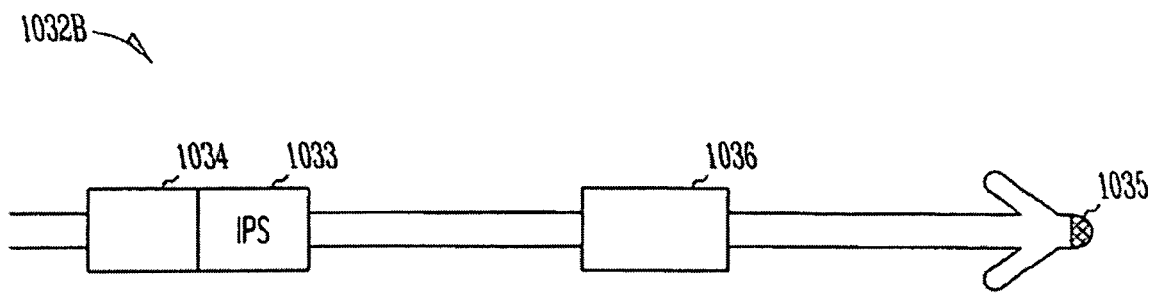
Figure 10C:
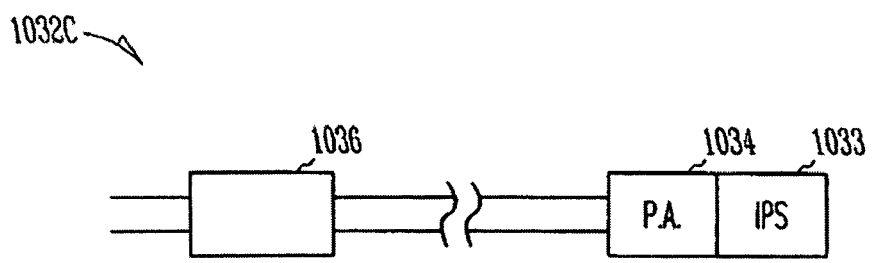

FIGS. 10A-10C illustrate a baroreceptor stimulation lead having an integrated pressure sensor (IPS), according to various embodiments of the present subject matter. Although not drawn to scale, these illustrated leads 1032A, 1032B and 1032C include a baroreceptor stimulator electrode 1034 and an IPS 1033 to monitor changes in blood pressure. Changes in blood pressure may be used control baroreceptor stimulation. These lead illustrations should not be read as limiting other aspects and embodiments of the present subject matter. In various embodiments, for example, micro-electrical mechanical systems (MEMS) technology is used to sense the blood pressure. Some sensor embodiments determine blood pressure based on a displacement of a membrane.

The embodiments of the lead illustrated in FIGS. 10A-10C involve a lead including a stimulation electrode and a sensor. Alternatively, separate leads could be used for the stimulator and sensor. Some implementations may involve using a stimulator alone without a sensor. These implementations may use a lead having only a stimulator.

FIGS. 10A-10C illustrate an IPS on a lead. Some embodiments implant an IPS in an IMD or NS device. The stimulator and sensor functions can be integrated, even if the stimulator and sensors are located in separate leads or positions.

The lead 1032A illustrated in FIG. 10A includes a distally-positioned baroreceptor stimulator electrode 1034 and an IPS 1033. This lead, for example, is capable of being intravascularly introduced to stimulate a baroreceptor site, such as the sites in the pulmonary artery, aortic arch, ligamentum arteriosum, the coronary sinus, in the atrial and ventricular chambers, and/or in cardiac fat pads.

The lead 1032B illustrated in FIG. 10B includes a tip electrode 1035, a first ring electrode 1036, second ring electrode 1034, and an IPS 1033. This lead may be intravascularly inserted into or proximate to chambers of the heart and further positioned proximate to baroreceptor sites such that at least some of the electrodes 1035, 1036 and 1034 are capable of being used to pace or otherwise stimulate the heart, and at least some of the electrodes are capable of stimulating at least one baroreceptor site. The IPS 1033 is used to sense blood pressure. In various embodiments, the IPS is used to sense the blood pressure in the vessel proximate to the baroreceptor site selected for stimulation.

The lead 1032C illustrated in FIG. 10C includes a distally-positioned baroreceptor stimulator electrode 1034, an IPS 1033 and a ring electrode 1036. This lead 1032C may be intravascularly inserted into the right atrium and ventricle, and then through the pulmonary valve into the pulmonary artery. Depending on programming in the device, the electrode 1036 can be used to pace and/or sense cardiac activity, such as that which may occur within the right ventricle, and the electrode 1034 and IPS 1033 are located near baroreceptors in or near the pulmonary artery to stimulate and sense, either directly or indirectly through surrogate parameters, baroreflex activity.

Thus, various embodiments of the present subject matter provide an implantable NS device that automatically modulates baroreceptor stimulation using an IPS. Integrating the pressure sensor into the lead provides localized feedback for the stimulation. This localized sensing improves feedback control. According to various embodiments, the device monitors pressure parameters such as mean arterial pressure, systolic pressure, diastolic pressure and the like. The device may use one or more of the pressure parameters as a surrogate for respiration to control disordered breathing therapy. For example, if disordered breathing is detected or predicted, the device may initiate stimulation of baroreceptors to increase respiration. As mean arterial pressure tends toward a lower pressure limit, the device may respond by reducing the baroreceptor stimulation. In various embodiments, the algorithm may take into account the current metabolic state (cardiac demand) and adjust neural stimulation accordingly. A NS device having an IPS is able to use blood pressure as a feedback signal. With feedback, the NS device is able to automatically modulate baroreceptor stimulation based on the sensed pressure, allowing the NS device to deliver the appropriate level of therapy without causing the patient's blood pressure to drop below a desired limit. Other sensors, such as a transthoracic impedance sensor, blood oxygen sensor, and/or other types of sensors may be additionally or alternatively used to provide feedback control. Sensors used for feedback control may or may not reside in the NS device.

Figure 11A:
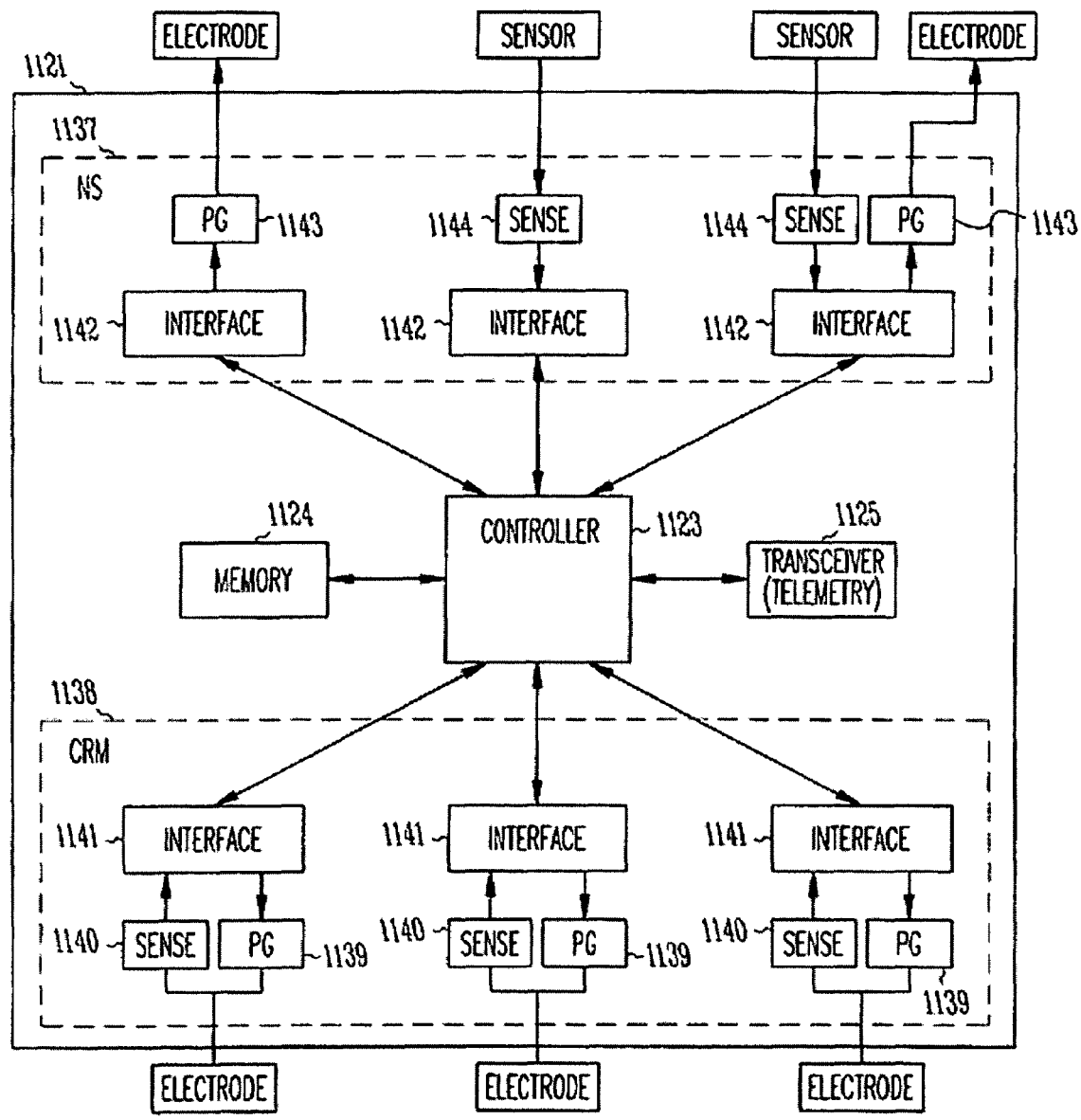
FIG. 11A illustrates a block diagram of an implantable medical device including a baroreflex stimulation device and a cardiac stimulating and/or sensing device in accordance with embodiments of the invention.

FIG. 11 illustrates an implantable medical device (IMD) 1121 as shown at 821 in FIG. 8 having an NS component 1137 and cardiac pacing and/or sensing component 1138, according to various embodiments. The illustrated device 1121 includes a controller 1123 and a memory 1124. According to various embodiments, the controller 1123 includes hardware, software, or a combination of hardware and software to perform the baroreceptor stimulation and cardiac pacing/sensing functions. For example, the programmed therapy applications discussed in this disclosure are capable of being stored as computer-readable instructions embodied in memory and executed by a processor. According to various embodiments, the controller 1123 includes a processor to execute instructions embedded in memory to perform the baroreceptor stimulation and cardiac pacing and/or sensing functions. The illustrated device 1121 further includes a transceiver and associated circuitry for use to communicate with a programmer or another external or internal device. Various embodiments include a telemetry coil.

The cardiac pacing/sensing section 1138 includes components, under the control of the controller, to stimulate a heart and/or sense cardiac signals using one or more electrodes. The cardiac pacing/sensing section 1138 may include a pulse generator 1139 to provide an electrical signal through an electrode to stimulate one or more chambers of the heart and/or to stimulate multiple sites in one or more chambers. The cardiac pacing/sensing section 1138 may include sense circuitry 1140 to detect and process sensed cardiac signals. In various embodiments, the cardiac pacing and/or sensing may be performed in one or more of a right ventricle, left ventricle, right atrium, and left atrium. An interface 1141 can be used to communicate between the controller 1123 and the pulse generator 1139 and sense circuitry 1140. Three electrodes are illustrated as an example for use to provide cardiac pacing and/or sensing functionality. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1137 includes components, under the control of the controller, to stimulate a baroreceptor and/or sense conditions associated with disordered breathing and/or disordered breathing therapy such as respiration, blood pressure, nerve activity, and the like. Three interfaces 1142 are illustrated for use to provide disordered breathing therapy. However, the present subject matter is not limited to a particular number of interfaces, or to any particular stimulating or sensing functions. Pulse generators 1143 are used to provide electrical pulses to an electrode to stimulate a baroreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1144 are used to detect and process signals from a sensor, such as a sensor of nerve activity, blood pressure, respiration, and the like. The interfaces 1142 facilitate communication between the controller 1123 and the pulse generator 1143 and sense circuitry 1144. Each interface, for example, may be used to control a separate lead. Various embodiments of the NS therapy section only include a pulse generator to stimulate baroreceptors. Other embodiments include a pulse generator and one or more sensors.

An embodiment of the invention involves a chronically-implanted stimulation system specially designed to treat disordered breathing by stimulating baroreceptors. Stimulation of the baroreceptors activates the baroreceptor reflex, causing an increase in respiration rate and/or volume. Baroreceptors are located in various anatomical locations such as the carotid sinus and the aortic arch. Other baroreceptor locations include the pulmonary artery, including the ligamentum arteriosum, and sites in the atrial and ventricular chambers. In various embodiments, the system is integrated into a pacemaker/defibrillator or other electrical stimulator system. Components of the baroreflex modulation system include a pulse generator, sensors to monitor various patient conditions pertinent to disordered breathing therapy, leads to apply electrical stimulation to baroreceptors, algorithms to determine the appropriate time to administer stimulation, and algorithms to manipulate data for display and patient management.

Various embodiments combine a "stand-alone" pulse generator with a minimally invasive, unipolar lead that directly stimulates baroreceptors in the vicinity of the heart, such as in the pulmonary artery. Various embodiments incorporate an implanted system that can sense one or more parameters related to disordered breathing and/or disordered breathing therapy. This system adjusts the electrical stimulation output (waveform amplitude, frequency, etc.) to achieve or approach one or more therapeutic goals, such as a desired sleep quality, impact to the patient and/or a level of therapy efficacy. In various embodiments, an implanted system includes a pulse generating device and lead system, the stimulating electrode of which is positioned near endocardial baroreceptor tissues using transvenous implant technique(s).

Another embodiment includes a system that combines NS therapy with cardiac electrical stimulation therapy. Cardiac electrical stimulation therapy may be delivered to treat disordered breathing and/or to provide cardiac rhythm management. Cardiac rhythm management therapies may include one or more of bradyarrhythmia, tachyarrhythmia, and/or congestive heart failure (CHF) therapies. Some embodiments use an additional "baroreceptor lead" that emerges from the header of an implantable device. Electrical stimulation to baroreceptor sites is delivered though the lead using a pulse generating system adapted for baroreceptor stimulation. In another embodiment, a traditional cardiac lead is dimensioned to incorporate proximal electrodes positioned near baroreceptor sites. With these leads, distal electrodes provide cardiac electrical stimulation therapy and proximate electrodes stimulate baroreceptors.

According to various embodiments, the lead(s) and the electrode(s) on the leads are physically arranged with respect to the heart in a fashion that enables the electrodes to properly transmit pulses and sense signals from the heart, and with respect to baroreceptors to stimulate the baroreflex. As there may be a number of leads and a number of electrodes per lead, the configuration can be programmed to use a particular electrode or electrodes.

Figure 11B:
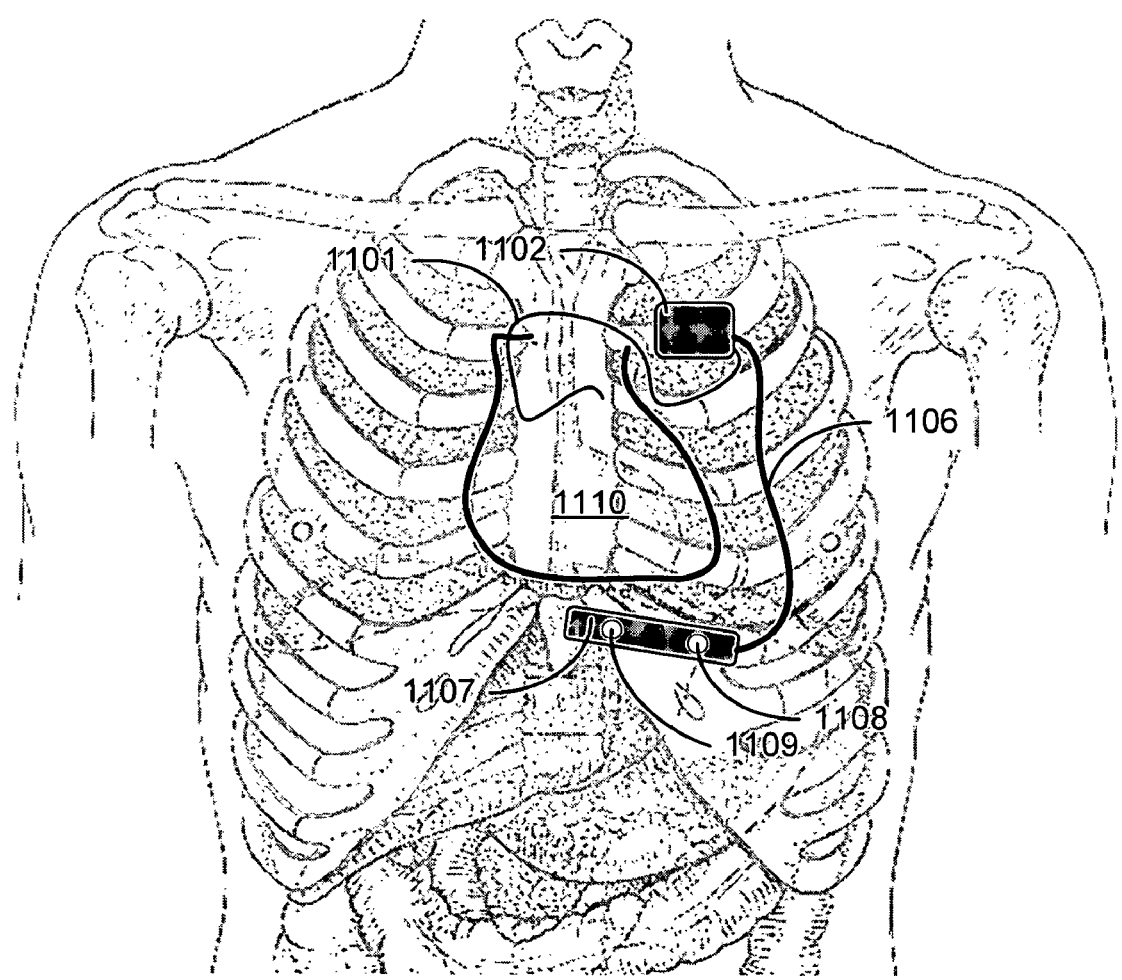
FIG. 11B is a diagram illustrating an implantable transthoracic cardiac stimulating and/or sensing device that may be used in connection with disordered breathing therapy in accordance with embodiments of the invention.

Another embodiment involves the use of an implantable transthoracic cardiac sensing and/or stimulation device, as illustrated in FIG. 11B. FIG. 11B is a diagram illustrating an implantable transthoracic cardiac sensing and/or stimulation device that may be used in connection baroreceptor stimulation for disordered breathing therapy in accordance with embodiments of the invention. The implantable device illustrated in FIG. 11B is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering stimulation therapy. It is understood that elements of the ITCS device may be located at several different body locations, such as in the chest, abdominal, or subclavian region with electrode elements respectively positioned at different regions near, around, in, or on the heart.

Circuitry for implementing the NS component may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature. A lead, such as those illustrated in connection with FIGS. 10A-10C may be inserted intravascularly as previously described to electrically couple electrodes to one or more baroreceptor sites.

In one embodiment, cardiac stimulation and/or sensing may be performed by one or more electrodes may be located in direct contact with the heart, great vessel or coronary vasculature, such as via one or more leads implanted by use of conventional transvenous delivery approaches. In another embodiment, for example, one or more subcutaneous electrode subsystems or electrode arrays may be used to sense cardiac activity and/or deliver cardiac stimulation energy in an ITCS device configuration employing an active can or a configuration employing a non-active can. Electrodes may be situated at anterior and/or posterior locations relative to the heart.

In the configuration shown in FIG. 11B, a subcutaneous electrode assembly 1107 can be positioned under the skin in the chest region and situated distal from the housing 1102. The subcutaneous and, if applicable, housing electrode(s) can be positioned about the heart at various locations and orientations, such as at various anterior and/or posterior locations relative to the heart. The subcutaneous electrode assembly 1107 is coupled to circuitry within the housing 1102 via a lead assembly 1106. One or more conductors (e.g., coils or cables) are provided within the lead assembly 1106 and electrically couple the subcutaneous electrode assembly 1107 with circuitry in the housing 1102. One or more sense, sense/pace or defibrillation electrodes can be situated on the elongated structure of the electrode support, the housing 1102, and/or the distal electrode assembly (shown as subcutaneous electrode assembly 1107 in the configuration shown in FIG. 11B).

It is noted that the electrode and the lead assemblies 1107, 1106 can be configured to assume a variety of shapes. For example, the lead assembly 1106 can have a wedge, chevron, flattened oval, or a ribbon shape, and the subcutaneous electrode assembly 1107 can comprise a number of spaced electrodes, such as an array or band of electrodes. Moreover, two or more subcutaneous electrode assemblies 1107 can be mounted to multiple electrode support assemblies 2506 to achieve a desired spaced relationship amongst subcutaneous electrode assemblies 1107.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. Patent Applications Ser. No. 60/462,272, filed Apr. 11, 2003, U.S. Patent Application Publication No. 2004/0230229, U.S. Patent Application Publication No. 2004/0230230, U.S. Patent Application Publication No. 2004/0215258 and U.S. Patent Application Publication No. 2004/0215240 all of which are incorporated by reference.

The housing of the ITCS device may incorporate components of a neural stimulator 1105, including a memory, interface, event detector circuitry, and/or therapy controller. The NS circuitry may be coupled to one or more sensors and/or other input devices as previously described.

In one implementation, the ITCS device may include an impedance sensor configured to sense the patient's transthoracic impedance. The transthoracic impedance sensor may include impedance drive/sense circuitry within the housing 1102 coupled to a can electrode and to one or more impedance electrodes 1108, 1109 positioned on the subcutaneous electrode assembly 1107. The impedance drive circuitry generates a current that flows between a subcutaneous impedance drive electrode 1109 and the can electrode on the primary housing 1102 of the ITCS device. The voltage at a subcutaneous impedance sense electrode 1108 relative to the can electrode changes as the patient's transthoracic impedance changes. The voltage signal developed between the impedance sense electrode 1108 and the can electrode is sensed by the impedance sense circuitry, producing a signal such as that depicted in FIG. 17.

Communications circuitry is disposed within the housing 1102 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

Various embodiments of the invention involve the use of multiple therapy devices working in cooperation to provide therapy for disordered breathing. For example, the multiple therapy devices may include a NS device working synergistically with a CSS device providing cardiac electrical stimulation for disordered breathing, a patient-external therapy device providing respiration therapy, and/or other devices providing disordered breathing therapy. Delivery of different therapies by cooperating devices may provide a comprehensive disordered breathing therapy regimen, providing an enhanced overall outcome. In such an implementation, therapy delivery could be shifted from device to device, depending on the patient's needs. For example, therapy delivery could be shifted from an external respiratory therapy device to the NS and/or CSS devices if it was determined that the patient was not complying with a prescribed external respiratory therapy.

Figure 12A:
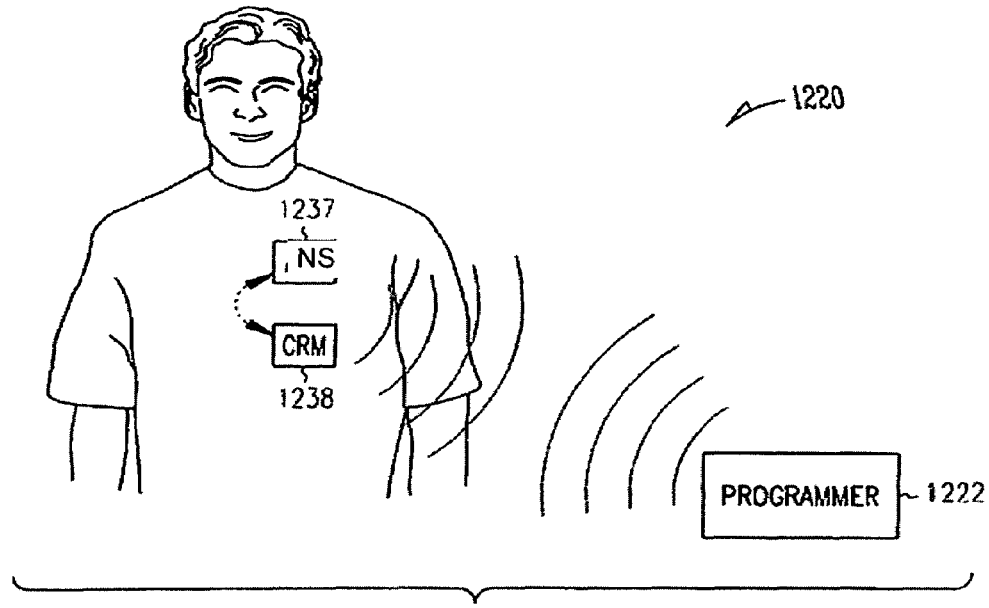
FIG. 12A illustrates a disordered breathing therapy system having a neural stimulator device and a cardiac stimulating and/or sensing device in accordance with embodiments of the invention.

FIG. 12A illustrates a system 1220 including a programmer 1222, an implantable neural stimulator (NS) device 1237 and an implantable CSS device 1238, according to various embodiments. Various aspects involve a method for communicating between an NS device 1237, such as a NS device configured to deliver therapy for disordered breathing, and a CSS device 1238. In various embodiments, this communication allows one of the devices 1237 or 1238 to deliver more appropriate therapy (i.e. more appropriate NS therapy or cardiac stimulation therapy for disordered breathing) based on data received from the other device. Some embodiments provide on-demand communications. In various embodiments, this communication allows each of the devices 1237 and 1238 to deliver more appropriate therapy (i.e. more appropriate NS therapy and cardiac stimulation therapy for disordered breathing) based on data received from the other device. The illustrated NS device 1237 and the CSS device 1238 are capable of wirelessly communicating with each other, and the programmer is capable of wirelessly communicating with at least one of the NS and the CSS devices 1237 and 1238. For example, various embodiments use telemetry coils to wirelessly communicate data and instructions to each other. In other embodiments, communication of data and/or energy is by ultrasonic means.

In some embodiments, the cardiac pacing device 1238 and the NS device cooperate to provide disordered breathing therapy. The cardiac pacing/sensing device 1238 provides electrical stimulation for disordered breathing therapy and the NS 1237 device provides electrical stimulation of the baroreflex response for disordered breathing therapy. Communication between the devices 1237,1238 allows the devices to adjust the cardiac stimulation and/or neural stimulation therapies to provide a more appropriate therapy for the patient. One or both of the CSS device 1238 and the NS device may include one or more sensors for detecting various conditions associated with disordered breathing and/or conditions useful in adjusting therapy for disordered breathing. For example, data acquired by the CSS device 1238 may be communicated to the NS device 1237, and the opposite. The device receiving the data acquired by the other device may use the data to initiate, terminate, or otherwise adjust the therapy delivered by the device. In one scenario, the CSS device 1238 may modify the therapy delivered by the CSS device 1238 based on electrophysiological parameters such as intrinsic heart rate, minute ventilation, atrial activation, ventricular activation, and/or other cardiac events. In addition, the CSS device 1238 can modify the therapy delivered by the CSS device 1238 based on data received from the NS device 1237, such as mean arterial pressure, systolic and diastolic pressure, and baroreceptor stimulation rate.

In one approach, the CSS device 1238 may control the disordered breathing therapy delivered by the NS device 1237. In another approach, the NS device 1237 may control the therapy delivered by the CSS device 1238.

In some embodiments, a communication wire or cable, such as an intravenously-fed lead, may be used for communication between the NS and CSS devices 1237 and 1238. In other embodiments, the NS 1237 and CSS 1238 devices are capable of communicating wirelessly with each other and the programmer is capable of communicating wirelessly with at least one of the NS device 1237 and the CSS device 1238. In other embodiments, both devices 1237, 1238 are capable of bi-directional communication with a separate computing device, such as the programmer, advanced patient management (APM) server, and similar devices, but the devices 1237, 1238 are not capable of communicating with each other directly. In this scenario, the separate computing device, e.g., programmer, APM server, may facilitate transfer of information between the devices 1237, 1238.

Figure 12B:
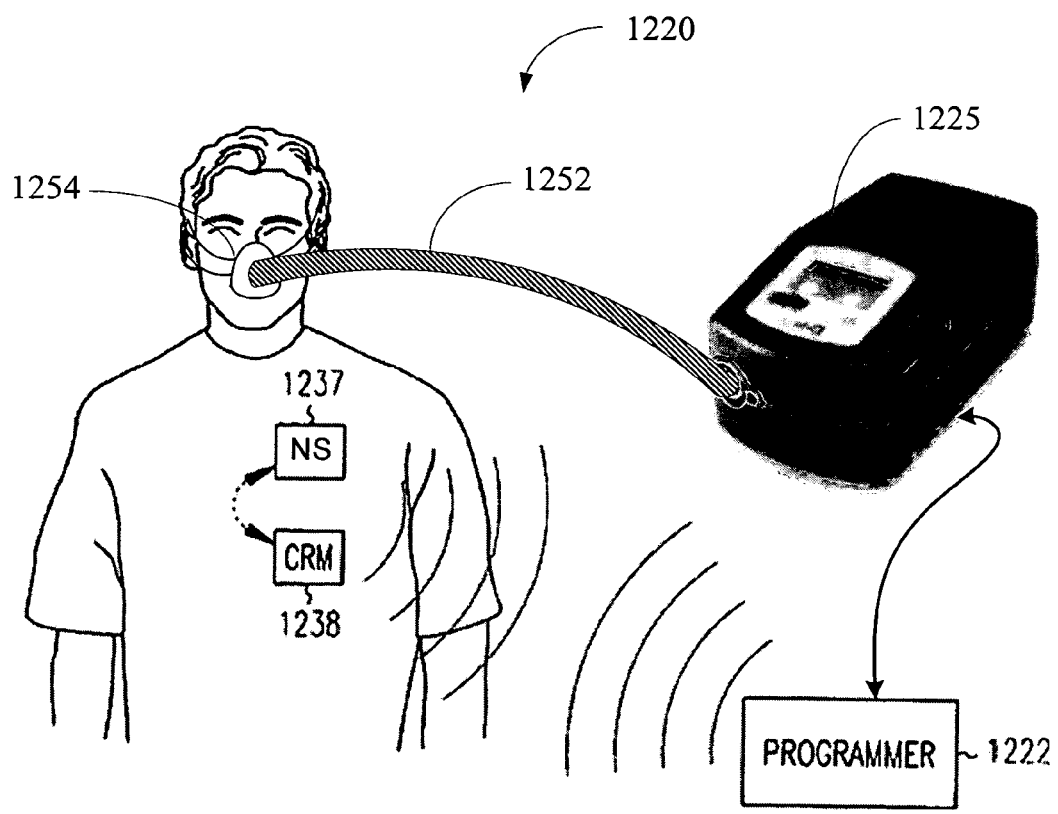
FIG. 12B illustrates a disordered breathing therapy system having a neural stimulator device, a cardiac stimulating and/or sensing device, and an external respiration therapy device in accordance with embodiments of the invention.

In some embodiments, illustrated in FIG. 12B, a system 1220 includes CSS 1238 and NS 1237 devices that cooperate with an external respiration therapy device 1225 to provide disordered breathing therapy. In this embodiment, the CSS device 1238 can provide cardiac electrical stimulation for disordered breathing therapy, the NS device can provide electrical stimulation of the baroreflex response for disordered breathing therapy, and the external respiration therapy device 1225 can provide external breathing therapy to treat disordered breathing. The external respiration therapy device 1225 may comprise, for example, any type of external respiratory therapy device, including, for example, a gas therapy device, respirator, nebulizer, and/or positive airway pressure device. Positive airway pressure therapy is often prescribed to treat disordered breathing. Positive airway pressure devices may be used to provide various types of positive airway pressure therapies, including, for example, continuous positive airway pressure (CPAP), bi-level positive airway pressure, proportional positive airway pressure, and auto-titrating positive airway pressure, ventilation. All types of positive airway pressure devices are referred to herein as xPAP devices. External breathing therapies may also involve the use of respirators, ventilators, and/or gas and oxygen therapy devices, for example.

The xPAP device 1225 develops a positive airway pressure that is delivered to the patient's airway through tubing 1252 and a mask 1254 connected to the xPAP device 1225. In one configuration, for example, the positive airway pressure provided by the xPAP device 1225 acts as a pneumatic splint keeping the patient's airway open and reducing the severity and/or number of occurrences of disordered breathing due to airway obstruction.

The xPAP device 1225 may directly control the delivery of respiration therapy to the patient, and may contribute to the control of the NS device 1237 and/or the CSS device 1238. In addition, the xPAP device 1225 may provide a number of monitoring and/or diagnostic functions in relation to the patient's respiratory system and/or other physiological systems. The xPAP 1225, CSS device 1238, and NS device 1237 may communicate directly to coordinate therapy delivery to the patient, or for other purposes, such as exchange of data acquired by sensors coupled to the devices 1225, 1237, 1238. In another scenario, the devices 1225,1237, 1238 may communicate indirectly through a separate device 1222, such as a programmer or APM server, for example.

In various embodiments, the disordered breathing therapy functions of the CSS device 1238, the NS device 1237, and the xPAP device may be controlled by a disordered breathing therapy controller disposed within the housing of one of the devices 1237, 1238, 1225 or elsewhere. The disordered breathing therapy controller may utilize conditions sensed by one or more of the devices 1237, 1238, 1225 to adapt an appropriate disordered breathing therapy for the patient. Adapting the disordered breathing therapy may involve adjusting the cardiac electrical stimulation therapy for disordered breathing, adjusting the neurostimulation therapy for disordered breathing and/or adjusting the external respiration therapy for disordered breathing. According to this scenario, the disordered breathing therapy controller may distribute the burden of disordered breathing therapy between the devices 1237, 1238, 1225.

In one implementation, certain types of therapy may be used for predetermined periods of time. For example, a predetermined level of cardiac and/or nerve stimulation therapy may be used prior to the patient falling asleep. The therapy burden may be shifted to the external respiratory therapy device after sleep has been detected. In one implementation, the therapy burden may be distributed based on detected arousals. For example, if the delivery of one type of therapy causes the patient to arouse from sleep, the therapy burden may be shifted to other types of therapy to enhance the patient's sleep quality.

In one implementation, the therapy burden may be distributed based on therapy efficacy. In one scenario, the therapy controller may add therapies to the overall disordered breathing therapy regimen to improve therapy efficacy. For example, if the therapy controller determines that disordered breathing is occurring despite the use of one type of therapy, an additional one or more types of therapy may be added to the regimen.

In one scenario, the disordered breathing therapy burden may be distributed based on device usage. For example, if the patient does not use the external respiratory therapy device, then the disordered breathing therapy controller may signal the CSS device 1238 and/or the NS device 1237 to initiate or increase the level of therapy delivered by the CSS device 1238 and/or the NS device 1237.

In one embodiment, the disordered breathing therapy controller may control the disordered breathing therapy to enhance therapy efficacy and/or therapy impact. The therapy controller may acquire information related to the sensed conditions and may evaluate therapy efficacy and/or impact on the patient, i.e., side effects of the therapy, based on the sensed conditions. The therapy controller may modify the therapy delivered by one or more of the therapy devices 1237, 1238, 1225 to enhance therapy efficacy and/or reduce side effects. Further, the therapy controller may modify the therapy to reduce interactions between the disordered breathing therapy and other types of therapies delivered to the patient, e.g., neurostimulation for anti-hypertensive therapy and/or cardiac rhythm management. The therapy controller may modify the therapy to increase the useable lifetime of an implantable device.

Figure 13:
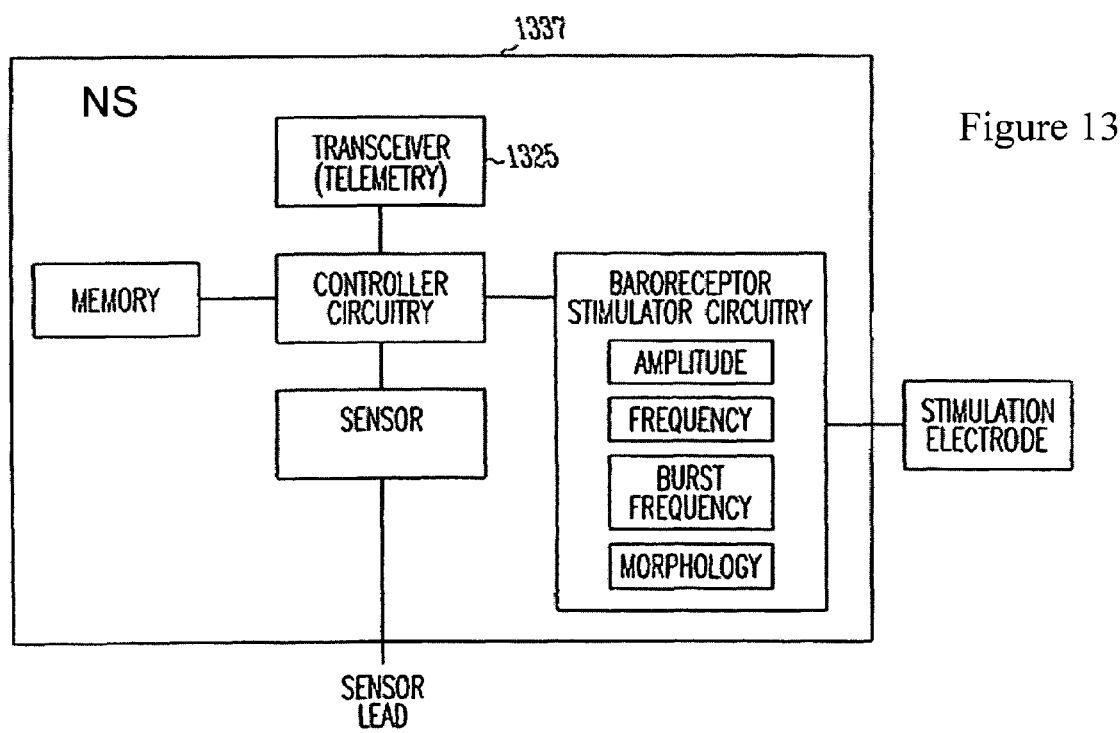
FIG. 13 illustrates a block diagram of a neural stimulation device for disordered breathing therapy in accordance with embodiments of the invention.
Figure 14A:
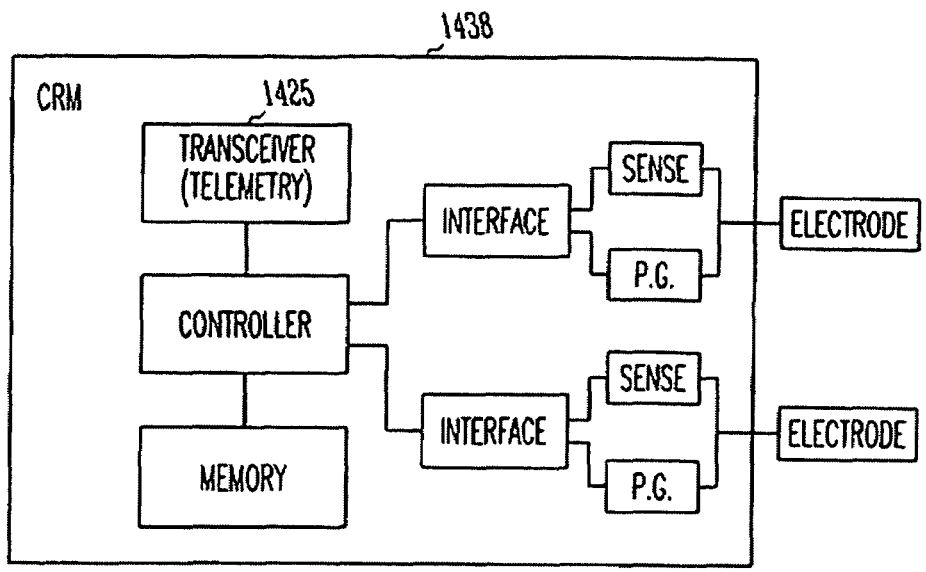
FIG. 14A illustrates a block diagram of an cardiac stimulation and/or sensing device (CSS) device in accordance with embodiments of the invention.
Figure 14B:
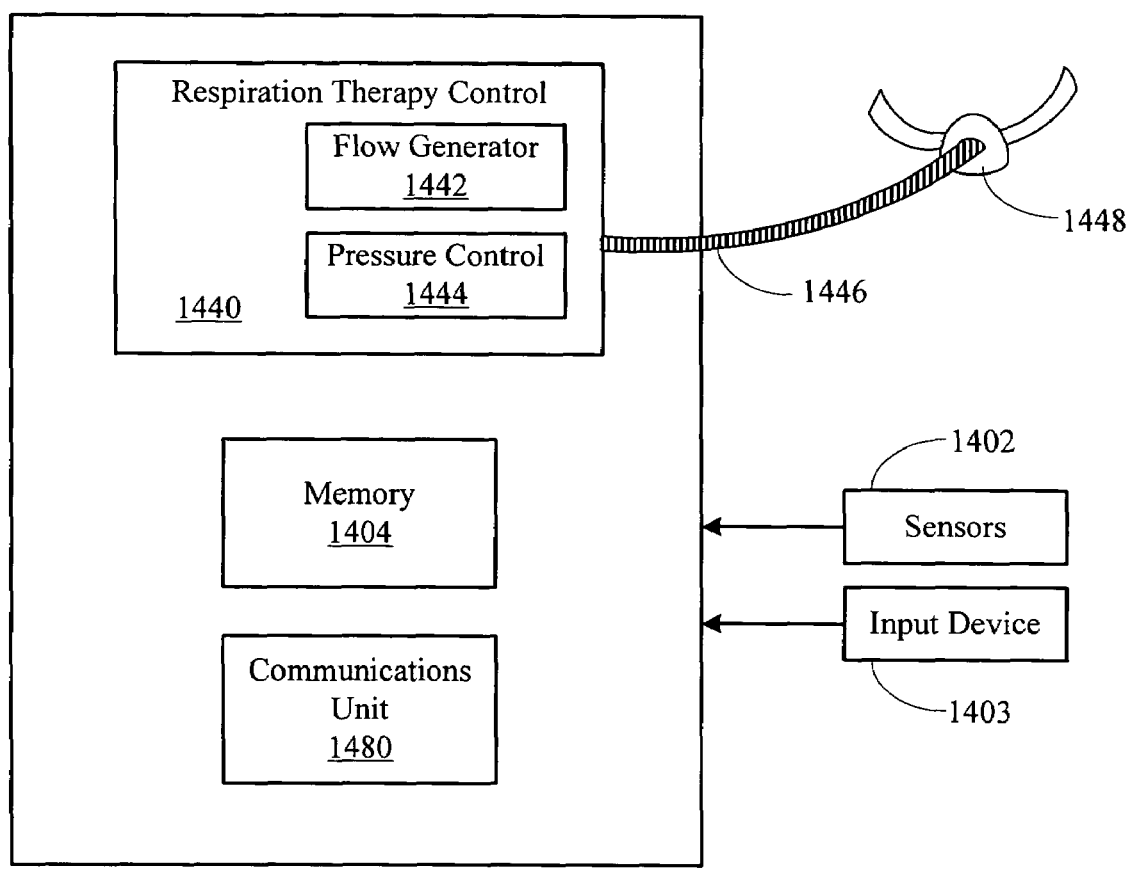
FIG. 14B illustrates a block diagram of a respiratory therapy device in accordance with embodiments of the invention.

FIG. 13 illustrates an implantable neural stimulator (NS) device 1337 such as shown at 1237 in the system of FIGS. 12A and 12B, according to various embodiments of the present subject matter. FIG. 14A illustrates an implantable cardiac stimulation and/or sensing device (CSS) device 1438 such as shown at 1238 in the systems of FIGS. 12A and 12B, according to various embodiments of the present subject matter. FIG. 14B illustrates a block diagram of a respiratory therapy device 1400, e.g., xPAP device, such as shown as 1225 in FIG. 12B.

The NS device 1337, CSS device 1438, and the respiratory therapy device 1400 may be used to provide coordinated patient therapy in accordance with embodiments of the invention. As previously discussed, the xPAP device 1400 may include any type of external respiratory devices, including continuous positive airway pressure devices, bi-level positive airway pressure devices, autotitrating positive airway pressure devices and/or other respiratory therapy devices used in connection with the treatment of disordered breathing.

FIG. 14B illustrates a block diagram of a respiratory therapy device 1400, e.g., xPAP device, in accordance with embodiments of the invention. The xPAP device 1400 may cooperate with other therapy devices such as a CSS device (FIG. 14A) and/or an NS device (FIG. 13).

The xPAP device 1400 may be coupled to sensors 1402, e.g., respiration sensors, or other input devices 1403 configured to sense respiration-related and/or other patient conditions. The xPAP device 1400 includes a memory 1404 used to store data and/or control instructions. The stored information may be periodically transferred to a remote device for further analysis or display. Signals from the sensors 1402 and/or other input devices 1403 may be used by the respiration therapy control unit 1440 to adjust the flow of air delivered to the patient.

The respiration therapy control unit 1440 includes a flow generator 1442 that pulls in air through a filter. The flow generator 1442 is controlled by the pressure control circuitry 1444 to deliver an appropriate air pressure to the patient. Air flows through tubing 1446 coupled to the xPAP device 1300 and is delivered to the patient's airway through a mask 1448. In one example, the mask 1448 may be a nasal mask covering only the patient's nose. In another example, the mask 1448 covers the patient's nose and mouth.

Continuous positive airway pressure (CPAP) devices deliver a set air pressure to the patient. The pressure level for the individual patient may be determined during a titration study. Such a study, which may take place in a sleep lab, involves the determination of an optimum airway pressure by a sleep physician or other professional. The CPAP device pressure control is set to the determined level. When the patient uses the CPAP device, the device operates to maintain a substantially constant airway pressure delivered to the patient.

Autotitration PAP devices are similar to CPAP devices, however, the pressure controller for autotitration devices automatically determines the optimal air pressure for the patient. Instead of maintaining a constant pressure, the autotitration PAP device evaluates sensor conditions and the changing needs of the patient to deliver a variable positive airway pressure. Autotitration PAP and CPAP are most often used to treat sleep disordered breathing.

Bi-level positive airway pressure (bi-PAP) devices provide two levels of positive airway pressure. A higher pressure is maintained while the patient inhales. The device switches to a lower pressure during exhalation. Bi-PAP devices are used to treat a variety of respiratory dysfunctions, including disordered breathing, chronic obstructive pulmonary disease (COPD), respiratory insufficiency, and ALS or Lou Gehrig's disease, among others.

The xPAP device 1400 may include a communication unit 1480, which may be configured as a wireless transceiver, for facilitating communication with one or more separate devices, including patient-external or patient-internal devices, such as the CSS device (FIG. 14A), and/or the NS device (FIG. 13). Communication between cooperating devices allows the xPAP device 1400 to provide information to the separate devices or to control therapy delivered by the separate devices and/or to receive data or therapy control signals from the separate devices, for example.

Various embodiments of the NS, CSS, and/or xPAP devices include wireless transceivers 1325 (FIG. 13), 1425 (FIG. 14A), 1480 (FIG. 14B), respectively, to wirelessly communicate directly or indirectly with each other, and/or with a separate device, such as a programmer or APM system. For example, communication circuitry of the NS, CSS and/or xPAP devices, may involve the use of a telemetry coil or ultrasonic transducer for wireless communication.

Figure 15:
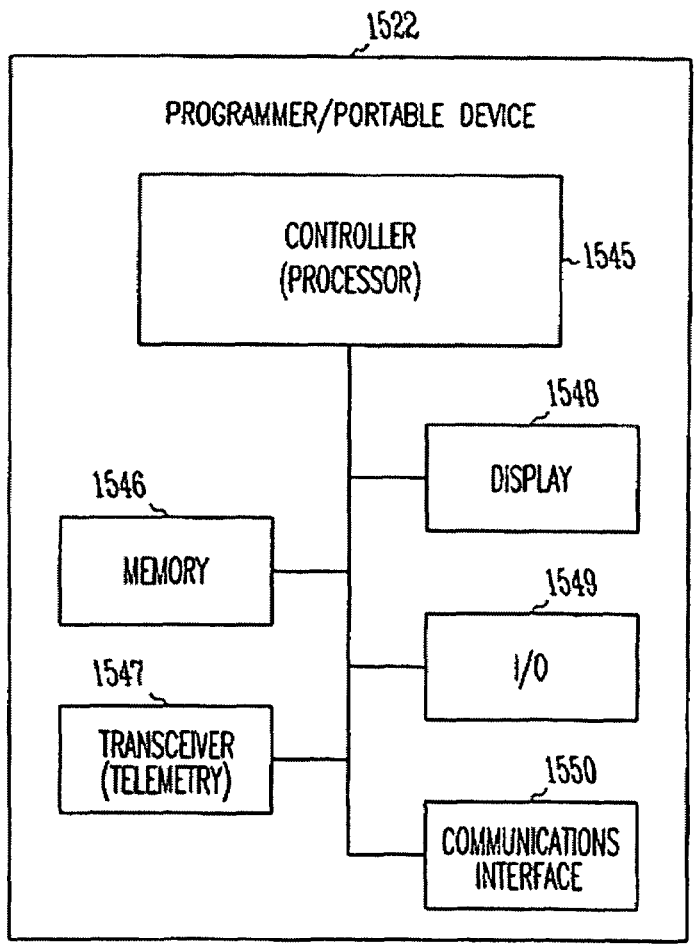
FIG. 15 illustrates a block diagram of a programmer in accordance with embodiments of the invention.

FIG. 15 illustrates a programmer 1522, such as the programmer 822 and 1222 illustrated in the systems of FIGS. 8 and 12, or other external device to communicate with the implantable medical device(s) 1337, 1438 and/or 1400, according to various embodiments of the present subject matter. Examples of another external device include Personal Digital Assistants (PDAs), laptop computers, desktop computers and/or computing devices of an Advanced Patient Management (APM) system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and/or the patient information server, for example, to submit or acquire patient data or to initiate, terminate and/or modify therapy or other functions provided by the medical devices.

Methods, structures, or techniques described herein relating to advanced patient management, such as remote patient monitoring, diagnostics and/or therapy, or other advance patient management methodologies can incorporate features of one of more of the following references: U.S. Pat. Nos. 6,221,011, 6,270,457, 6,280,380, 6,312,378, 6,336,903, 6,358,203, 6,368,284, 6,398,728, 6,440,066, which are incorporated herein by reference.

The illustrated device 1522 includes controller circuitry 1545 and memory 1546. The controller circuitry 1545 is capable of being implemented using hardware, software, and combinations of hardware and software. For example, according to various embodiments, the controller circuitry 1545 includes a processor to perform instructions embedded in the memory 1546 to perform a number of functions, including communicating data and/or programming instructions to the implantable devices. The illustrated device 1522 further includes a transceiver 1547 and associated circuitry for communicating with an implantable and/or patient-external device. Various embodiments have wireless communication capabilities. For example, various embodiments of the transceiver 1547 and associated circuitry include a telemetry coil for wirelessly communicating with an implantable and/or patient-external device. The illustrated device 1522 further includes a display 1548, input/output (I/O) devices 1549 such as a keyboard or mouse/pointing device, and a communications interface 1550 for communicating with other devices, such as over a communications network.

Neural stimulation, cardiac stimulation, and/or respiration therapy functions of a disordered breathing therapy system may each provide a component of a coordinated therapy for disordered breathing. Additionally or alternatively the neural stimulation, cardiac pacing and/or respiratory therapy functions may provide therapy for diseases or disorders other than disordered breathing. These processes can be controlled by a processor executing computer-readable instructions embedded in memory, for example. These therapies include a number of applications, which have various processes and functions, some of which are identified and discussed below. The processes and functions of these therapies are not necessarily mutually exclusive, as some embodiments of the present invention include combinations of two or more of the below identified processes and functions.

FIGS. 16A-16D illustrate a system and methods to prevent interference between electrical stimulation from a neural stimulator (NS) device and sensing by a cardiac stimulation/sensing (CSS) device, delivering cardiac rhythm management therapy, such as bradycardia pacing, according to various embodiments of the invention. The NS device may provide disordered breathing therapy as well as anti-hypertensive therapy in some embodiments. Neural stimulation is accounted for to improve the ability to sense signals, and thus reduce or eliminate false positives associated with detecting a cardiac event. For example, the NS device communicates with and prevents or otherwise compensates for baroreflex stimulation such that the CSS device does not unintentionally react to the baroreflex stimulation. Some embodiments automatically synchronize the baroreflex stimulation with an appropriate refractory period of the heart. For example, some systems automatically synchronize stimulation of the baroreceptors in or around the pulmonary artery with atrial activation. Thus, the functions of the CSS device are not adversely affected by detecting far-field noise generated by the baroreflex stimulation, even when the baroreflex stimulations are generated near the heart and the CSS sensors that detect the cardiac electrical activation.

Figure 16A:
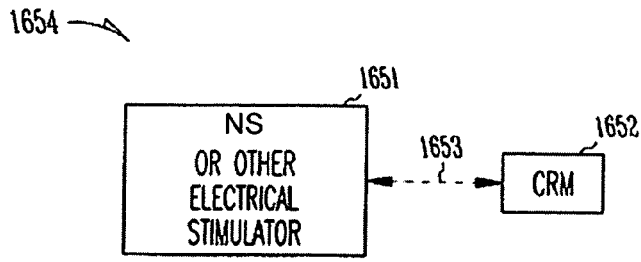
FIGS. 16A-16D illustrate a system and methods to prevent interference between electrical stimulation from a neural stimulator and sensing by a cardiac device in accordance with various embodiments of the invention.

FIG. 16A generally illustrates a system 1654 that includes NS functions 1651 (such as may be performed by a NS device or a NS component in an integrated NS/CSS device), CSS functions 1652 (such as may be performed by a CSS device or a CSS component in an integrated NS/CSS device), and capabilities to communicate 1653 between the NS and CSS functions. The illustrated communication is bi-directional wireless communication. However, the present subject matter also contemplates unidirectional communication, and further contemplates wired communication. Additionally, the present subject matter contemplates that the NS and CSS functions 1651, 1652 can be integrated into a single implantable device such that the communication signal is transmitted and received in the device, or in separate implantable devices. Although baroreflex stimulation as part of neural stimulation is specifically discussed, this aspect of the present invention is also applicable to prevent, or account, or otherwise compensate for unintentional interference detectable by a sensor and generated from other electrical stimulators.

Figure 16B:
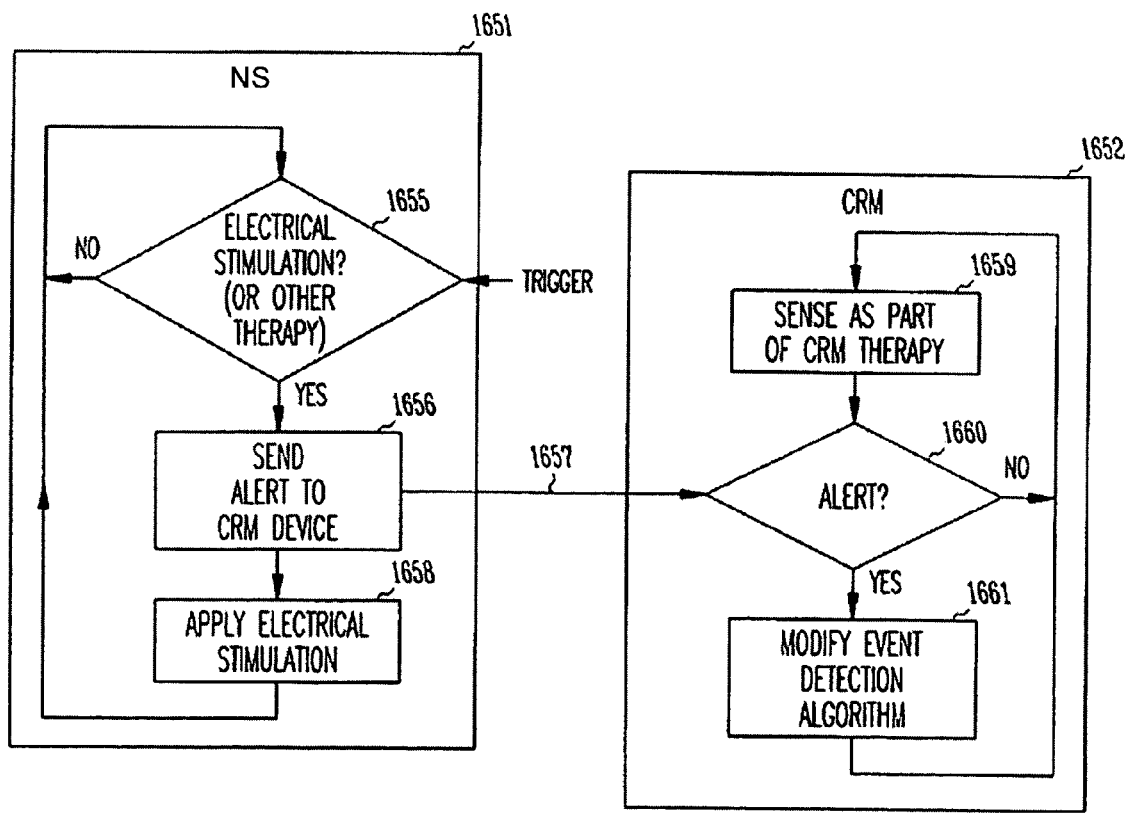

FIG. 16B illustrates a process where CSS functions do not unintentionally react to baroreflex stimulation, according to various embodiments. FIG. 16B illustrates a process where the NS device or component 1651 sends an alert or otherwise informs the CSS device or component when baroreceptors are being electrically stimulated. In the illustrated embodiments, the NS device/component 1651 determines if electrical stimulation, such as baroreflex stimulation, is to be applied. When electrical stimulation is to be applied, the NS device or component 1651 sends 1656 an alert 1657 or otherwise informs the CSS device or component 1652 of the electrical stimulation. The electrical stimulation is applied 1658 by the NS device/component. The CSS therapy, including sensing, is performed 1659. The CSS device determines whether an alert has been received from the NS device/component. If an alert has been received, an event detection algorithm is modified 1661 to raise a detection threshold, provide a blackout or blanking window, or otherwise prevent the electrical stimulation in the NS device or component from being misinterpreted as an event by the CSS device/component.

Figure 16C:
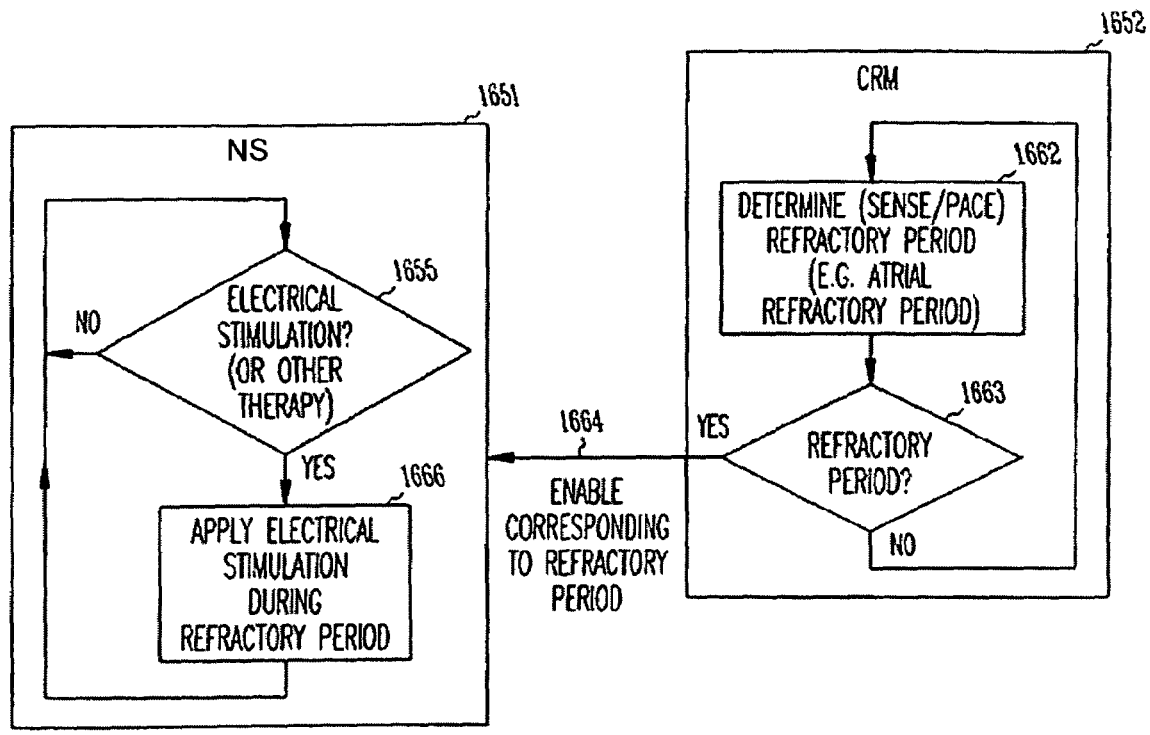
Figure 16D:
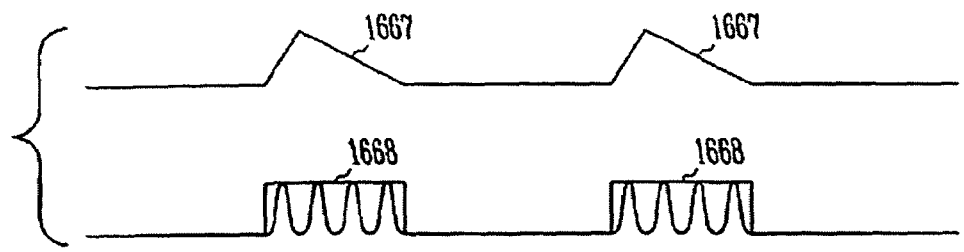

FIG. 16C illustrates a process where CSS functions do not unintentionally react to baroreflex stimulation, according to embodiments of the invention. The CSS device/component 1652 determines a refractory period for the heart 1662. If a refractory period is occurring or is expected to occur 1663 in a predictable amount of time, an enable 1664 corresponding to the refractory is provided to the NS device/component 1651. The NS device/component 1651 determines if electrical stimulation is desired at 1665. When desired, the NS device/component applies electrical stimulation during 1666 a refractory period, as controlled by the enable signal 166. FIG. 16D illustrates a refractory period at 1667 in a heart and a baroreflex stimulation 1668, and further illustrates that baroreflex stimulation is applied during the refractory period.

A refractory period includes both absolute and relative refractory periods. Cardiac tissue is not capable of being stimulated during the absolute refractory period. The required stimulation threshold during an absolute refractory period is basically infinite. The relative refractory period occurs after the absolute refractory period. During the relative refractory period, as the cardiac tissue begins to repolarize, the stimulation threshold is initially very high and drops to a normal stimulation threshold by the end of the relative refractory period. Thus, according to various embodiments, a neural stimulator applies neural stimulation during either the absolute refractory period, or during a portion of the relative refractory period corresponding to a sufficiently high stimulation threshold to reduce the likelihood of the neural stimulation from capturing cardiac tissue.

Embodiments of the invention relate to a method of sensing atrial activation and confining pulmonary artery stimulation to the atrial refractory period, reducing the likelihood of unintentional stimulation of nearby atrial tissue. An implantable baroreceptor stimulation device monitors atrial activation with an atrial sensing lead. A lead in the pulmonary artery stimulates baroreceptors in the vessel wall. However, instead of stimulating these baroreceptors continuously, the stimulation of baroreceptors in the pulmonary artery occurs during the atrial refractory period to reduce the likelihood of capturing nearby atrial myocardium, thus maintaining the intrinsic atrial rate and activation. Various embodiments of the present invention combine an implantable device for stimulating baroreceptors in the wall of the pulmonary artery with the capability for atrial sensing. Various embodiments stimulate in the parasympathetic ganglia in the cardiac fat pads, baroreceptors in the heart chambers, and/or afferent nerves.

Embodiments of the invention involve delivering an electrical stimulation therapy that modifies a patient's baroreflex response to treat disordered breathing. The therapy may be delivered, for example, in response to detection or prediction of disordered breathing. The therapy may be adapted based on various conditions affecting the patient. In the examples described below, the therapy can be adapted to improve the efficacy of the therapy, to reduce an impact of the therapy on the patient, to mitigate therapy interactions and/or for other reasons. Methods and systems for predicting disordered breathing, aspects of which may be utilized in connection with modulating a patient's baroreflex response to treat disordered breathing are described in commonly owned U.S. patent application Ser. No. 10/643,016, filed Aug. 18, 2003 which is incorporated herein by reference.

Although disordered breathing often occurs during sleep, the condition may also occur while the patient is awake. The respiratory disruptions caused by disordered breathing can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer. Systems and methods for classifying disordered breathing events as central, obstructive or mixed in origin, aspects of which may be utilized in connection with delivering a therapy to treat disordered breathing in accordance with embodiments of the present invention, are described in commonly owned U.S. patent application Ser. No. 10/824,776 entitled "System and Method for Discrimination of Central and Obstructive Disordered Breathing Events," filed Apr. 15, 2004, which is incorporated herein by reference. In various embodiments of the invention, a first therapy regimen may be delivered to treat central disordered breathing events, a second therapy regimen to treat obstructive disordered breathing events, and a third therapy regimen to treat disordered breathing events of mixed origin. Each of the first, second, and third therapy regimens may utilize different types of disordered breathing therapies or may utilize a single type of therapy with different parameter settings.

Various conditions affecting the patient may be used for adapting the therapy and/or predicting or detecting disordered breathing. The conditions may include one or more physiological and non-physiological (contextual) conditions. Physiological conditions may include a broad category of conditions associated with the internal functioning of the patient's physiological systems, including the cardiovascular, respiratory, nervous, muscle, and other systems.

Contextual conditions generally encompass non-physiological, patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. patent application entitled "Methods and Devices for Detection of Context When Addressing A Medical Condition of a Patient," Ser. No. 10/269611, filed Oct. 11, 2002, which is incorporated by reference herein in its entirety.

Table 1 provides a representative set of patient conditions that may be used in connection with delivering a baroreflex therapy for disordered breathing in accordance with embodiments of the invention. Table 1 also provides illustrative sensing methods that may be employed to sense the conditions. It will be appreciated that patient conditions and detection methods other than those listed in Table 1 may be used and are considered to be within the scope of the invention.

TABLE 1

| Condition Type | | Condition | Sensor type or Detection method |
|---|---|---|---|
| Physiological | Cardiovascular System | Heart rate<br>Heart rate variability<br>QT interval | EGM, ECG |
| | | Ventricular filling pressure | Intracardiac pressure sensor |
| | | Blood pressure | Blood pressure sensor |
| | Respiratory System | Snoring | Accelerometer<br>Microphone |
| | | Respiration pattern<br>(Tidal volume Minute<br>ventilation Respiratory rate) | Transthoracic impedance sensor (AC) |

TABLE 1-continued

| Condition Type | | Condition | Sensor type or Detection method |
|---|---|---|---|
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation | Blood analysis |
| | | O2 saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

Detection or prediction of disordered breathing may involve comparing one condition or multiple conditions to one or more thresholds or other indices indicative or predictive of disordered breathing. A threshold or other index indicative or predictive of disordered breathing may comprise a predetermined level of a particular condition, e.g., blood oxygen level less than a predetermined amount, tidal volume less than a predetermined amount for a predetermined period of time. A threshold or other index indicative or predictive of disordered breathing may involve a change in a level of a particular condition, e.g., heart rate decreasing from a sleep rate to a lower rate within a predetermined time interval.

In one approach, the relationships between conditions may be indicative or predictive of disordered breathing. In this approach, disordered breathing detection or prediction may be based on the presence and relative values associated with two or more conditions. For example, if condition A is present at a level of x, then condition B must also be present at a level of f(x) before disordered breathing is detection or predicted.

The thresholds and/or relationships indicative or predictive of disordered breathing may be highly patient specific. The thresholds and/or relationships indicative of disordered breathing may be determined on a case-by-case basis by monitoring conditions affecting the patient and monitoring disordered breathing episodes. The analysis may involve determining levels of the monitored conditions and/or relationships between the monitored conditions associated, e.g., statistically correlated, with disordered breathing episodes. The thresholds and/or relationships used in disordered breathing detection or prediction may be updated periodically to track changes in the patient's response to disordered breathing.

In accordance with one embodiment of the invention, the electrical stimulation therapy is delivered responsive to a detection of disordered breathing. Disordered breathing is a serious respiratory condition involving disruption of the normal respiratory cycle. In this approach, the baroreflex therapy is delivered to mitigate or terminate a detected episode of disordered breathing.

Disordered breathing may be detected by sensing and analyzing various conditions indicative of disordered breathing. Table 2 provides examples of how a representative subset of the physiological and contextual conditions listed in Table 1 can be used in connection with disordered breathing detection.

TABLE 2

| Condition Type | Condition | Examples of how condition may be used in disordered breathing detection |
| --- | --- | --- |
| Physiological | Heart rate | Decrease in heart rate may indicate disordered breathing episode. |
| | | Increase in heart rate may indicate autonomic arousal from a disordered breathing episode. |
| | | Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. |
| | | Respiration patterns may be used to determine the type of disordered breathing. |
| | | Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | $CO_2$ | Low $CO_2$ levels initiate central apnea. |
| | $O_2$ | $O_2$ desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/Medication/Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

In various implementations, episodes of disordered breathing may be detected and classified by analyzing the patient's respiration patterns. Methods and systems of disordered breathing detection, aspects of which may be utilized in delivering a baroreceptor therapy for disordered breathing in accordance with the present invention, are further described in commonly owned U.S. Patent Application Publication No. 2004/0111040 and incorporated herein by reference.

Figure 17:
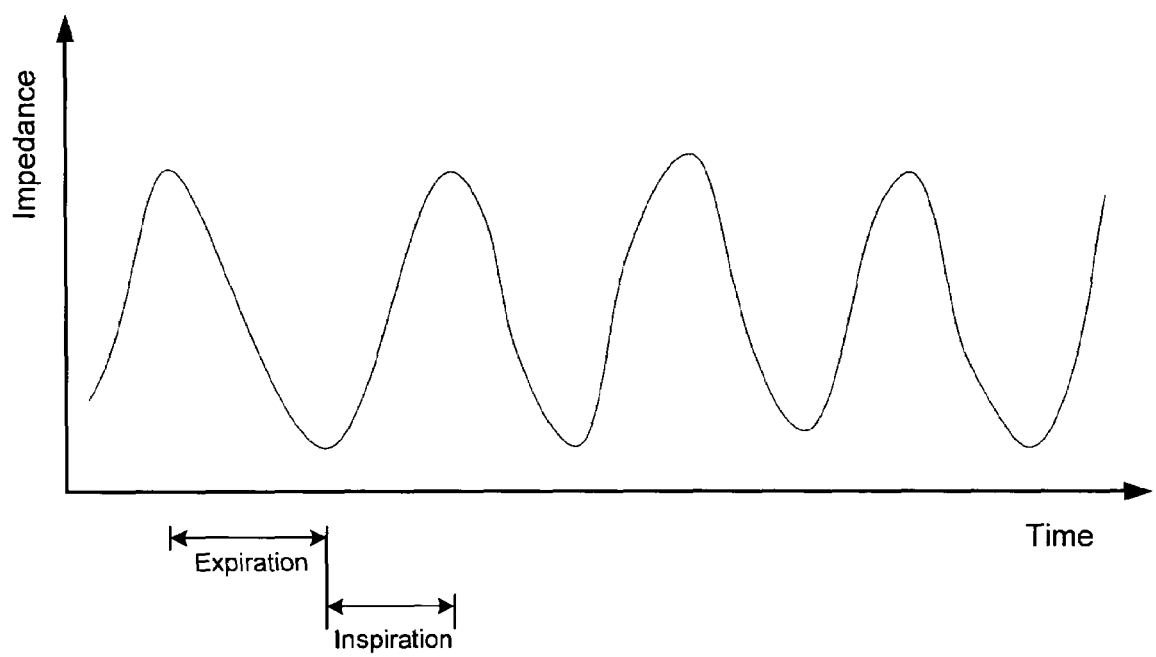
FIG. 17 illustrates normal respiration as represented by a signal produced by a transthoracic impedance sensor in accordance with embodiments of the invention.

FIG. 17 illustrates normal respiration as represented by a signal produced by a transthoracic impedance sensor. The transthoracic impedance increases during respiratory inspiration and decreases during respiratory expiration. During non-REM sleep, a normal respiration pattern includes regular, rhythmic inspiration—expiration cycles without substantial interruptions. Transthoracic impedance may be detected using intracardiac, subcutaneous, or patient-external electrodes.

In one embodiment, episodes of disordered breathing may be detected by monitoring the respiratory waveform output of the transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 18:
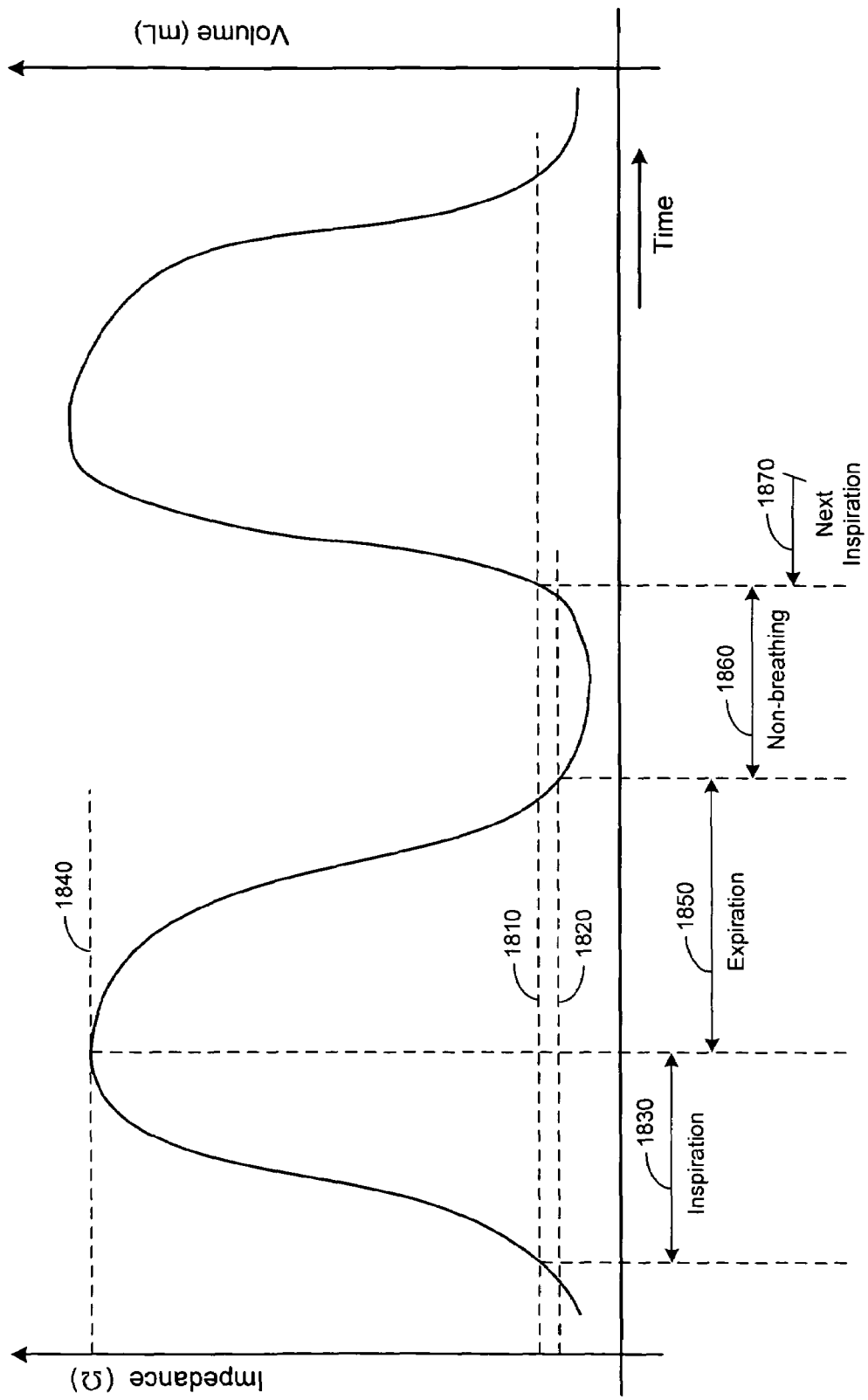
FIG. 18 illustrates respiration intervals used for disordered breathing detection according to embodiments of the invention.

In another embodiment, detection of disordered breathing involves defining and examining a number of respiratory cycle intervals. FIG. 18 illustrates respiration intervals used for disordered breathing detection according to embodiments of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1810 and expiration 1820 thresholds. The inspiration threshold 1810 marks the beginning of an inspiration period 1830 and is determined by the transthoracic impedance signal rising above the inspiration threshold 1810. The inspiration period 1830 ends when the transthoracic impedance signal is maximum 1840. A maximum transthoracic impedance signal 1840 corresponds to both the end of the inspiration interval 1830 and the beginning of the expiration interval 1850. The expiration interval 1850 continues until the transthoracic impedance falls below an expiration threshold 1820. A non-breathing interval 1860 starts from the end of the expiration period 1850 and continues until the beginning of the next inspiration period 1870.

Figure 19:
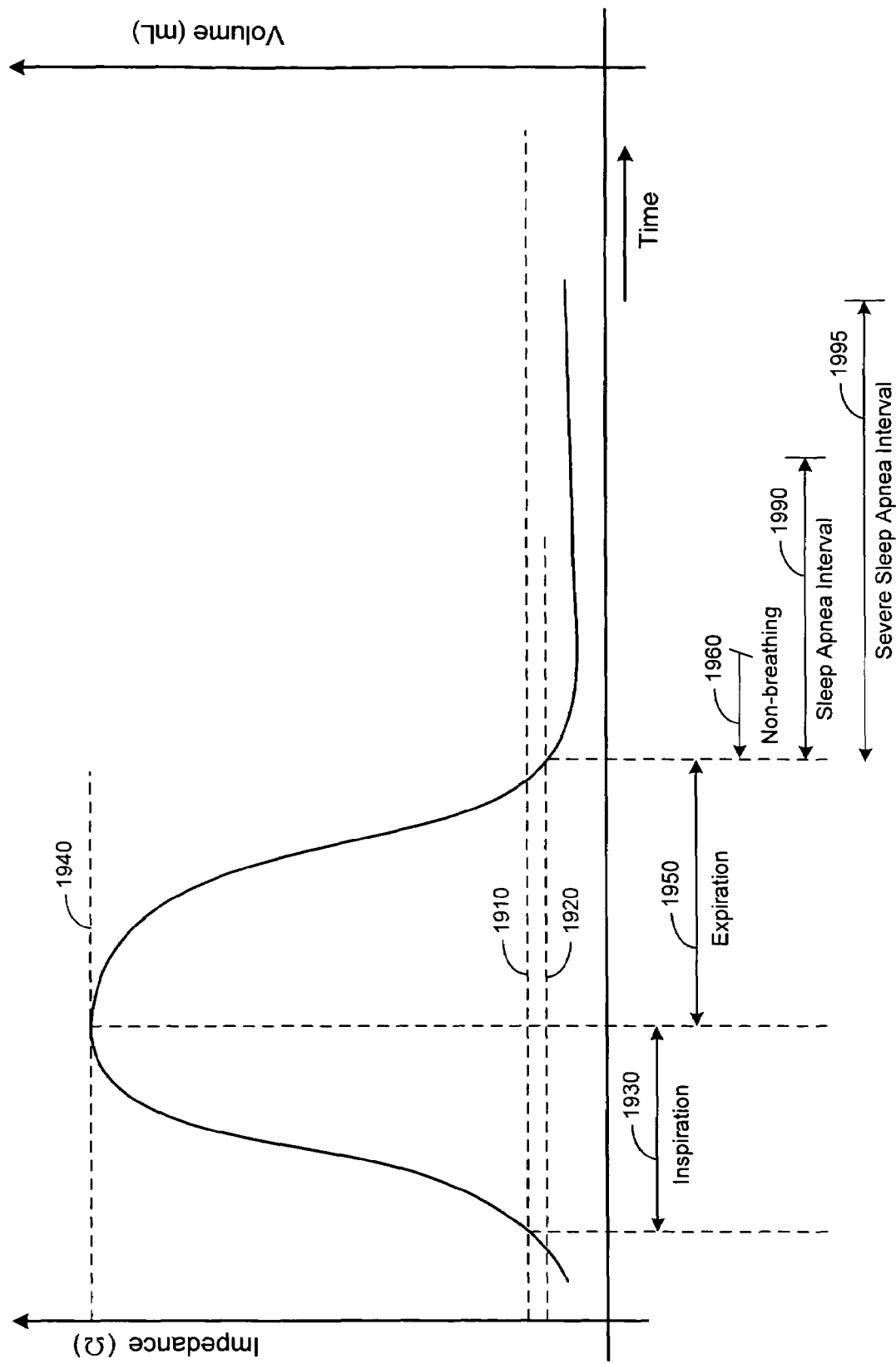
FIG. 19 illustrates detection of sleep apnea and severe sleep apnea according to embodiments of the invention.

Detection of sleep apnea and severe sleep apnea according to embodiments of the invention is illustrated in FIG. 19. The patient's respiration signals are monitored and the respiration cycles are defined according to inspiration 1930, expiration 1950, and non-breathing 1960 intervals as described in connection with FIG. 18. A condition of sleep apnea is detected when a non-breathing period 1960 exceeds a first predetermined interval 1990, denoted the sleep apnea interval. A condition of severe sleep apnea is detected when the non-breathing period 1960 exceeds a second predetermined interval 1995, denoted the severe sleep apnea interval. For example, sleep apnea may be detected when the non-breathing interval exceeds about 10 seconds, and severe sleep apnea may be detected when the non-breathing interval exceeds about 20 seconds.

Figure 20A:
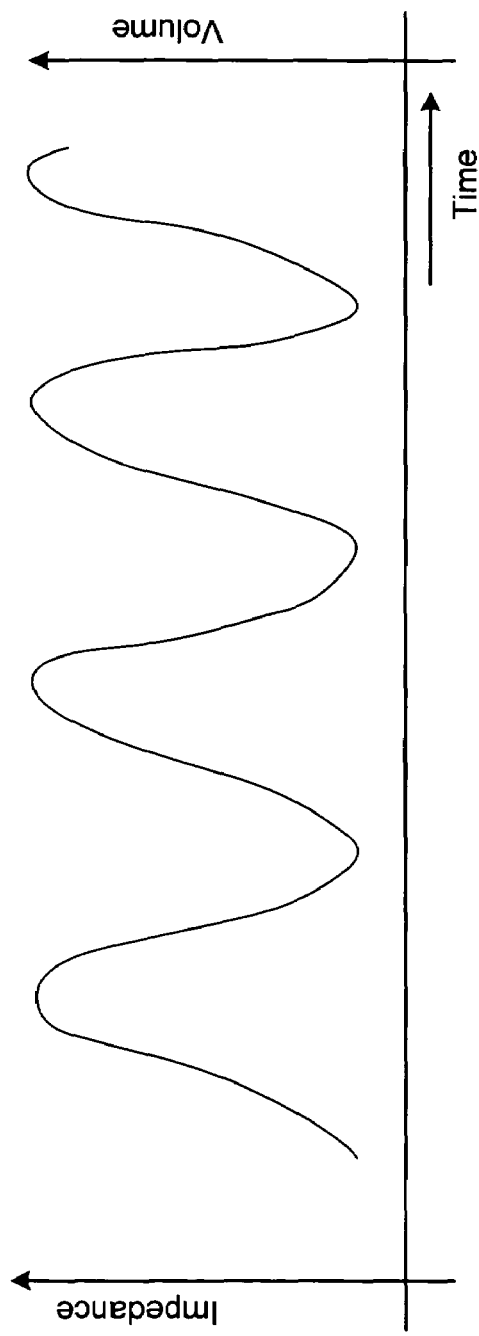
FIGS. 20A-20B are respiration graphs derived from transthoracic impedance measurements illustrating normal and hypopneic intervals in accordance with embodiments of the invention.
Figure 20B:
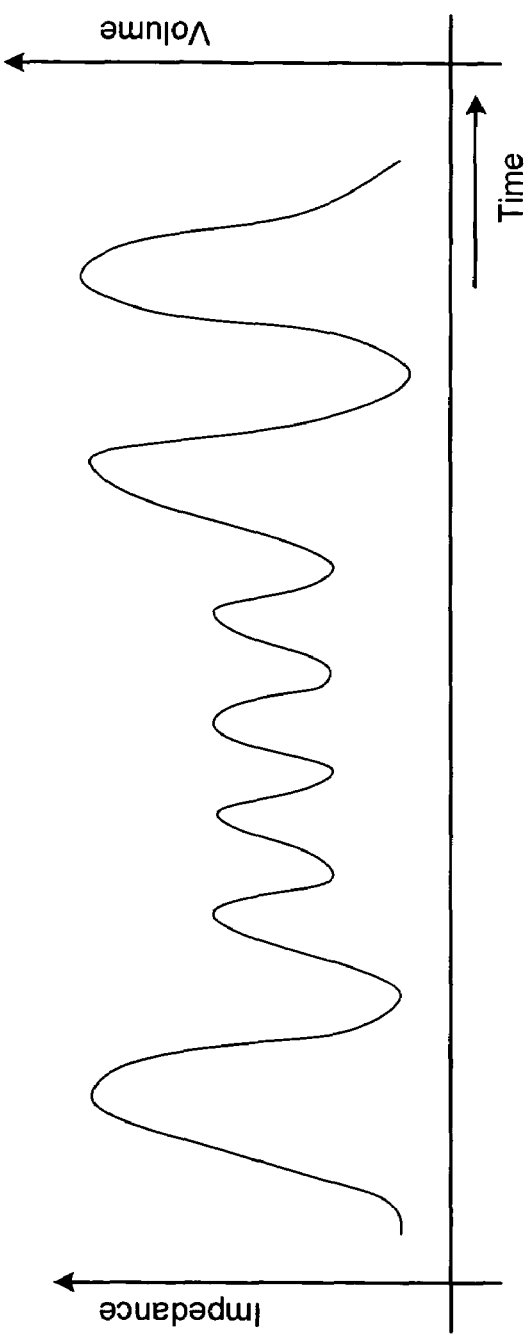

Hypopnea is a condition of disordered breathing characterized by abnormally shallow breathing. FIGS. 20A-20B are graphs of tidal volume derived from transthoracic impedance measurements. The graphs compare the tidal volume of a normal breathing cycle to the tidal volume of a hypopnea episode. FIG. 20A illustrates normal respiration tidal volume and rate. As shown in FIG. 20B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 21:
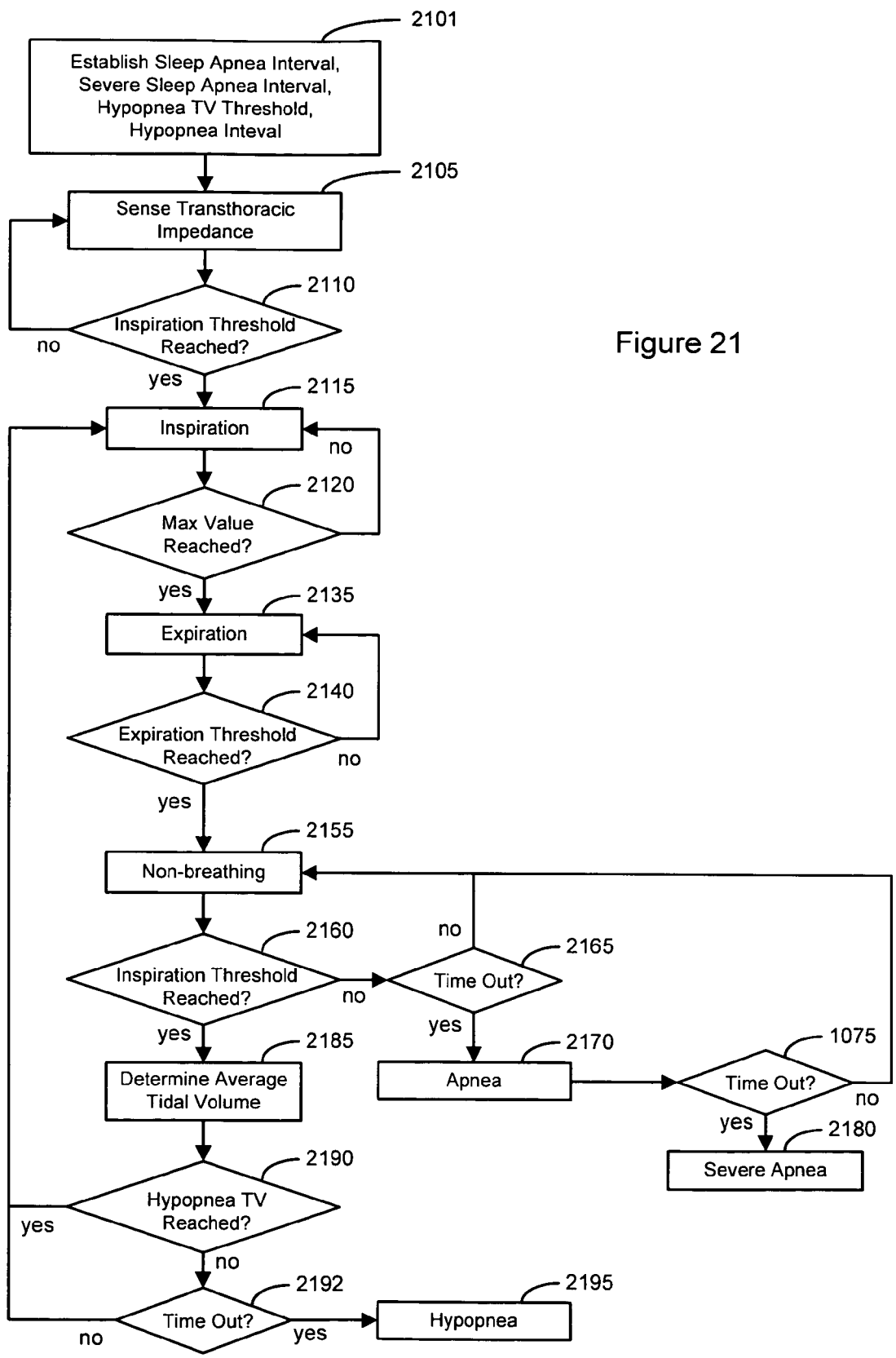
FIG. 21 is a flowchart illustrating a method of apnea and/or hypopnea detection according to embodiments of the invention.

FIG. 21 is a flow chart illustrating a method of apnea and/or hypopnea detection according to embodiments of the invention. Various parameters are established 2101 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 2105 as described in more detail above. If the transthoracic impedance exceeds 2110 the inspiration threshold, the beginning of an inspiration interval is detected 2115. If the transthoracic impedance remains below 2110 the inspiration threshold, then the impedance signal is checked 2105 periodically until inspiration 2115 occurs.

During the inspiration interval, the patient's transthoracic impedance is monitored until a maximum value of the transthoracic impedance is detected 2120. Detection of the maximum value signals an end of the inspiration period and a beginning of an expiration period 2135.

The expiration interval is characterized by decreasing transthoracic impedance. When the transthoracic impedance falls 2140 below the expiration threshold, a non-breathing interval is detected 2155.

If the transthoracic impedance does not exceed 2160 the inspiration threshold within a first predetermined interval 2165, denoted the sleep apnea interval, then a condition of sleep apnea is detected 2170. Severe sleep apnea is detected 2180 if the non-breathing period extends beyond a second predetermined interval 2175, denoted the severe sleep apnea interval.

When the transthoracic impedance exceeds 2160 the inspiration threshold, the tidal volume from the peak-to-peak transthoracic impedance is calculated, along with a moving average of past tidal volumes 2185. The peak-to-peak transthoracic impedance provides a value proportional to the tidal volume of the respiration cycle. This value is compared to a hypopnea tidal volume threshold 2190. If the peak-to-peak transthoracic impedance is consistent with the hypopnea tidal volume threshold 2190 for a predetermined time 2192, then a hypopnea cycle is detected 2195.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 22:
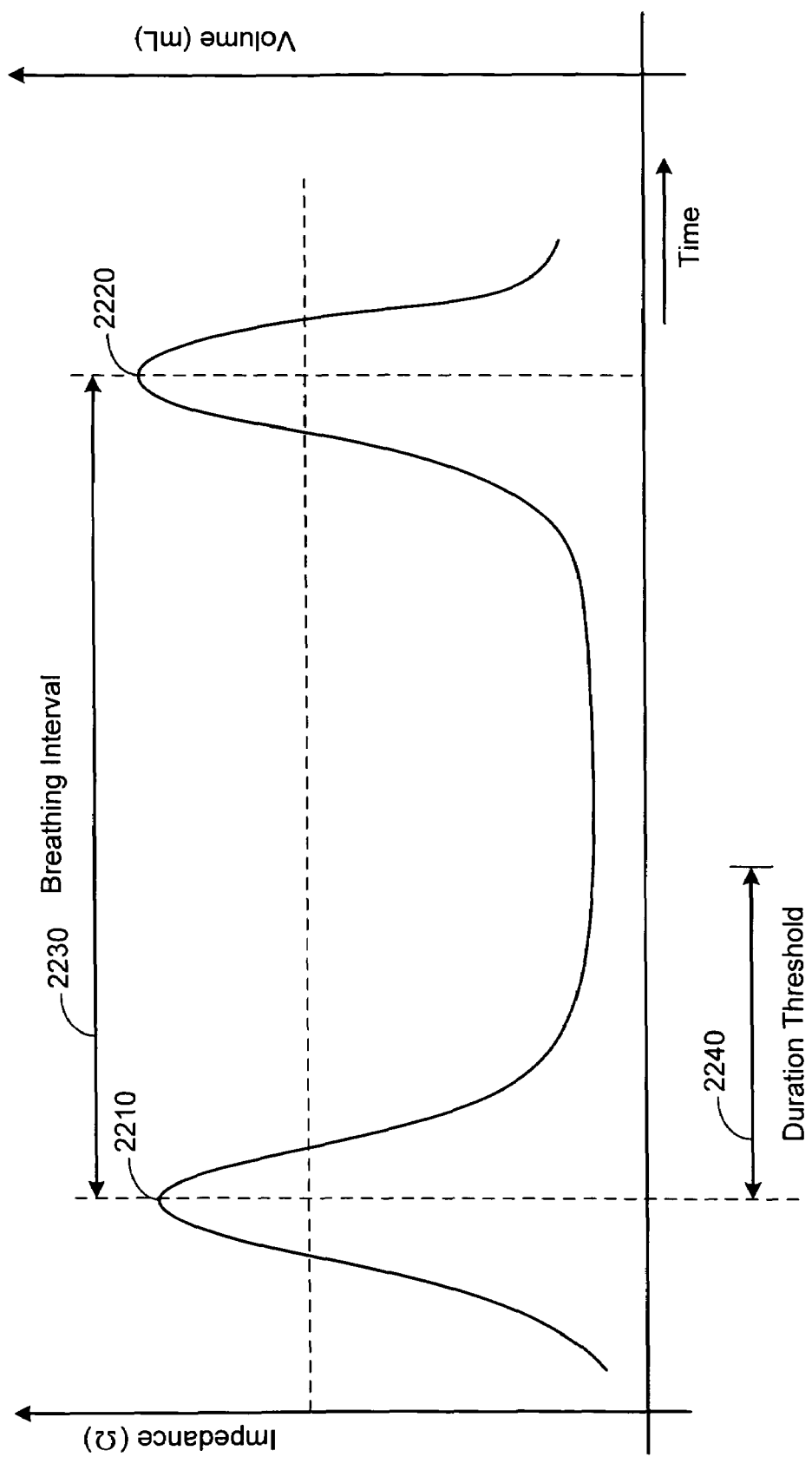
FIG. 22 is a graph illustrating breath intervals that may be used for disordered breathing detection in accordance with embodiments of the invention.

According to principles of the invention, a breath interval is established for each respiration cycle. A breath interval represents the interval of time between successive breaths, as illustrated in FIG. 22. A breath interval 2230 may be defined in a variety of ways, for example, as the interval of time between successive maxima 2210, 2220 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 22. Apnea represents a period of non-breathing. A breath interval 2230 exceeding a duration threshold 2240 comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 23:
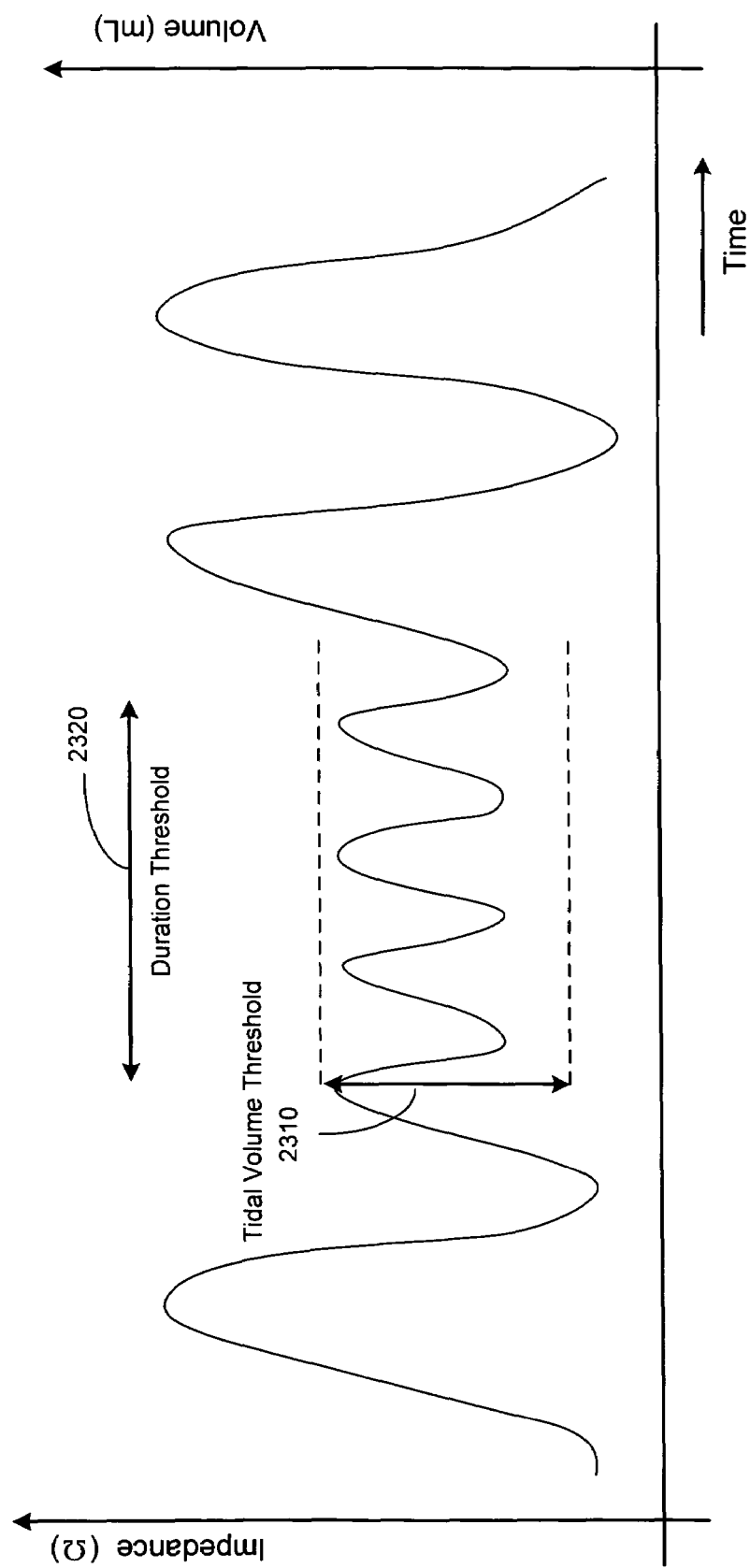
FIG. 23 is a graph illustrating a hypopnea detection approach in accordance with embodiments of the invention.

A hypopnea detection approach, in accordance with embodiments of the invention, is illustrated in FIG. 23. Shallow breathing is detected when the tidal volume of one or more breaths is below a tidal volume threshold 2310. If the shallow breathing continues for an interval greater than a duration threshold 2320, then the breathing pattern represented by the sequence of shallow respiration cycles, is classified as a hypopnea event.

Figure 24:
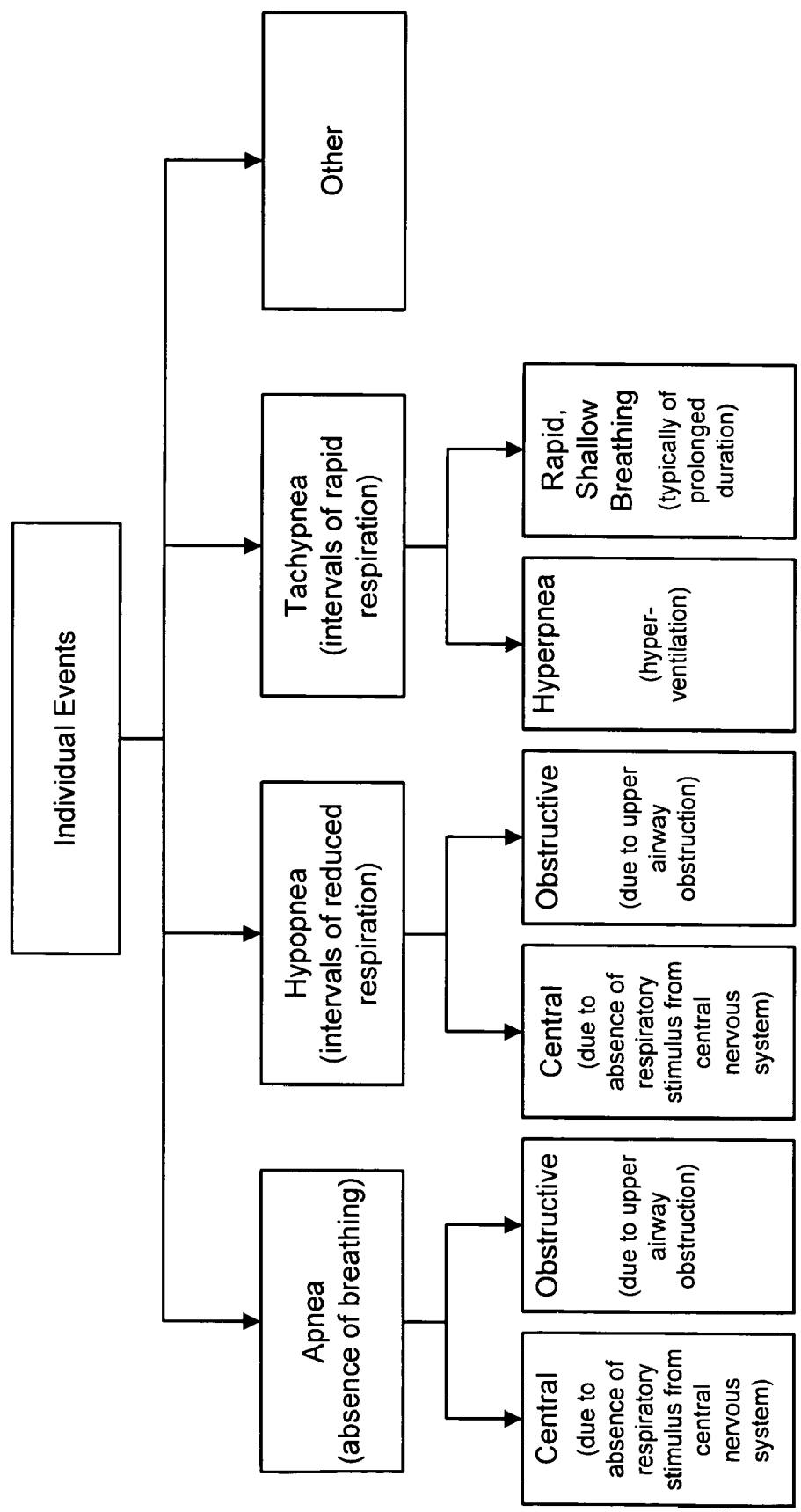
FIGS. 24 and 25 are charts illustrating disordered breathing events that can be detected and treated in accordance with embodiments of the invention.
Figure 25:
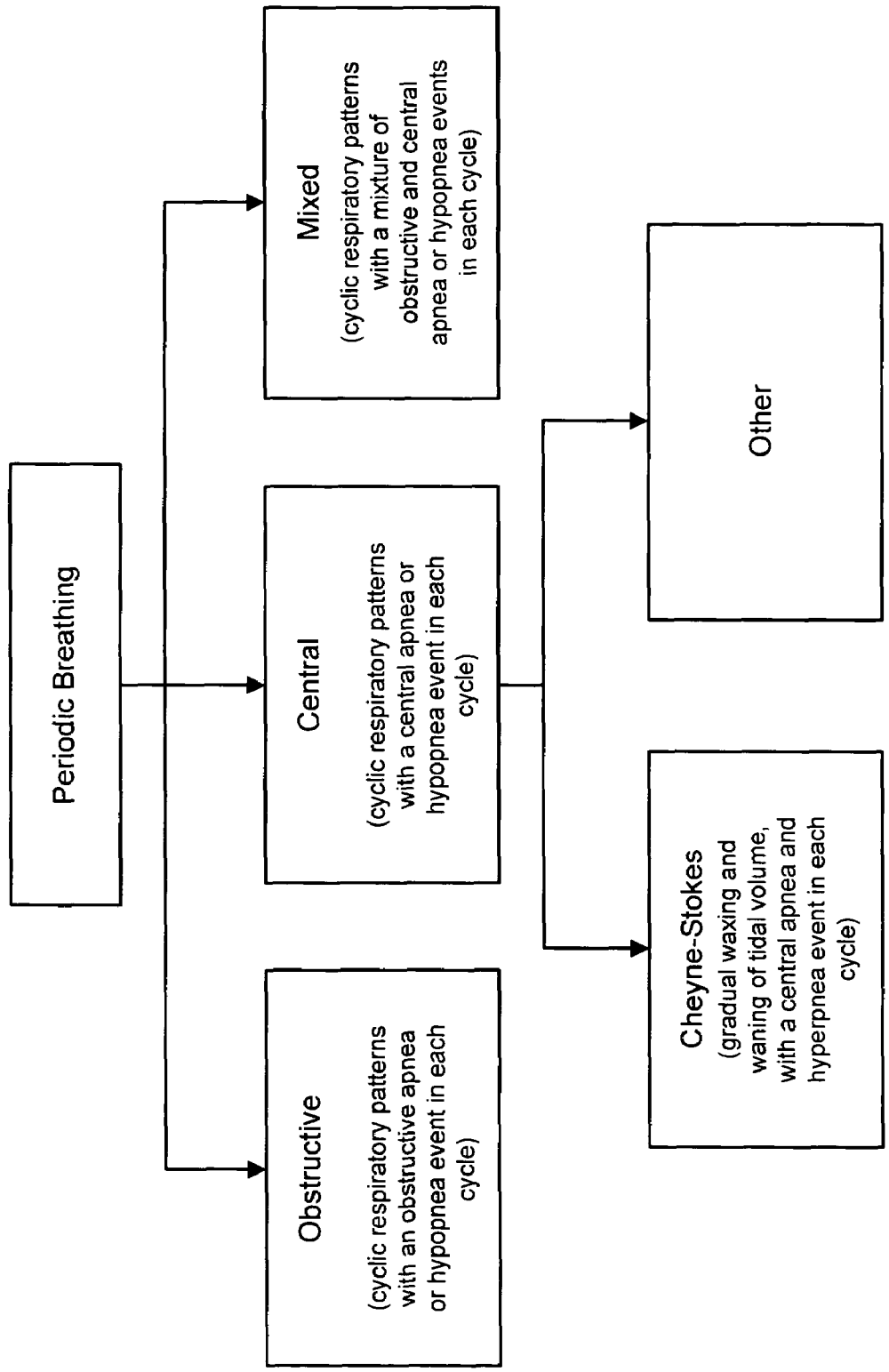

FIGS. 24 and 25 provide charts illustrating classification of individual disordered breathing events and series of periodically recurring disordered breathing events, respectively. As illustrated in FIG. 24, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 24, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

Figure 26:
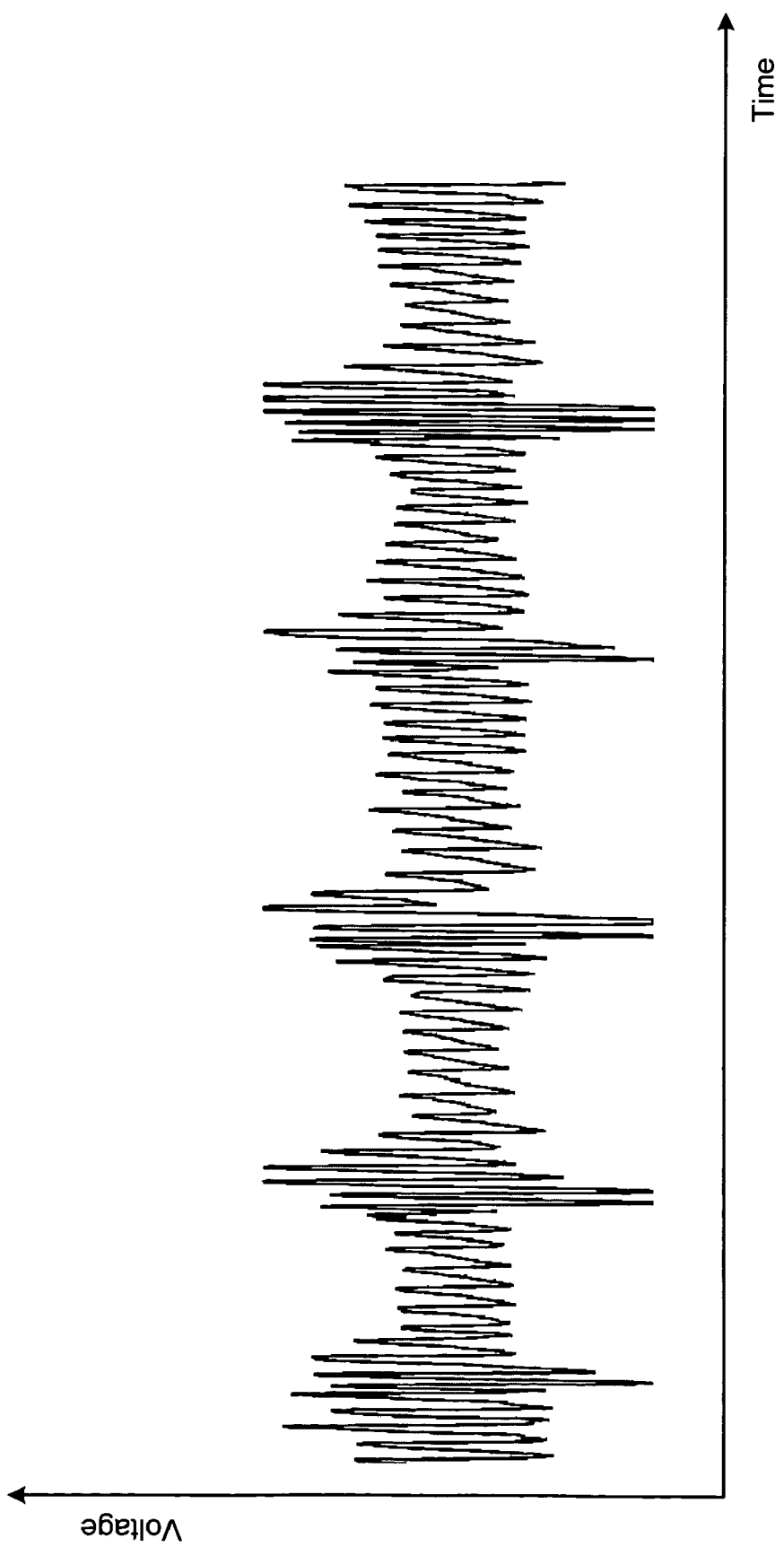
FIGS. 26 and 27 are a respiration graphs illustrating periodic breathing and Cheyne-Stokes respiration, respectively.
Figure 27:
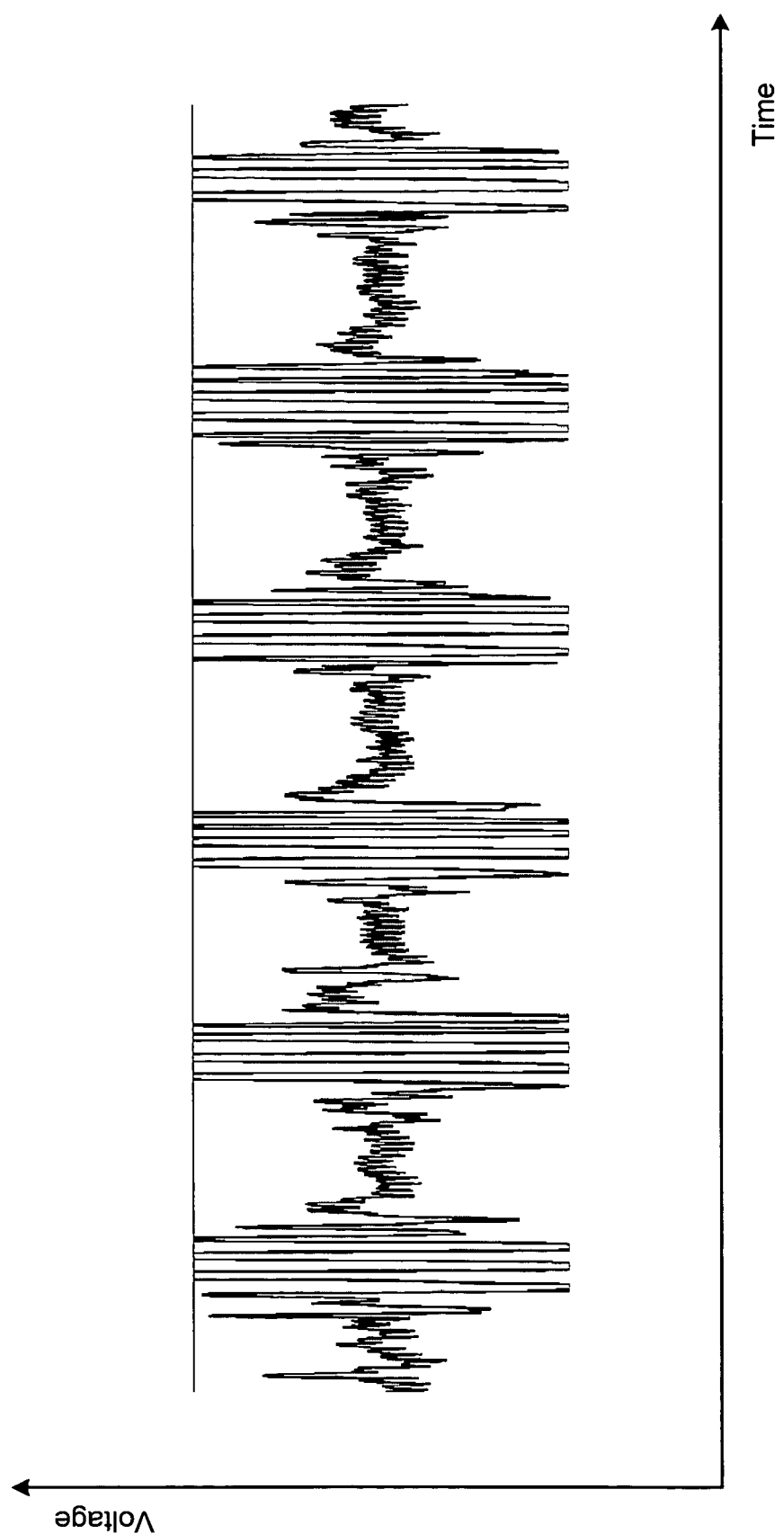

FIG. 25 illustrates of combinations of periodically recurring disordered breathing events that may be classified by the disordered breathing therapy system described herein. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle, as illustrated in FIG. 26. Cheyne-Stokes is a particular type of periodic breathing involving a gradual waxing and waning of tidal volume and having a central apnea and hyperpnea event in each cycle, as illustrated in FIG. 27. Other manifestations of periodic breathing are also possible. Disordered breathing episodes may be classified based on the characteristic respiration patterns associated with particular types of disordered breathing.

Figures 28A, 28B, 28C, 28D, 28E:
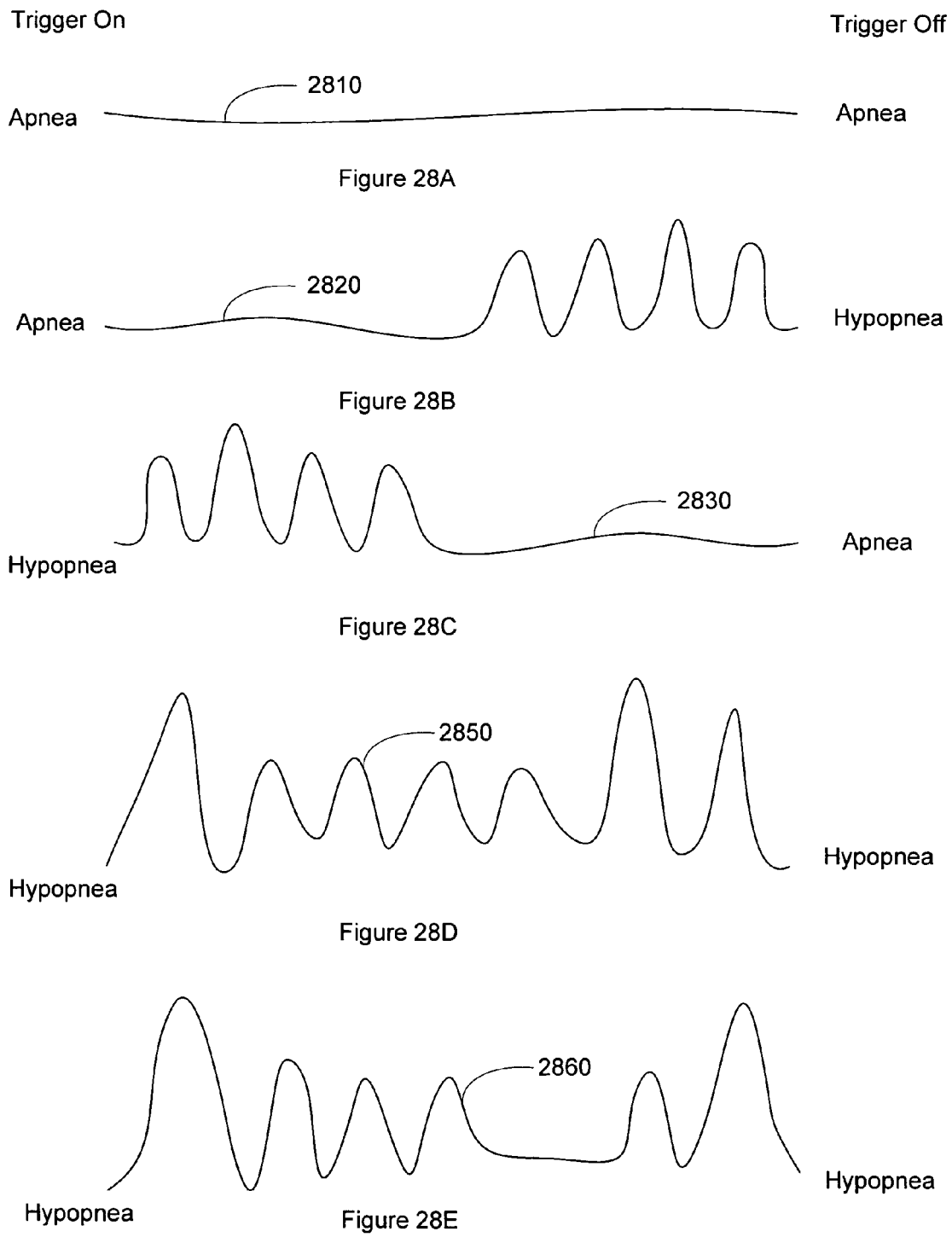
FIGS. 28A-28E are graphs illustrating disordered breathing events comprising a mixture of apnea and hypopnea respiration cycles.

As illustrated in FIGS. 28A-E, a respiration pattern detected as a disordered breathing episode may include only an apnea respiration cycle 2810 (FIG. 28A), only hypopnea respiration cycles 2850 (FIG. 28D), or a mixture of hypopnea and apnea respiration cycles 2820 (FIG. 28B), 2830 (FIG. 28C), 2860 (FIG. 28E). A disordered breathing event 2820 may begin with an apnea respiration cycle and end with one or more hypopnea cycles. In another pattern, the disordered breathing event 2830 may begin with hypopnea cycles and end with an apnea cycle. In yet another pattern, a disordered breathing event 2860 may begin and end with hypopnea cycles with an apnea cycle in between the hypopnea cycles.

Figure 29:
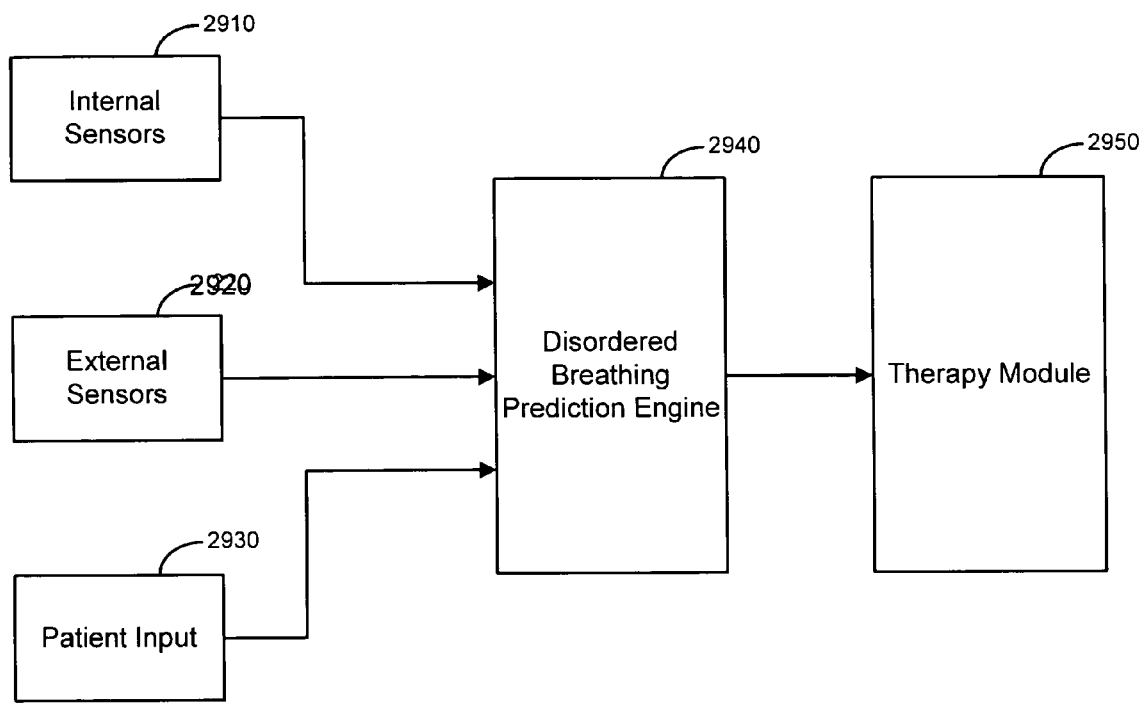
FIG. 29 is a block diagram of a system for disordered breathing prediction in accordance with embodiments of the invention.

A disordered breathing prediction system, illustrated in FIG. 29, may use patient-internal sensors 2910 to detect physiological conditions affecting the patient. For example, the system may detect heart rate, tidal volume, and/or other physiological signals using an intracardiac electrocardiogram (EGM) signal detector and transthoracic impedance sensor that are part of an implanted cardiac rhythm management system such as a cardiac pacemaker or defibrillator.

The system may further use patient-external sensors 2920 and detect physiological or contextual conditions using signals from the external sensors 2920. In one scenario whether the patient is snoring may be useful in predicting disordered breathing. Snoring noises may be sensed using an external microphone or an implanted accelerometer. Signals representing the snoring noises may be transmitted from the sensors to the system and used to detect that the patient is snoring. In another situation, temperature and humidity may be factors in the patient's disordered breathing. Signals from temperature and humidity sensors may be used to aid in the prediction of disordered breathing.

Additionally, the system may use information input 2930 by the patient to inform the disordered breathing prediction system of patient conditions. In various embodiments, the patient's medical history, self-described medication use, alcohol or tobacco use, day-time sleepiness, or perceptions of sleep quality over the past few nights may be useful in connection with the disordered breathing prediction.

Signals from one or more of the internal sensors 2910, external sensors 2920, and patient input 2930 may be coupled to a disordered breathing prediction engine 2940 for prediction analysis. In one example, the conditions associated with disordered breathing may be sensed and processed using implantable sensors 2910 and the prediction analysis performed by an external disordered breathing prediction engine 2940. Some or all of the implantable sensors 2910 may have remote communication capabilities, such as a wireless proprietary or a wireless Bluetooth communications link. The wireless communications link couples the implantable sensor or sensors 2910 to the external disordered breathing prediction engine 2940. Electrical signals representing conditions associated with disordered breathing are produced by the implantable sensors 2910 and transmitted to the external disordered breathing prediction engine 2940.

In another example, a disordered breathing prediction system is configured as an implantable therapy device incorporating a disordered breathing prediction engine 2940 and one or more external sensors 2920. Signals representing the detected conditions may be transmitted from the external sensors to the prediction engine 2940 over a wireless communication link.

In yet another example, internal sensors 2910 may be coupled to an internal prediction engine 2940 using a lead system. Various combinations of internal sensors 2910, external sensors 2920, and patient input devices 2930 coupled through wireless or wired connections to the prediction engine 2940 are possible.

Each of the conditions listed in Table 1 may serve a variety of purposes in predicting disordered breathing. Various subsets of the conditions listed in Table 1 may be detected as predisposing conditions, precursor conditions, and/or verification conditions useful in the prediction of disordered breathing. In one example, information regarding sleep onset may be employed in prediction of sleep disordered breathing. A subset of the conditions listed in Table 1 may be used to detect whether the patient is asleep and to track the various stages of sleep. Another subset of the conditions may be employed to detect and classify disordered breathing episodes. Table 3 below provides further examples of how the physiological and contextual conditions of the patient may be used in disordered breathing prediction.

TABLE 3

| Condition | Examples of how condition is used in disordered breathing prediction |
| --- | --- |
| Heart rate | Decrease in heart rate may indicate disordered breathing episode. |
| | Decrease in heart rate may indicate the patient is asleep. |
| | Increase in heart rate may indicate autonomic arousal from disordered breathing. |
| Heart rate variability | May be used to determine sleep state |
| Ventricular filling pressure | May be used to identify/predict pulmonary congestion associated with respiratory disturbance. |
| Blood pressure | Swings in on-line blood pressure measures are associated with apnea. |
| Snoring | Snoring is associated with a higher incidence of obstructive sleep apnea and may be used to detect disordered breathing. |
| Respiration signals/respiration patterns | Respiration patterns may be used to detect disordered breathing episodes. |
| | Respiration patterns may be used to determine the type of disordered breathing. |
| | Respiration patterns may be used to detect that the patient is asleep. |
| | Hyperventilation may be used to predict disordered breathing. |
| | Previous episodes of disordered breathing may be used to predict further episodes. |
| | One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/hypopnea episodes. |
| Blood alcohol content | Alcohol tends to increase incidence of snoring & obstructive apnea. |
| Adrenalin | End of apnea associated with a spike in blood adrenaline. |
| BNP | A marker of heart failure status, which is associated with Cheyne-Stokes Respiration |
| C-Reactive Protein | A measure of inflammation that may be related to apnea. |
| Drug/Medication/Tobacco use | These substances may affect incidence of both central & obstructive apnea. |
| Muscle atonia | Muscle atonia may be used to detect REM and non-REM sleep. |
| Eye movement | Eye movement may be used to detect REM and non-REM sleep. |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep. |
| | Posture may be a condition predisposing the patient to episodes of disordered breathing. |
| Activity | Patient activity may be used in relation to sleep detection. |
| Sleep stage | NREM sleep is associated with a higher incidence of DB episodes |
| Location | Patient location may used to determine if the patient is in bed as a part of sleep detection. |
| Altitude | Lower oxygen concentration associated with high altitudes predisposes patients to more central apnea |

Figure 30:
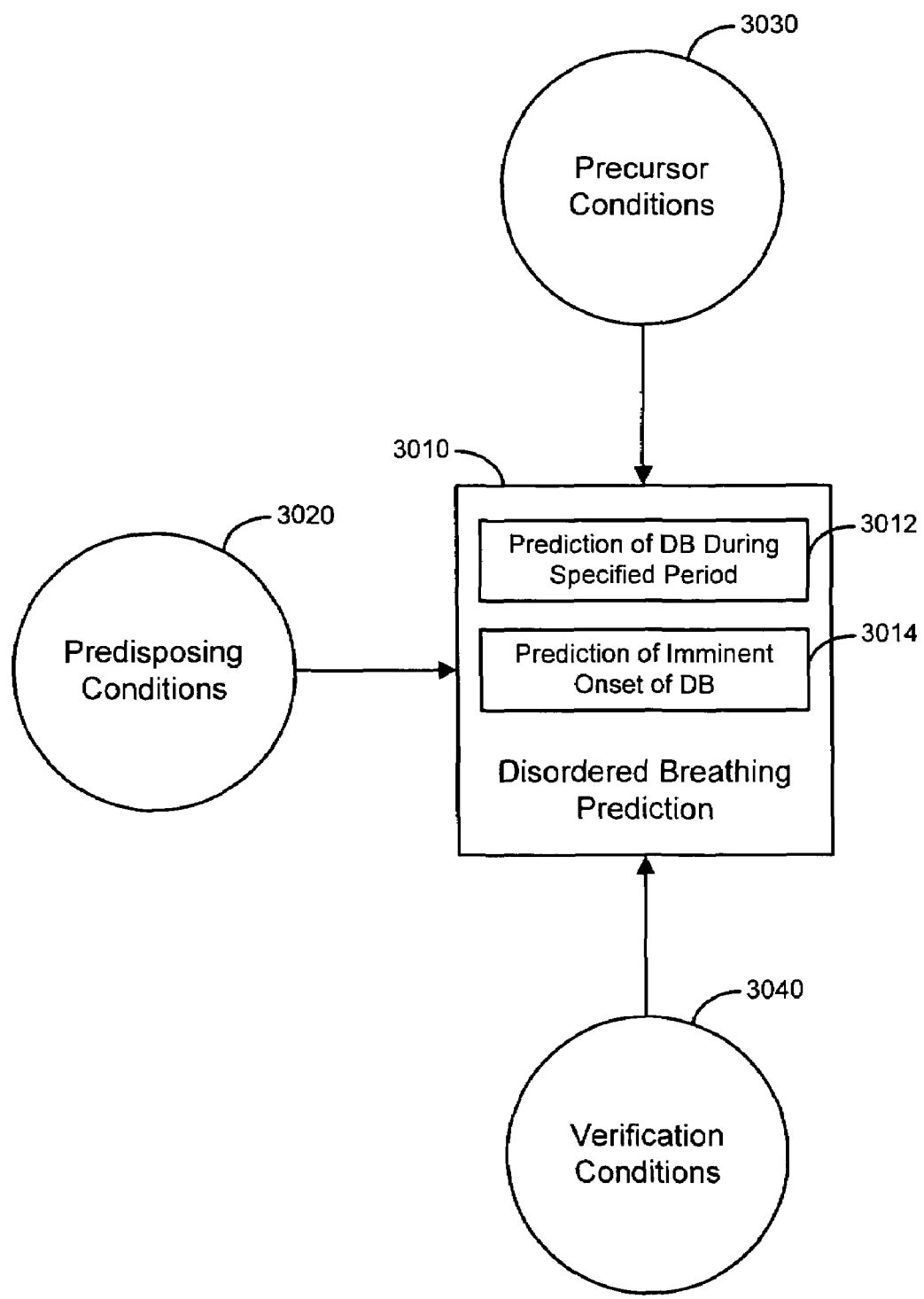
FIG. 30 is a diagram illustrating prediction of disordered breathing in accordance with embodiments of the invention.

FIG. 30 conceptually illustrates how conditions, such as those listed in Tables 1-3, may be used in predicting disordered breathing according to embodiments of the invention. In one embodiment, the system tracks one or more of the patient conditions to predict 3010 disordered breathing. For example, over the course of a period of time, e.g., at least about a 16 hour window preceding and including the patient's historical sleep time, the system may track one or more conditions to determine the presence and/or level of each particular condition.

In one implementation, the system tracks conditions that have been determined to predispose 3020 the patient to an attack of disordered breathing. Predisposing conditions represent conditions statistically associated with an onset of disordered breathing. Prediction of disordered breathing based on predisposing conditions may be performed in real-time. The presence of one or more predisposing conditions consistent with prediction criteria may indicate that disordered breathing is likely to occur within the next time period, such as during the current sleep period, or during the next time period of about eight hours. For example, the conditions predisposing the patient to disordered breathing may include the air pollution index of the patient's environment downloaded from an air quality website, recent tobacco use reported by the patient, the degree of the patient's pulmonary congestion detected by an implanted transthoracic impedance sensor, as well as other internally or externally detected predisposing conditions.

Additionally, or alternatively, the system may use previous episodes of disordered breathing to determine that the patient is predisposed to further episodes of disordered breathing within particular time period, such as during the night. For example, previous episodes of disordered breathing during a first interval within a sleep period may be an indication that additional episodes are likely to occur in a second and subsequent interval within the same sleep period. Therefore, the system may use the type, duration, frequency, and severity of the previous disordered breathing episodes to inform the disordered breathing prediction analysis.

The occurrence of one type of disordered breathing may be predictive of another type. For example, the occurrence of obstructive sleep apnea episodes may be used to predict that central sleep apnea will occur later during the night. In another example, the occurrence of a hypopnea episode may be used to predict an apnea episode. Quantification of the severity, frequency, and duration of disordered breathing may be accomplished using any of a number of disturbed breathing measures, including, for example, percent time in disordered breathing and the apnea/hypopnea index.

A further example of a condition predisposing a patient to hypopnea or apnea is body posture. A supine posture is more likely to result in obstruction of the upper airway and can be used to predict episodes of obstructive hypopnea and apnea. Posture sensing may be implemented using a position sensitive switch coupled to the patient. Posture and/or torso orientation sensing may be accomplished, for example, using an implantable or external multiaxis accelerometer.

The patient's location may also be useful in prediction of disordered breathing. Because disordered breathing often occurs during sleep, the patient may be more likely to experience disordered breathing if the patient is in bed. A bed proximity sensor may be implemented by placing a beacon transmitter on the patient's bed. Receiver circuitry on or in the patient, for example, incorporated in the patient's pacemaker, receives the beacon signal and determines that the patient is in bed.

Conditions that predispose the patient to disordered breathing 3020 are conditions that, if detected, indicate the likelihood that one or more episodes of disordered breathing will occur during the next time period, such as over the course of the night. Based on predisposing conditions 3020, an onset of disordered breathing may be predicted 3012 to occur within a time window that may include several hours, for example. A second set of factors, denoted herein as precursor conditions 3030, may be used to predict 3014 an impending onset of disordered breathing. Precursor conditions 3030 indicate that an episode of disordered breathing is imminent. Prediction of disordered breathing may be performed in real-time. The presence of precursor conditions consistent with prediction criteria may be used to predict that disordered breathing will occur within a time window that may be measured in terms of minutes or seconds, for example, within about the next five minutes.

Precursor conditions 3030 indicative of an impending onset of disordered breathing may include, for example, pre-apnea or pre-hypopnea conditions. In one embodiment, decreased levels of $CO_2$ in a particular patient may be causal to central apnea. Therefore, a condition of pre-apnea may be detected when a patient's $CO_2$ level, as measured by an external $CO_2$ sensor, falls below a selected level, indicating the impending onset of an apnea episode.

In another embodiment, a patient's heart rate variability may be significantly altered before, during, and after episodes of apnea. Heart rate variability may be used, for example, as a precursor condition to predict an impending episode of disordered breathing.

In yet another embodiment of the invention, a pre-disordered breathing condition, e.g., pre-apnea or pre-hypopnea, may be detected by analyzing the patient's respiration patterns or the morphology of a respiration signal. Respiration cycles just prior to an apnea event may exhibit a characteristic pattern. For example, an apnea event for many patients is preceded by a period of hyperventilation with a number of rapid, deep breaths. The pattern of hyperventilation may be detected by analyzing patient's transthoracic impedance signal to determine respiration rate and tidal volume.

Cheyne-Stokes respiration and some apnea/hypopnea episodes may exhibit a crescendo-decrescendo respiration pattern. The crescendo-decrescendo respiration pattern produces hyperventilation during the crescendo stage and hypoventilation during the decrescendo phase. Hyperventilation, secondary to pulmonary congestion, drives arterial partial pressure of carbon dioxide down. A decrease in arterial partial pressure of carbon dioxide below an apnea level may be a causal mechanism for central apnea. According to one embodiment of the invention, detection of an impending onset of disordered breathing may be implemented by detecting a series of increasing tidal volumes followed by a series of decreasing tidal volumes.

For some patients, disordered breathing occurs at regular intervals, allowing the periodicity of the disordered breathing episodes to be used as a precursor condition. If disordered breathing episodes of the patient occur at regular intervals, the next episode of disordered breathing may be predicted based on the time elapsed since the last episode was detected. Precursor conditions 3030 may be analyzed individually, or in combination with one or more predisposing conditions 3020, to predict the impending onset of a disordered breathing episode.

Snoring is an example of a pre-apnea or pre-hypopnea condition. In many, patient snoring, or more generally any abnormal airflow in the upper airway detectable via acoustic means, precedes more significant sleep disordered breathing conditions such as hypopnea or apnea.

Yet another group of conditions may be used to verify a prediction of disordered breathing. For example, after a prediction of disordered breathing is made, one or more verification conditions 3040 may be checked to confirm the prediction. The verification conditions, as well as the physiological and contextual conditions used in the first stage of the prediction analysis, may be highly patient specific.

In one example, a characteristic pattern of respiration is a reliable predictor of disordered breathing in a particular patient only when the patient is supine. If the prediction is made while the patient not supine, normal variations in respiration cycles in this particular patient may lead to an erroneous prediction of disordered breathing. Thus, before disordered breathing is predicted, the posture sensor signal is checked to verify that the patient is supine. If the patient is supine and the patient's respiration cycles are consistent with criteria indicating that disordered breathing is likely, the prediction may be made.

In another example, the patient is known to suffer from episodes of apnea during sleep. The patient's sleep apnea may be predicted using a number of physiological and contextual conditions. The prediction of sleep apnea may be made after assessing that the patient's posture and location are consistent with sleep. Before a prediction of sleep apnea is made, the system confirms that the patient is lying down in bed by checking the signal from an implantable posture sensor and a bed proximity sensor.

Figure 31:
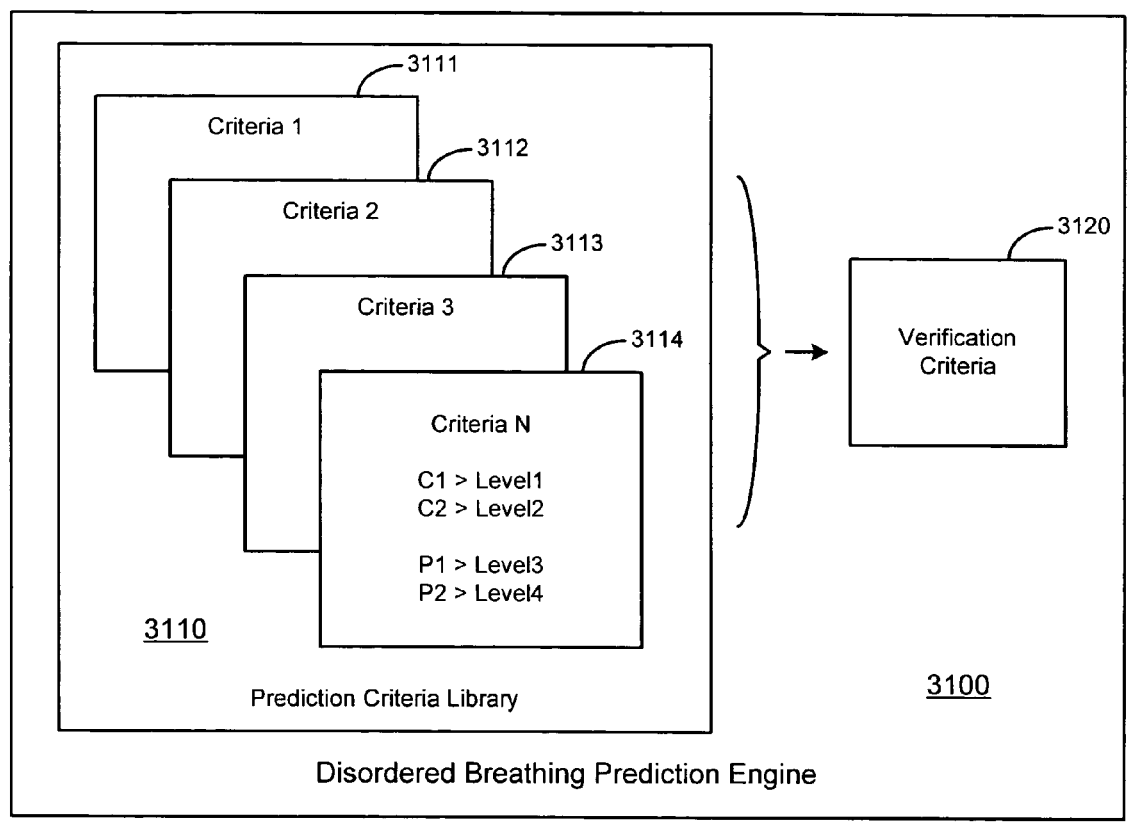
FIG. 31 is a block diagram of a disordered breathing prediction engine in accordance with embodiments of the invention.

The operation of a disordered breathing prediction engine 3100, according various to embodiments, is conceptually illustrated in the block diagram of FIG. 31. Periodically, one or more conditions are detected and compared to a library 31 of prediction criteria. The prediction criteria library 3110 may incorporate one or more sets of prediction criteria 3111, 3112, 3113, 3114. Each of these sets of criteria may be compared to the detected conditions. If the criteria of a prediction criteria set 3111, 3112, 3113, 3114 are substantially consistent with the detected conditions, a preliminary disordered breathing prediction may be made.

In various embodiments, the prediction criteria sets 3111, 3112, 3113, 3114 represent one or more condition thresholds associated with an onset of disordered breathing. In one embodiment, the level of one or more conditions may be compared to the prediction criteria sets 3111, 3112, 3113, 3114. If the levels of the one or more conditions are substantially equal to or greater than the thresholds specified by a prediction criteria set 3111, 3112, 3113, 3114, a preliminary prediction of disordered breathing is made.

The example above and the examples that follow are described in terms of a condition being consistent with prediction criteria when the condition exceeds a prediction criteria threshold. However, it will be understood by those skilled in the art that different threshold requirements may be defined for different conditions. For example, one condition may be defined to be consistent with a prediction criterion when the condition exceeds a prediction criterion threshold. Another condition may be defined to be consistent with a prediction criterion threshold when the condition falls below the threshold. In yet another example, a condition may be defined to be consistent with the prediction criterion when the condition falls within a specified range of values. A detected condition may be consistent with a particular prediction criteria in terms of a timing, a rate of change or a maximum or minimum value of the condition, for example.

In the example provided in FIG. 31, the prediction criteria N 3114 involves two contextual conditions, C1 and C2, and two physiological conditions, P1 and P2. In this particular example, if conditions C1, C2, P1, and P2 exceed levels Level1, Level2, Level3, and Level4, respectively, the patient is likely to experience disordered breathing during the night. Therefore, when conditions C1, C2, and P1, P2 reach the levels specified in criteria N 3114, preliminary prediction of disordered breathing is made.

In another embodiment of the invention, the relationships between the detected conditions are analyzed to predict disordered breathing. In this embodiment, the disordered breathing prediction may be based on the existence and relative values associated with two or more conditions. For example, if condition A is present at a level of x, then condition B must also be present at a level of f(x before a disordered breathing prediction is made.

In yet another embodiment of the invention, the estimated probability, $P(C_n)$, that disordered breathing will occur if a particular condition level is detected may be expressed as a function of the ratio of the number of times disordered breathing occurred within a selected time interval following the detection of the particular condition level to the total number of observed occurrences of the condition level. The probability that disordered breathing will occur, $P(C_n)$, is compared to a threshold probability level to make the disordered breathing prediction. Other methods of calculating the estimated probability are also possible.

The prediction of disordered breathing may be based on the convergence or divergence of a number of conditions occurring within the same time period. In this situation, a composite probability score may be computed as a combination of the individual probabilities. In one embodiment, the probabilities are combined by adding the condition probabilities after multiplying each of the condition probabilities by a weighting factor. For example, if the disordered breathing prediction is based on four substantially simultaneous conditions, $C_1$, $C_2$, $C_3$, and $C_4$, the total probability score $PS_T$ may be calculated as:

$$PS_T = A \times P(C_1) + B \times P(C_2) + C \times P(C_3) + D \times P(C_4), \qquad [1]$$

where A, B, C, and D are scalar weighting factors that may be used to estimate the relative importance of each of the conditions $C_1$, $C_2$, $C_3$, and $C_4$. If the probability score exceeds a selected prediction criteria threshold, then disordered breathing is predicted.

Although the above process describes combining the estimated probabilities for each condition by adding each of the estimated probabilities, other methods are also possible. For example, a detected condition may operate against a prediction of disordered breathing. In this situation, the estimated probability, $P_n(C_n)$, that disordered breathing will not occur if a particular condition level is detected may be expressed as a function of the ratio of the number of times disordered breathing did not occur within a selected time interval following the detection of the particular condition level to the total number of observed occurrences of the condition level. This value may be subtracted from the total to determine the probability score. Non-linear methods of combining the estimated probabilities to arrive at a composite probability are also possible.

If the conditions affecting the patient are consistent with a prediction of disordered breathing, the prediction may be verified by comparing one or more verification conditions to verification criteria. If the verification conditions are consistent with the verification criteria, a prediction of disordered breathing is made.

In the embodiments described above, predictions of disordered breathing are based upon comparisons of one or more detected conditions to sets of prediction criteria. The initial data from which the initial prediction criteria sets are formed may be derived from past observations taken from population data, or from data collected from a particular patient. The initial prediction criteria sets may then be modified as additional data are collected from the patient.

In one embodiment, an estimated accuracy for the prediction criteria is updated for every prediction event. The estimated positive predictive value (PPV) for a prediction criteria set N may be expressed as:

$$PPV_N = \frac{TP}{TP+FP} \quad [2]$$

where TP (true positive) is the number of times the prediction criteria set successfully predicted disordered breathing, and FP (false positive) is the number of times the prediction criteria erroneously predicted disordered breathing.

If the estimated accuracy of prediction criteria set N, $PPV_N$, falls below a predetermined level, for example, 0.7, the prediction criteria set N may be modified. In one embodiment, a possible prediction criteria set is formed, for example, by modifying the threshold level of one or more of the conditions represented by the original prediction criteria set N. In one embodiment, each threshold in the original prediction criteria set N is modified by an incremental value, to make the prediction criteria set more accurate.

In another embodiment, conditions represented in the original prediction criteria set N are compared to the conditions that are present just prior to a disordered breathing occurrence to determine how the modification for the possible prediction criteria set should be implemented. For example, if the level of a particular condition just prior to the occurrence shows a relatively large variation just prior to the disordered breathing episode, but the levels of other conditions remain constant, then only the changing level may be modified in the possible prediction criteria set.

Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, and the accuracy original prediction criteria set N remains below 0.7, the possible prediction criteria set may replace the original prediction criteria set N in the prediction criteria library.

According to various embodiments, new prediction criteria sets may be added to the prediction criteria library. In accordance with these embodiments, if a disordered breathing episode occurs without prediction, the levels of the detected conditions prior to the disordered breathing episode are saved as a possible prediction criteria set. Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, the possible prediction criteria set may be added to the prediction criteria library.

The system may also be adjusted to provide increasingly sensitive disordered breathing prediction criteria sets, according to various embodiments. The estimated sensitivity for a prediction criteria set N may be expressed as:

$$Sensitivity_N = \frac{TP}{TP+FN} \quad [3]$$

where TP (true positive) is the number of times the prediction criteria successfully predicted disordered breathing, and FN (false negative) is the number of times the prediction criteria erroneously predicted that disordered breathing would not occur.

In one embodiment, if the prediction criteria accuracy for the prediction criteria set N becomes larger than a selected number, for example, 0.9, then the threshold levels of one or more of the conditions represented in the prediction criteria set N may be adjusted to provide enhanced sensitivity.

In one example, the threshold level of each condition represented in the prediction criteria set N is modified by an incremental value, thus making the prediction criteria set N more sensitive. In another embodiment, conditions represented in the prediction criteria set N are compared to the conditions that are present just prior to a disordered breathing occurrence to determine how the modification of the prediction criteria set N should be implemented. In yet another embodiment, a condition threshold level that is modified is based upon the relative importance of the condition in the overall prediction criteria. In another example, if the level of a particular condition is changing just prior to the occurrence of the disordered breathing episode, but the levels of other conditions remain constant, only the changing condition may be modified.

Following adjustment by any of the processes described above, the adjusted prediction criteria set may be designated as possible prediction criteria set. Each time the possible prediction criteria set is satisfied, no prediction of disordered breathing is made, however, the accuracy of the possible prediction criteria set is updated, for example, using Equation 2 or 3. If the accuracy of a possible prediction criteria set reaches a selected level, for example, 0.7, the possible prediction criteria set may be added to the prediction criteria library.

The system may also be adjusted to provide improved specificity or negative predictive value (NPV) of disordered breathing prediction criteria in a manner similar to the adaptive method described previously. Calculation of specificity and NPV for a prediction criteria N may be accomplished using equations 4 and 5 below.

$$Specificity_N = \frac{TN}{TN+FP} \quad [4]$$

$$NPV_N = \frac{TN}{TN+FN} \quad [5]$$

where TN (true negative) is the number of times the prediction criteria successfully predicted the absence of disordered breathing, FP (false positive) is the number of times the prediction criteria erroneously predicted disordered breathing and FN (false negative) is the number of times the prediction criteria erroneously predicted the absence of disordered breathing.

Figure 32:
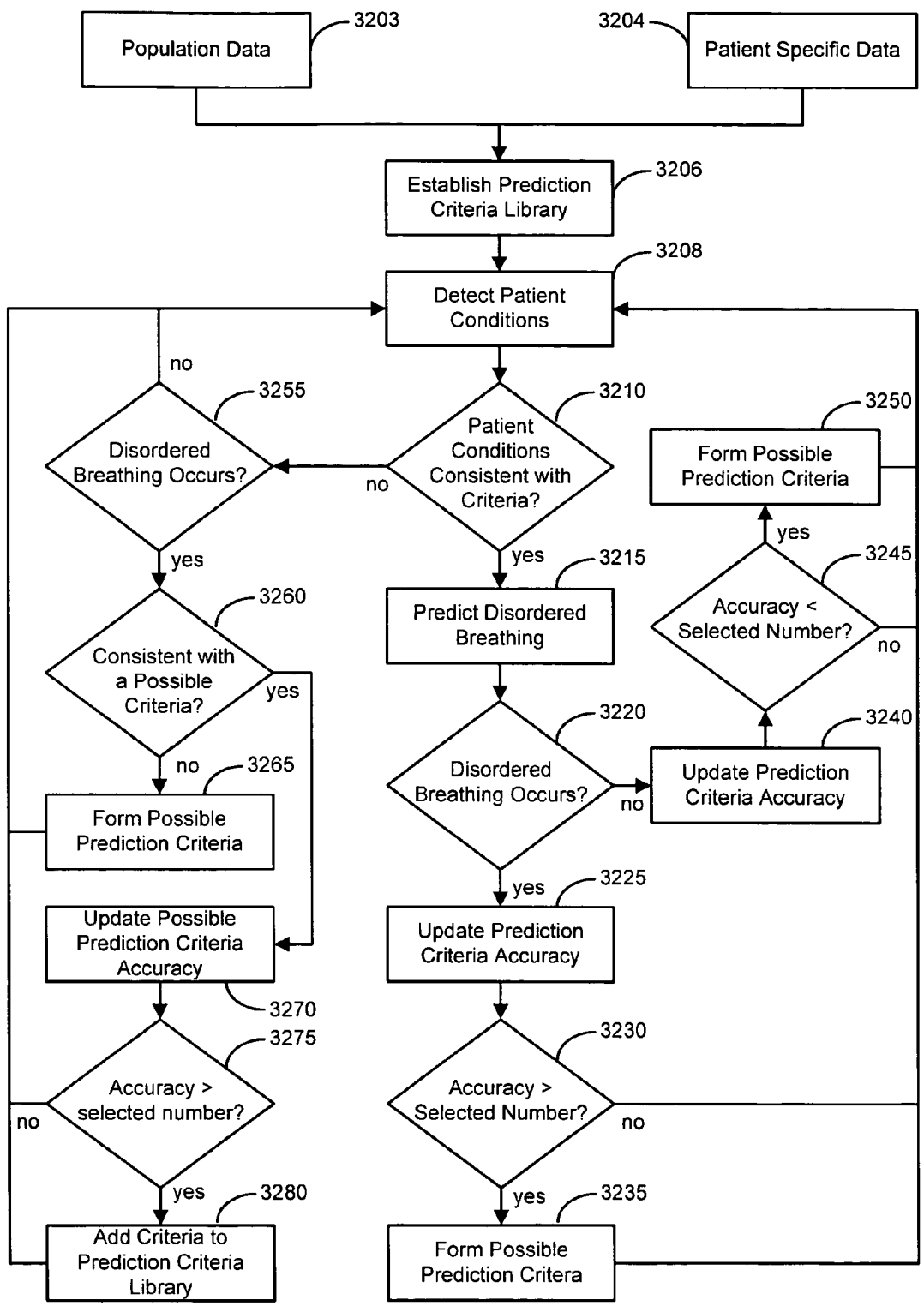
FIG. 32 is a flowchart illustrating a method for establishing and updating a prediction criteria library according to embodiments of the invention.

The flowchart of FIG. 32 illustrates a method for establishing and updating the prediction criteria library according to embodiments of the invention. Previous observations of disordered breathing may be assimilated from population data 3202 or from past observation of the specific patient 3204.

One or more prediction criteria sets are determined and organized in a prediction criteria library 3206.

Conditions associated with disordered breathing are periodically detected 3208 and compared to the prediction criteria sets in the prediction criteria library. If the levels of the detected conditions are consistent 3210 with any of the prediction criteria sets in the library, then disordered breathing is predicted 3215. Within a time window following the disordered breathing prediction, the system determines if disordered breathing occurs 3220.

If disordered breathing occurs 3220, the prediction criteria accuracy of the prediction criteria set used for the disordered breathing prediction is updated 3225. If the updated prediction criteria accuracy is greater 3230 than a selected number, then a possible prediction criteria set is formed 3235. The possible prediction criteria set may be formed, for example, by substituting more sensitive condition levels when compared to the original prediction criteria set.

If disordered breathing is not detected 3220 following the prediction, then the prediction criteria set accuracy is updated 3240. If the prediction criteria set accuracy decreases 3245 below a selected number, then a possible prediction criteria set 3250 is formed. The possible prediction criteria set may be formed, for example, by substituting more stringent condition levels to produce a more accurate prediction.

If the detected conditions are not consistent 3210 with any of the prediction criteria sets in the prediction criteria library, disordered breathing is not predicted. Within a time window following the disordered breathing prediction, the system determines if disordered breathing occurs 3255. If disordered breathing occurs 3255, then the system checks to see if the conditions are consistent 3260 with any of the possible prediction criteria sets. If the conditions are not consistent 3260 with any of the possible prediction criteria sets, a possible prediction criteria set is formed 3265.

If the conditions are consistent 3260 with a possible criteria set, the possible prediction criteria set accuracy is updated 3270. If the possible prediction criteria accuracy increases beyond a selected number 3275, the possible prediction criteria set is added 3280 to the prediction criteria library.

Figure 33A:
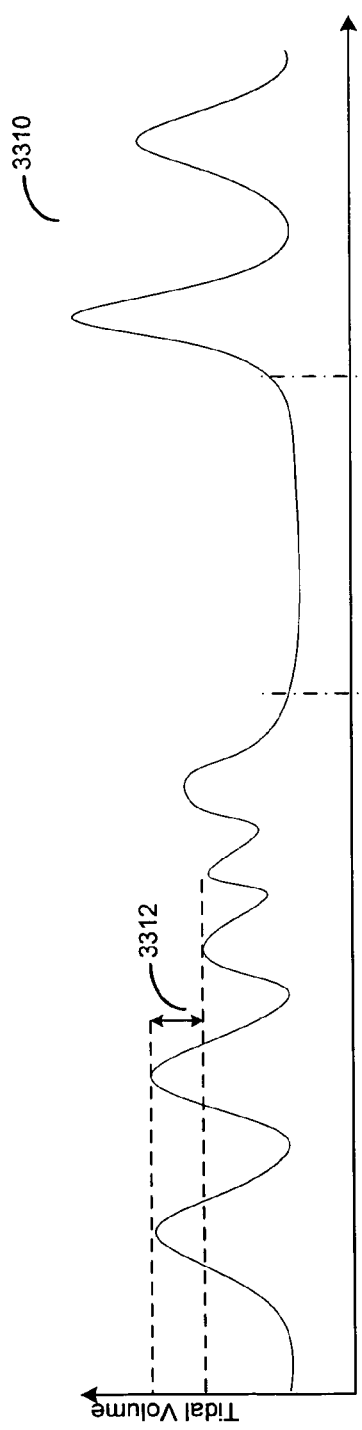
FIGS. 33A-33C illustrate representative graphs of tidal volume, heart rate, and activity level during disordered breathing prediction in accordance with embodiments of the invention.
Figure 33B:
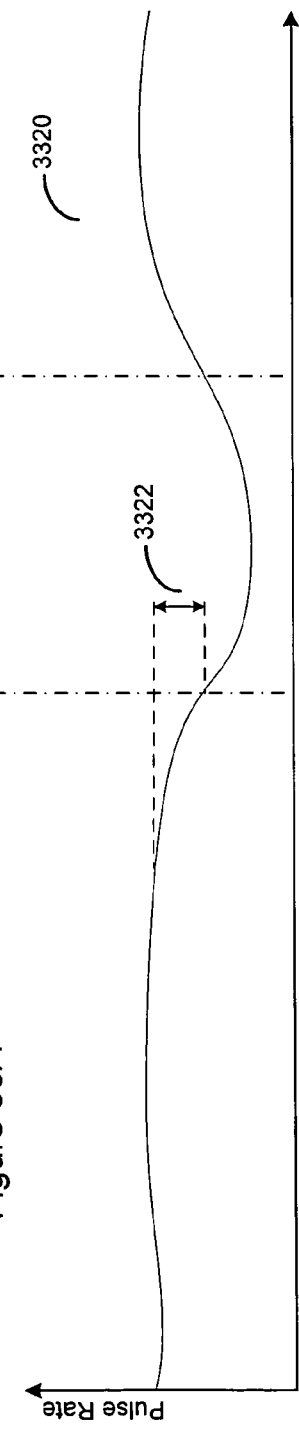
Figure 33C:
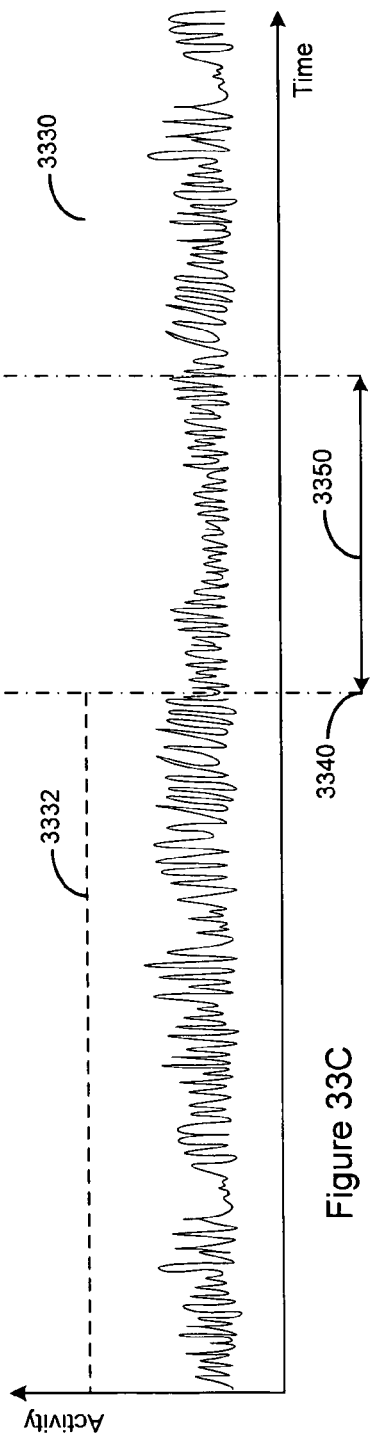

Representative graphs of the patient's tidal volume 3310, heart rate 3320, and activity level 3330 during disordered breathing prediction are illustrated in FIGS. 33A-33C. In this example, the patient's tidal volume 3310 exhibits a characteristic decrease 3312 just before the onset 3340 of an episode of disordered breathing 3350. Accordingly, a first condition threshold for disordered breathing prediction is established as a percentage drop in tidal volume. Additionally, the patient's heart rate 3320 exhibits a decrease 3322 that occurs substantially simultaneously with the decrease in tidal volume 3312. A second condition threshold for disordered breathing detection is established as a percentage drop in heart rate.

If the system detects that the percent decrease in tidal volume and the percent decrease in heart rate exceed the established thresholds, a disordered breathing prediction is made subject to verification. The disordered breathing prediction is then verified by determining that the patient's activity signal 3330, as detected by the accelerometer, is below a resting threshold 3332 and that the proximity to bed receiver indicates that the patient is in bed.

The NS therapy for disordered breathing may be initiated upon detection that the patient is asleep. Sleep determination may be performed in a variety of ways. In one example, some patients' may have regular sleep times. The NS therapy could be initiated during a patient's normal sleep time. In another example, the NS system may evaluate a number of physiological and non-physiological conditions to determine if the patient is asleep. A drop in cardiac rate, for example, is indicative of sleep. Supine posture, proximity to bed, decreased respiration, and activity are examples of conditions that may be used in sleep determination. Methods and systems for sleep detection, aspects of which may be utilized in the delivery of baroreflex therapy for disordered breathing, are described in commonly owned U.S. Pat. No. 7,189,204 (Ni et al.), and incorporated by reference herein.

As previously described, a therapy that modifies the patient's baroreflex response may be adapted for a variety of reasons. For example, the therapy may be modified to improve the efficacy of the therapy, to reduce an impact of the therapy on the patient, and/or to mitigate or avoid interactions with other therapies delivered to the patient. The therapy may be adapted based on one or more conditions affecting the patient.

Figure 34:
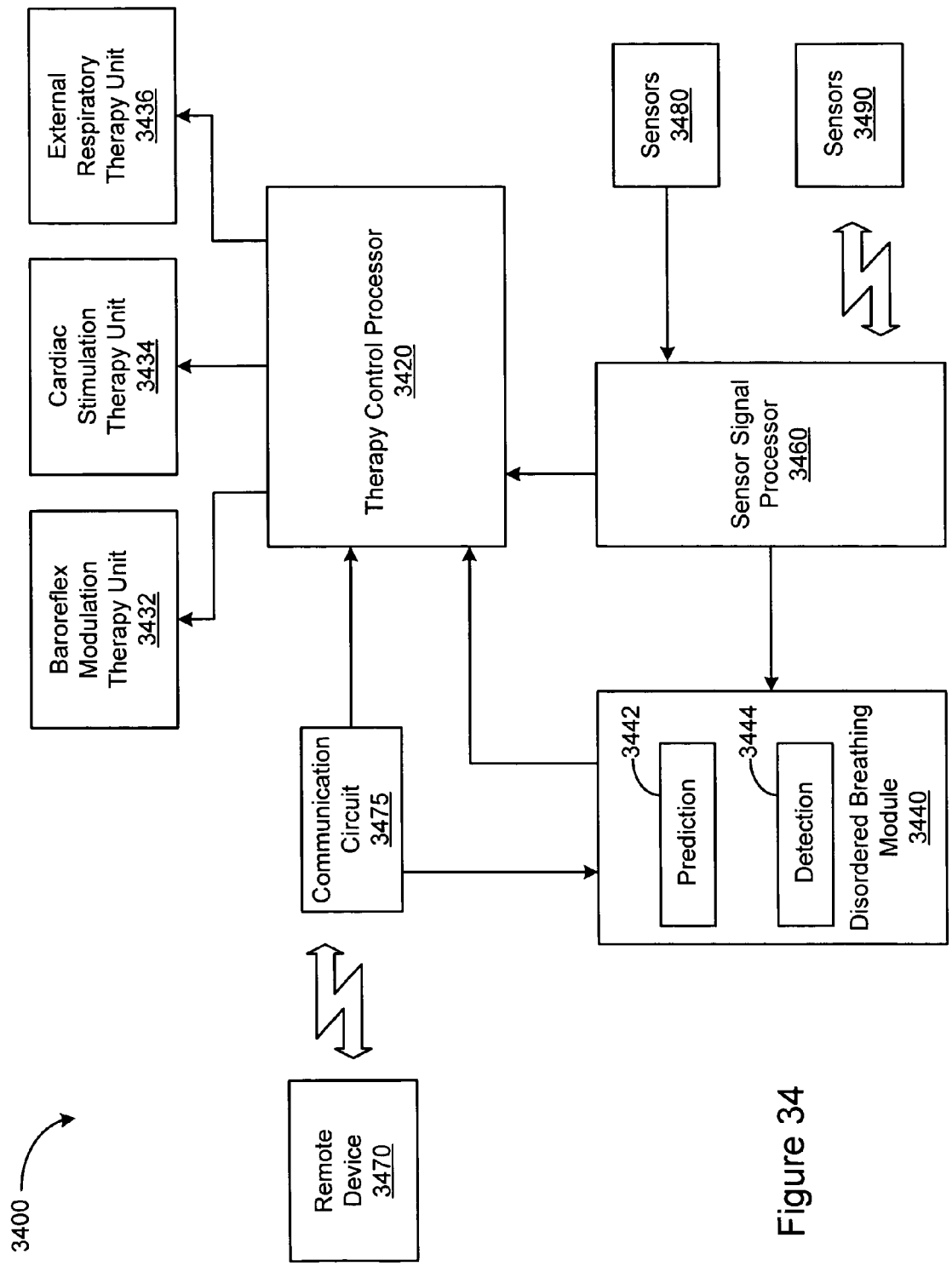
FIG. 34 is a block diagram illustrating a disordered breathing therapy system in accordance with embodiments of the invention.

FIG. 34 is a block diagram illustrating a disordered breathing therapy system 3400 including a therapy controller processor 3420 for controlling a number of therapies to treat disordered breathing. The therapies may include baroreflex modulation therapy delivered by a baroreflex modulation therapy unit 3432, cardiac stimulation therapy delivered by a cardiac stimulation therapy unit 3434, and an external respiration therapy delivered by an external respiration therapy unit 3436. The therapy system 3400 may include a disordered breathing detection/prediction module 3440. The disordered breathing module 3440 may includes circuitry for disordered breathing detection 3444 and a disordered breathing prediction engine 3442.

Patient conditions may be sensed or detected using one or more sensors 3480, 3490. A sensor signal processor 3460 may include circuitry for energizing the sensors and processing signals generated by the sensors. Communications circuitry 3475, including a wireless transceiver, may be used to communicate with remotely located sensors 3490 and or other remote devices 3470. Signals derived from the sensors 3480, 3490 and remote device 3470 may be used in the prediction and/or detection of disordered breathing, or for other purposes.

A prediction or detection of disordered breathing by the disordered breathing prediction module 3440 may be used to trigger baroreflex stimulation therapy delivered by the one or more of the therapy devices 3432, 3434, 3436 to mitigate disordered breathing. In one example, the baroreflex modulation therapy device 3432 delivers an appropriate electrical stimulation therapy through electrodes 3431 coupled to one or more baroreceptor sites in the pulmonary artery, aortic arch, ligamentum arteriosum, the coronary sinus, in the atrial and/or ventricular chambers, and/or in cardiac fat pads.

In one example disordered breathing therapy regimen, electrical stimulation of baroreceptor sites by the baroreflex modulation device 3432 may be combined with cardiac electrical stimulation therapy. For example, cardiac electrical stimulation to treat disordered breathing may include overdrive pacing at a rate exceeding an intrinsic rate or in excess of the patient's normal sleep rate. The pacing may involve any or all of the heart chambers, for example, right and left atria and right and left ventricles. The pacing may also involve bi-atrial, bi-ventricular, or multi-site pacing. In one example, the pacing pulses may be delivered to left and right atria simultaneously, or according to other timing sequences. In another example, the simultaneous or otherwise timed pacing pulses may be delivered to the left and right ventricles of the heart.

Further, delivery of the disordered breathing therapy may involve adapting a therapy involving sub-capture threshold, non-excitatory electrical stimulation of one or more heart chambers, e.g., the left and/or right ventricles, or other cardiac sites. Non-excitatory electrical stimulation may be delivered during absolute refractory periods of the cardiac tissue, for example, to improve cardiac contractility. The non-excitatory stimulation therapy may be used alone or in combination with cardiac pacing to provide a comprehensive therapy regimen for patients with CHF and disordered breathing such as Cheyne-Stokes respiration. Various approaches to delivering and adapting cardiac electrical stimulation therapy for disordered breathing are described in commonly owned U.S. Patent Application Publication Nos. 2005/0043772 and 2005/0039745, and incorporated herein by reference.

Therapy delivered to mitigate disordered breathing may be adjusted based on an assessment of the therapy. Therapy assessment may include, for example, assessment of the efficacy of therapy or assessment of the impact of the therapy on the patient. According to various embodiments, therapy efficacy may be determined by evaluating one or more patient conditions sensed or acquired using the sensors 3480, 3490 and/or remote device 3470. The therapy regimen may be adapted to provide more effective therapy. For example, if a delivered therapy does not prevent or otherwise mitigate the patient's disordered breathing, the therapy may be modified to include a more aggressive therapy regimen.

According to embodiments of the invention, the therapy may be adapted to reduce the impact of the therapy on the patient, e.g., to minimally impact the patient. In adapting a reduced impact therapy, the system may take into account various conditions for evaluating the impact of the therapy on the patient. For example, conditions such as patient comfort, as indicated by patient feedback, stress on physiological systems involved in the disordered breathing therapy, interaction with cardiac pacing algorithms, e.g., bradycardia pacing, cardiac resynchronization pacing an/or anti-tachycardia pacing, as determined by interactive effects of the disordered breathing therapy with cardiac pacing, and/or sleep quality, as measured by one or more sleep quality indices, may be taken into account to adapt a disordered breathing therapy regimen that reduces an impact of the therapy on the patient.

In addition, impact to the patient may involve reduction of the useful service life of an implantable therapeutic device used to deliver disordered breathing therapy and/or pacing therapy for cardiac dysfunction. For example, a level of disordered breathing therapy may be unacceptably high if the energy requirements of the therapy result in an excessively reduced device service life. In this situation, early device removal and replacement produces a negative impact to the patient. Therefore, therapy to mitigate disordered breathing may be adapted based on a projected reduction in device useful service life.

In one example, the therapy delivered to mitigate disordered breathing may be adapted to reduce interactions between the disordered breathing therapy and other therapies delivered to the patient. For example, some patients may receive neural stimulation therapy to treat disordered breathing and cardiac stimulation therapy to treat cardiac disorders such as bradycardia or congestive heart failure. Interactions may occur between the neural stimulation therapy and the patient's cardiac pacing regimen, e.g., pacing for bradycardia or cardiac resynchronization. Such interactions may be factored into the assessment of the impact disordered breathing therapy on the overall therapy delivered to the patient.

Therapy for disordered breathing may be adapted by increasing or decreasing an amplitude, frequency, duty, cycle and/or burst frequency of the baroreflex electrical stimulation, for example. In some embodiments, adaptation of the baroreflex electrical stimulation to treat disordered breathing may involve terminating or withholding the electrical stimulation therapy. In one scenario, baroreflex stimulation is delivered as part of therapy for a disorder other than disordered breathing, e.g., hypertension. Baroreflex therapy to treat disordered breathing may involve withholding or terminating the baroreflex stimulation delivered as part of the other therapy regimen.

Figure 35:
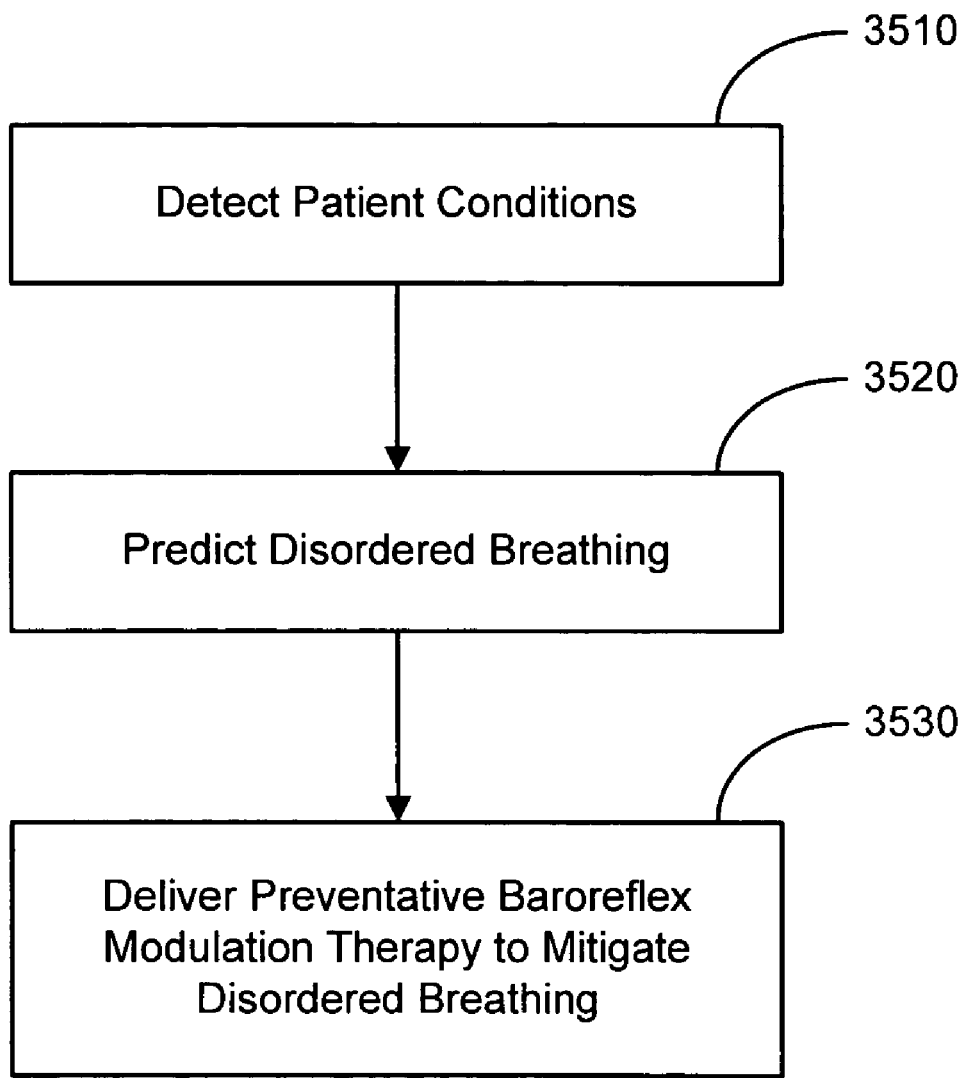
FIGS. 35-37 are flowcharts illustrating methods of providing therapy for disordered breathing according to embodiments of the invention.

FIG. 35 is a flowchart illustrating a method of providing therapy for disordered breathing according to embodiments of the invention. According to this method, one or more patient conditions are detected 3510 and a first group of the detected conditions are used to predict 3520 disordered breathing. A preventative therapy, involving electrical stimulation modulating the patient's baroreflex response is delivered to mitigate the disordered breathing.

A representative set of the first and second groups of patient conditions that may be used for disordered breathing prediction and therapy assessment, respectively, is provided in Table 1. As previously discussed, a first group or subset of conditions may be used in connection with disordered breathing prediction. A second group of conditions, possibly overlapping the first group, may be used for therapy assessment. Several aspects of therapy may be assessed. In one embodiment, therapy is assessed based on therapy effectiveness. In another embodiment, therapy is assessed based on minimal impact to the patient. In yet a further embodiment, therapy is assessed based on a combination of therapy effectiveness and minimal impact to the patient.

As previously discussed, therapy assessment may be implemented by detecting and analyzing one or more patient conditions. Conditions used to assess therapy effectiveness may be different from, or the same as, conditions used to assess the impact of the therapy on the patient. Table 4 provides a representative set of conditions that may be used for therapy assessment.

TABLE 4

| Condition | Therapy Impact | Therapy Efficacy |
|---|---|---|
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy impact. | |
| Pacing algorithm interaction | May be used to assess therapy impact. | |
| Remaining useful life of therapy device | May be used to assess therapy impact. | |

TABLE 4-continued

| Condition | Therapy Impact | Therapy Efficacy |
| --- | --- | --- |
| Pacing algorithm interaction | May be used to assess therapy impact during sleep. | |
| Disturbed Breathing-Based Measures | | May be used to analyze/assess efficacy of therapy to mitigate disordered breathing episodes. |
| Respiration quality (Patient reported) | | May be used to analyze/assess efficacy of therapy to mitigate disordered breathing episodes. |
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection with therapy for disordered breathing are not limited to the representative sets listed in Tables 1-4. Further, although illustrative sensing methods for detecting the patient conditions are provided, it is understood that the patient conditions may be sensed and detected using a wide variety of technologies. The embodiments and features described in the instant disclosure are not limited to the particular patient conditions or the particular sensing technologies described herein.

In one example, conditions related to sleep quality, e.g., sleep fragmentation and other arousal-based measures, patient-reported restful sleep, and discomfort during therapy, may be used to assess the impact of the therapy on the patient. For example, if a patient receiving effective disordered breathing therapy has low sleep fragmentation, reports restful sleep, and reports no discomfort, the adverse effects of the therapy on the patient may be relatively low. If sleep fragmentation is relatively high, or if the patient reports discomfort or feeling tired after sleeping, these conditions may indicate that therapy is causing sleep disturbance and/or other undesirable effects. Various methods and systems for collecting sleep quality data and assessing sleep quality are described in a commonly owned U.S. Patent Application Publication No. 2005/0042589, which is hereby incorporated herein by reference.

Sleep fragmentation and sleep disruptions may also occur if disordered breathing therapy is ineffective and disordered breathing occurs during sleep. Therefore, a therapy impact assessment based on detected sleep quality and/or patient-reported restful sleep preferably takes into account an assessment of therapy effectiveness.

Some patients may receive cardiac electrical stimulation therapy for both disordered breathing as well as cardiac disorders such as bradycardia and/or CHF. Interactions may occur between cardiac electrical therapy to mitigate disordered breathing and the patient's cardiac pacing regimen, e.g., pacing for bradycardia or cardiac resynchronization. Such interactions may be factored into the assessment of the impact of disordered breathing therapy on the overall therapy delivered to the patient.

Interactions between neural stimulation therapy and cardiac stimulation therapy may occur, and detection of the interactions may be used to adjust therapy. In some cases, neural stimulation therapy to mitigate disordered breathing may enhance cardiac pacing therapy directed to alleviate a cardiac dysfunction, such as bradycardia or CHF. For example, non-excitatory electrical stimulation of the left ventricle during an absolute refractory period may be beneficial to treat both CHF and disordered breathing.

The effectiveness of disordered breathing therapy may be assessed by detecting and analyzing episodes of disordered breathing that occur even though therapy is being delivered to mitigate disordered breathing. As indicated, a number of conditions listed in Table 3 may be used in connection with the detection of disordered breathing.

Figure 36:
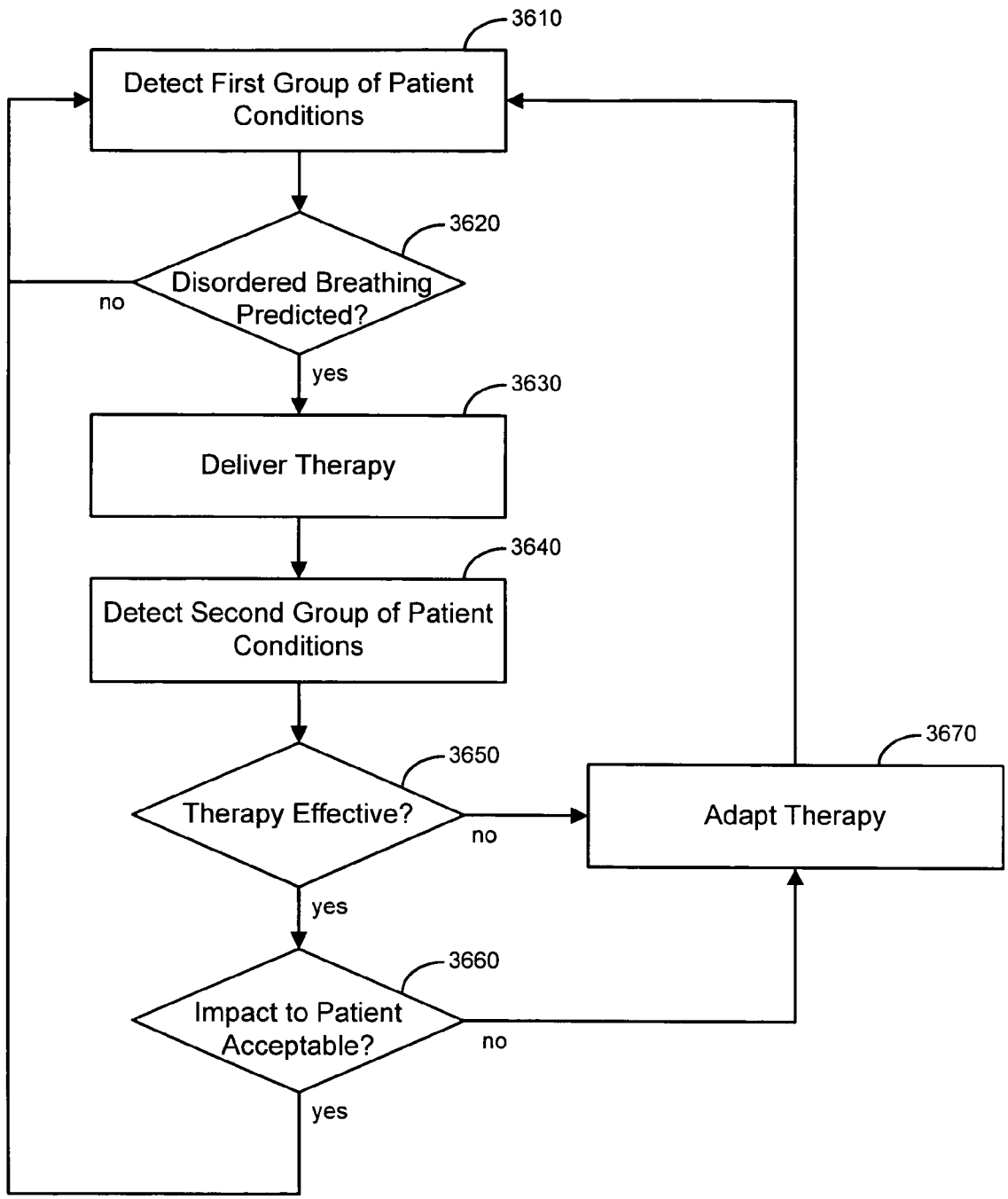

The flowchart of FIG. 36 illustrates a method of providing disordered breathing therapy in accordance with embodiments of the invention. A first group of patient conditions is detected 3610 and disordered breathing predicted 3620 based on the first group of patient conditions. Therapy to mitigate or prevent the disordered breathing is delivered 3630. A second group of conditions is detected 3640 and used to assess 3650 the effectiveness of the therapy. The second group of conditions may include, for example, conditions used to detect disordered breathing and analyze the type, frequency, duration, and severity of disordered breathing episodes. If therapy is ineffective 3660, the therapy regimen may be adjusted 3670.

One or more conditions of the second group of conditions are used to assess 3660 the impact of the therapy on the patient. If the therapy impacts the patient negatively, for example, by disrupting sleep or causing discomfort, then therapy parameters may be adjusted, e.g., to provide a less aggressive therapy regimen.

According to various embodiments of the invention, disordered breathing detection may be used to assess therapy effectiveness. In one example implementation, episodes of disordered breathing are detected by analyzing the patient's respiration.

Figure 37:
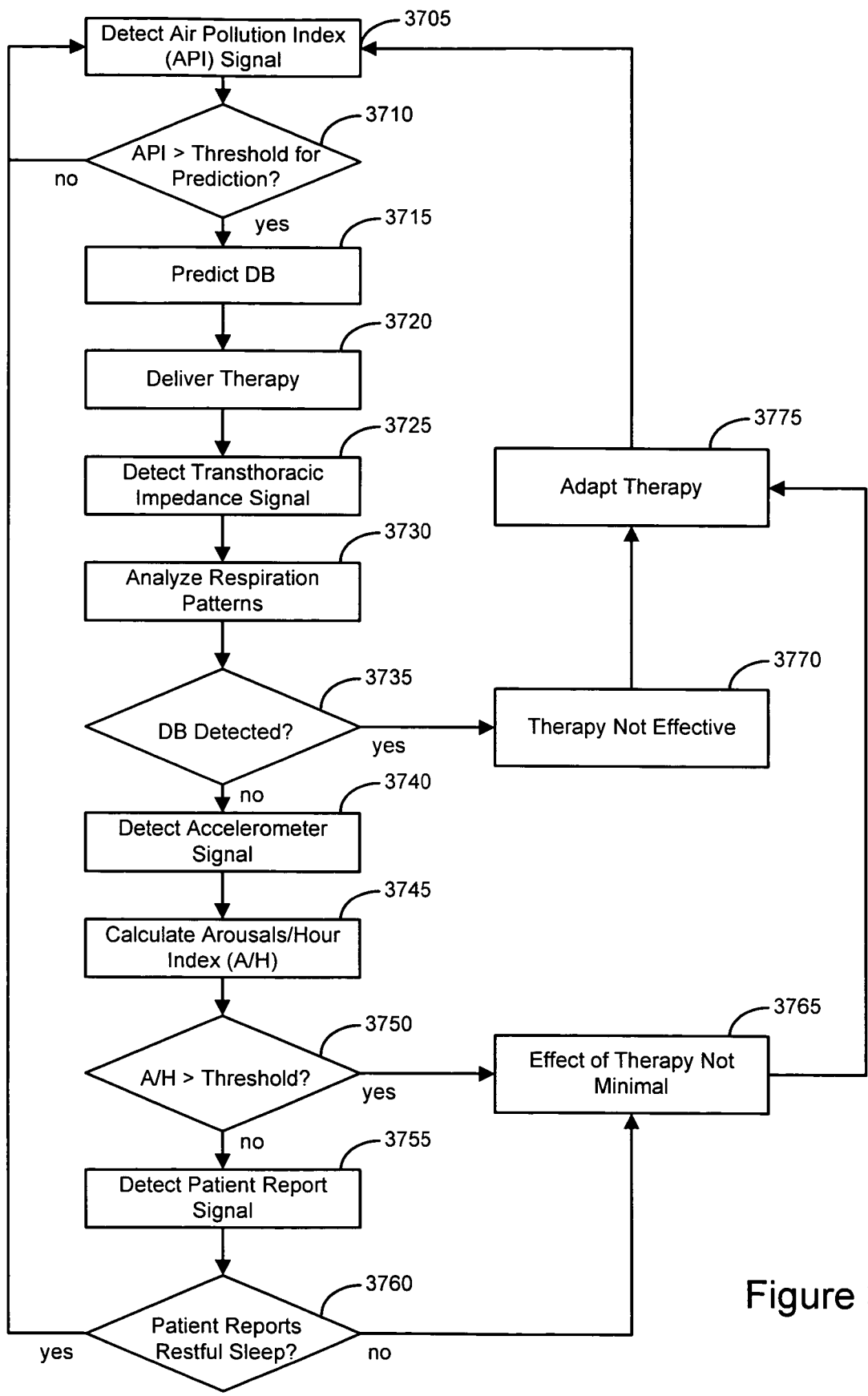

FIG. 37 is a flowchart illustrating a method of providing therapy for disordered breathing in accordance with embodiments of the invention. The cardiac pacing therapy is triggered by a prediction of disordered breathing. In this example, disordered breathing is predicted based on an air pollution index obtained from an internet accessible server.

Therapy efficacy is assessed by analyzing respiration patterns detected using a transthoracic impedance sensor to detect episodes of disordered breathing. The impact of the therapy on the patient's sleep is analyzed by determining the number of arousals per hour experienced by the patient.

As illustrated in FIG. 37, an air pollution index is detected 3705, for example, by accessing an internet-connected website. If the air pollution index exceeds a selected threshold 3710, then disordered breathing is predicted 3715. The air pollution index threshold may be selected, for example, from data collected over time from the patient. If disordered breathing is predicted 3715, therapy to mitigate the disordered breathing, e.g., stimulation of the patient's baroreflex response, is delivered 3720 to the patient. The parameters of the baroreflex therapy, e.g., amplitude, frequency, duty cycle, etc., may be modified to increase the efficacy of the therapy or to reduce the impact of the therapy on the patient.

A transthoracic impedance signal is sensed 3725 and used to analyze 3730 respiration patterns associated with disordered breathing. If disordered breathing is detected 3735, then the delivered therapy may not have been effective 3770. If therapy is found to be ineffective, the therapy may be adapted 3775.

In one embodiment, if the frequency, duration, or severity of the disordered breathing episodes is not mitigated following therapy delivery, the therapy may be determined to be ineffective and the baroreflex therapy may be adapted to a more aggressive therapy involving increase stimulation of the baroreflex. Severity of disordered breathing events may be assessed, for example, as a percentage decrease in tidal volume from the recent average or baseline tidal volume.

Disordered breathing time duration thresholds may be defined to trigger a disordered breathing episode. For example, a disordered breathing episode may be declared if the patient's tidal volume falls below an apnea or hypopnea tidal volume threshold for a period exceeding a disordered breathing duration threshold such as about 10 seconds. A severe disordered breathing episode may be declared when the patient's tidal volume falls below an apnea or hypopnea tidal volume threshold for a period exceeding a severe disordered breathing duration threshold, e.g., about 60 seconds. If a severe apnea episode is detected, the severe apnea episode may trigger pacing at a high rate to arouse the patient and terminate the apnea. A pacing rate upper limit may be employed to prevent the pacing rate from becoming too high.

In one embodiment, if the therapy is determined to be effective, the intensity of the baroreflex therapy may be gradually decreased to reduce the risk of arousal, to avoid unnecessary stress on the heart, and to prolong battery life.

If the disordered breathing therapy is determined to be effective 3735, the impact of the therapy on the patient is assessed. The patient's sleep quality may be determined by analyzing patient activity using an accelerometer, for example. Additional sensors may also be used to provide more sensitive arousal detection. The accelerometer signal is sensed 3740 and used to determine 3745 the number of arousals per hour (A/H) experienced by the patient. If the number of arousals per hour is greater 3750 than a threshold value, then the therapy may be arousing the patient from sleep. In this situation, the impact of the therapy is not minimal 2165, and the therapy may be adapted 3775. The impact of the therapy may be further assessed using patient-reported input 3755. If the patient reports that sleep is not restful 3760, then the therapy regimen may be adapted 3775.

Although a number of the examples of disordered breathing therapy provided above involve types of disordered breathing that generally occur while a person is asleep, disordered breathing may also occur while a person is awake. While the methods, devices, and systems of the invention described herein are particularly well-suited for providing sleep-disordered breathing therapy, the principles of the invention are also applicable to provided therapy for disordered breathing episodes that occur while the patient is awake. Waking disordered breathing is frequently associated with compromised cardiopulmonary function caused by congestive heart failure. Examples of the types of disordered breathing that may occur while a person is awake include, for example, periodic breathing and Cheyne-Stokes respiration. Cheyne-Stokes respiration particularly affects patients who have heart problems, such as congestive heart failure, or nervous disorders, such as those caused by a stroke.

A number of the examples presented herein involve block diagrams illustrating functional blocks used for in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of providing disordered breathing therapy to a patient, comprising:
   delivering a plurality of therapies to treat disordered breathing, including at least a first therapy utilizing electrical stimulation that modulates a patient's baroreflex response, and including a second therapy different from the first therapy;
   sensing one or more conditions associated with the patient;
   determining, from the one or more sensed conditions, an efficacy of at least one therapy of the first and second therapies in treating disordered breathing;
   determining, from the one or more sensed conditions, an impact on the patient other than the efficacy of the at least one therapy;
   modifying the at least one therapy if the efficacy is determined to be acceptable and the impact is determined to be unacceptable.

2. The method of claim 1, wherein the impact on the patient relates to the patient's sleep quality, and the coordinating is carried out to enhance the patient's sleep quality.

3. The method of claim 2, wherein the sleep quality is determined at least in part by measuring a level of fragmentation of the patient's sleep.

4. The method of claim 2, wherein the sleep quality is determined at least in part by sensing arousals of the patient from sleep.

5. The method of claim 2, wherein the sleep quality is determined at least in part by receiving patient-reported assessments of sleep quality.

6. The method of claim 2, wherein the modifying modifies the at least one therapy to deliver less aggressive therapy to enhance the patient's sleep quality.

7. The method of claim 1, wherein the impact on the patient relates to the patient's discomfort during therapy, and the modifying is carried out to reduce the patient's discomfort during therapy.

8. The method of claim 1, wherein the delivering, sensing, and modifying steps are provided at least in part by an implantable device, wherein the impact on the patient relates to a service life of the implantable device, and wherein the modifying is carried out to enhance the service life of the implantable device.

9. The method of claim 1, further comprising:
delivering at least one cardiac pacing therapy to the patient;
wherein the impact on the patient relates to interactions between the plurality of therapies to treat disordered breathing and the at least one cardiac pacing therapy.

10. The method of claim 9, wherein the modifying is carried out to reduce the interactions.

11. The method of claim 10, wherein the modifying includes delivering the first therapy during a refractory period of the patient's heart.

12. The method of claim 1, wherein the second therapy includes non-excitatory electrical stimulation of the patient's heart.

13. The method of claim 1, wherein the second therapy includes sub-capture threshold electrical stimulation of the patient's heart.

14. The method of claim 1, wherein the second therapy includes overdrive pacing of the patient's heart.

15. The method of claim 1, wherein the second therapy includes a patient-external respiratory therapy.

16. The method of claim 15, wherein the impact of the second therapy on the patient relates to whether the patient has used the external respiratory therapy.

17. The method of claim 1, wherein coordinating delivery includes delivering the first and second therapies for predetermined periods of time.

18. The method of claim 1, wherein modifying includes shifting from the first to the second therapy.

19. A disordered breathing therapy system at least a portion of which is adapted for implantation in a patient, the system comprising:
a plurality of therapy devices, each therapy device configured to deliver a disordered breathing therapy different from disordered breathing therapies delivered by others of the therapy devices;
a plurality of sensors capable of sensing at least one condition associated with the patient; and
a therapy controller coupled to the plurality of therapy devices and to the plurality of sensors, the therapy controller configured to:
determine from the at least one condition an efficacy of at least one therapy of the disordered breathing therapies in treating disordered breathing;
determine from the at least one condition an impact on the patient other than the efficacy of the at least one therapy; and
modify the at least one therapy if the efficacy is determined to be acceptable and the impact is determined to be unacceptable;
wherein at least one of the therapy devices includes a baroreflex stimulator configured to deliver an electrical stimulation therapy modifying the patient's baroreflex response.

20. The system of claim 19, wherein at least the baroreflex stimulator and the therapy controller are adapted for implantation in the patient.

21. The system of claim 19, wherein the at least one condition includes a condition that relates to the patient's sleep quality, and wherein the therapy controller is configured to modify the at least one therapy so as to enhance the patient's sleep quality.

22. The system of claim 21, wherein the sleep quality is determined at least in part by measuring a level of fragmentation of the patient's sleep.

23. The system of claim 21, wherein the sleep quality is determined at least in part by sensing arousals of the patient from sleep.

24. The system of claim 21, wherein the sleep quality is determined at least in part by receiving patient-reported assessments of sleep quality.

25. The system of claim 21, wherein the therapy controller modifies the at least one therapy by delivering less aggressive therapy to enhance the patient's sleep quality.

26. The system of claim 19, wherein the impact on the patient relates to the patient's discomfort during therapy, and the therapy controller is adapted to reduce the patient's discomfort during therapy.

27. The system of claim 19, wherein at least the baroreflex stimulator and the therapy controller are part of an implantable device, and wherein the impact on the patient relates to a service life of the implantable device, and wherein the therapy controller is adapted to enhance the service life of the implantable device.

28. The system of claim 19, further comprising:
a cardiac pacing therapy device coupled to the therapy controller;
wherein the impact on the patient relates to interactions between the plurality of therapy devices configured to deliver the disordered breathing therapies and the cardiac pacing therapy device.

29. The system of claim 28, wherein the therapy controller is configured to reduce the interactions between the plurality of therapy devices configured to deliver the disordered breathing therapies and the cardiac pacing therapy device.

30. The system of claim 29, wherein the therapy controller is configured to deliver the electrical stimulation therapy modifying the patient's baroreflex response during a refractory period of the patient's heart.

31. The system of claim 19, wherein the plurality of therapy devices includes a device configured to deliver non-excitatory electrical stimulation of the patient's heart.

32. The system of claim 19, wherein the plurality of therapy devices includes a device configured to deliver sub-capture threshold electrical stimulation of the patient's heart.

33. The system of claim 19, wherein the plurality of therapy devices includes a device configured to deliver overdrive pacing of the patient's heart.

34. The system of claim 19, wherein the plurality of therapy devices includes an external respiratory therapy device.

35. The system of claim 34, wherein the therapy controller is configured to modify the at least one therapy based on whether the patient has used the external respiratory therapy device.

36. The system of claim 19, wherein the therapy controller is configured to modify the at least one therapy by shifting from one to another of the plurality of therapy devices upon sensing that the patient is asleep.

* * * * *

UNITED STATES PATENT AND TRADEMARK OFFICE
CERTIFICATE OF CORRECTION

PATENT NO. : 7,596,413 B2 Page 1 of 1
APPLICATION NO. : 10/863827
DATED : September 29, 2009
INVENTOR(S) : Libbus et al.

It is certified that error appears in the above-identified patent and that said Letters Patent is hereby corrected as shown below:

In the Specification:

Col. 38, line 14: "level of f(x before" should read --level of f(x) before--.

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO.         : 7,596,413 B2                        Page 1 of 1
APPLICATION NO. : 10/863827
DATED              : September 29, 2009
INVENTOR(S)       : Libbus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 924 days.

Signed and Sealed this

Twenty-eighth Day of September, 2010

David J. Kappos
*Director of the United States Patent and Trademark Office*